(12) United States Patent
Shimoide et al.

(10) Patent No.: US 7,105,354 B1
(45) Date of Patent: Sep. 12, 2006

(54) ANALYZER

(75) Inventors: Koji Shimoide, Fuji (JP); Akira Kiguchi, Yokohama (JP); Shigemi Mukaiyama, Yokohama (JP); Hiroshi Kurokawa, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/719,406

(22) PCT Filed: Jun. 14, 1999

(86) PCT No.: PCT/JP99/03158

§ 371 (c)(1),
(2), (4) Date: Dec. 12, 2000

(87) PCT Pub. No.: WO99/64846

PCT Pub. Date: Dec. 16, 1999

(30) Foreign Application Priority Data

Jun. 12, 1998 (JP) ................................ 10-181586

(51) Int. Cl.
*G01N 21/00* (2006.01)
*G01N 21/03* (2006.01)
*G01N 33/00* (2006.01)
*G01N 15/06* (2006.01)
*G01N 33/48* (2006.01)

(52) U.S. Cl. ...................... 436/164; 436/165; 436/147; 436/171; 422/68.1; 422/69; 422/91; 422/82.09

(58) Field of Classification Search ................ 422/101, 422/102, 82.09, 62, 68.1, 69, 91; 204/603; 356/440; 436/164, 165, 171, 147
See application file for complete search history.

(56) References Cited

U.S. PATENT DOCUMENTS 3,793,541 A * 2/1974 Ashkin et al. .................. 372/3
4,439,492 A    3/1984 Wada et al.
4,682,897 A * 7/1987 Saito et al. .................... 374/45

(Continued)

FOREIGN PATENT DOCUMENTS

EP    0 708 331 A1    4/1996

(Continued)

OTHER PUBLICATIONS

Luk'yanov, A. Yu, Compact photothermal-refractometric detector for high performance liquid chromatography based on a polarization interferometer, Review of Sicentific Instruments, vol. 74, No. 1 pp. 656-658.*

(Continued)

*Primary Examiner*—Jill Warden
*Assistant Examiner*—Brian R Gordon
(74) *Attorney, Agent, or Firm*—Finnegan, Henderson, Farabow, Garrett & Dunner, L.L.P.

(57) ABSTRACT

An analyzer characterized by comprising a chip and a detector, wherein the chip is an organic polymer member having a fine capillary through which a fluid sample or a fluid sample and a fluid reagent flow and can perform a chemical reaction on the sample in the capillary without using a separate weighing means, and the detector is a photothermal conversion detector for measuring a physical quantity change such as a refractive index change caused by a partial temperature change of the sample and the reagent by applying an excitation light to a substance to be measured produced by the chemical reaction, thereby providing a small analyzer excellent in chip waste-disposal, capable of analyzing inexpensively, simply and in a short time and being suitable for a POC analysis.

9 Claims, 22 Drawing Sheets

U.S. PATENT DOCUMENTS

| | | | |
|---|---|---|---|
| 4,724,314 A * | 2/1988 | Caimi | 250/205 |
| 4,906,095 A * | 3/1990 | Johnston | 356/484 |
| 4,938,593 A * | 7/1990 | Morris et al. | 356/344 |
| 5,126,022 A | 6/1992 | Soane et al. | |
| 5,141,331 A * | 8/1992 | Oehler et al. | 374/118 |
| 5,409,777 A * | 4/1995 | Kennedy et al. | 428/411.1 |
| 5,415,841 A | 5/1995 | Dovichi et al. | |
| 5,513,006 A | 4/1996 | Schulz et al. | |
| 5,571,410 A | 11/1996 | Swedberg et al. | |
| 5,578,460 A * | 11/1996 | Ebersole et al. | 435/29 |
| 5,622,868 A * | 4/1997 | Clarke et al. | 436/147 |
| 5,641,400 A | 6/1997 | Kaltenbach et al. | |
| 5,716,852 A | 2/1998 | Yager et al. | |
| 5,785,831 A | 7/1998 | Bek | |
| 5,858,195 A * | 1/1999 | Ramsey | 204/601 |
| 5,926,273 A * | 7/1999 | Kimura et al. | 356/502 |
| 6,081,127 A * | 6/2000 | Wagner et al. | 324/765 |
| 6,087,181 A * | 7/2000 | Cong | 436/37 |
| 6,159,686 A * | 12/2000 | Kardos et al. | 435/6 |
| 6,261,469 B1 * | 7/2001 | Zakhidov et al. | 216/56 |
| 6,319,469 B1 * | 11/2001 | Mian et al. | 422/64 |
| 6,322,735 B1 * | 11/2001 | Yamaki et al. | 264/69 |
| 6,381,025 B1 * | 4/2002 | Bornhop et al. | 356/517 |
| 6,623,970 B1 * | 9/2003 | Willson, III | 436/37 |
| 6,930,778 B1 * | 8/2005 | Yamaguchi et al. | 356/432 |
| 2002/0094580 A1 * | 7/2002 | Jorgenson et al. | 436/151 |
| 2002/0137218 A1 * | 9/2002 | Mian et al. | 436/45 |
| 2002/0155033 A1 * | 10/2002 | Strand et al. | 422/101 |
| 2002/0176804 A1 * | 11/2002 | Strand et al. | 422/100 |
| 2003/0017079 A1 * | 1/2003 | Hahn et al. | 422/82.09 |
| 2003/0040118 A1 * | 2/2003 | Potyrailo et al. | 436/52 |
| 2003/0118480 A1 * | 6/2003 | Kaylor et al. | 422/69 |
| 2003/0138941 A1 * | 7/2003 | Gong et al. | 435/287.2 |
| 2003/0175947 A1 * | 9/2003 | Liu et al. | 435/288.5 |
| 2003/0223070 A1 * | 12/2003 | Yamaguchi et al. | 356/432 |
| 2004/0021935 A1 * | 2/2004 | Kitamori et al. | 359/368 |
| 2004/0071597 A1 * | 4/2004 | Hattori et al. | 422/82.05 |

FOREIGN PATENT DOCUMENTS

| | | |
|---|---|---|
| JP | 57008131 | 1/1982 |
| JP | 60-174933 | 9/1985 |
| JP | 62-58287 | 3/1987 |
| JP | 2-245655 | 10/1990 |
| JP | 02-259557 | 10/1990 |
| JP | 04-64063 | 2/1992 |
| JP | 04-369467 | 12/1992 |
| JP | 5-504628 | 7/1993 |
| JP | 06-283830 | 10/1994 |
| JP | 8-261986 | 10/1996 |
| JP | 08-304339 | 11/1996 |
| JP | 8-327597 | 12/1996 |
| JP | 8-334505 | 12/1996 |
| JP | 2-601595 | 1/1997 |
| JP | 09-72898 | 3/1997 |
| JP | 2-639087 | 4/1997 |
| JP | 09-229883 | 9/1997 |
| JP | 10-50719 | 2/1998 |
| JP | 10-128783 | 5/1998 |
| JP | 10-142177 | 5/1998 |
| JP | 2000-2675 | 1/2000 |
| JP | 2000-2677 | 1/2000 |
| WO | WO 91/12904 | 9/1991 |
| WO | WO 97/39338 | 10/1997 |
| WO | WO 97/47390 | 12/1997 |

OTHER PUBLICATIONS

Nolan, Thomas G., Photothermal Refraction as a Microbore Liquid Chromatography Detector in Femtomole Amino Acid Determination, Analyical Chemistry, 1985 vol. 57 pp. 2703-2705.*

Terazima, Masahide; Refractive index change by photothermal effect with a constant density detected as tempeature grating in various fluids; J. Chem. Phy. 104 (13), Apr. 1, 1996.*

Analysis No. 4, pp. 280-284 (1997).

Japan Analytical Chemistry, Abstracts of 44th Annual Meeting, pp. 119, (1995).

Journal of Japan Mechanics Association 100, pp. 615-617 (1997).

Sensor/Actuator/Week 1997 General Symposium Abstracts "Microsensor", Session 3, pp. 19-23, (Apr. 17, 1997).

Ogawa, Z. et. al., Clinical Investigation, vol. 41, No. 4, pp. 981-988, (1997).

Kanno, T. Clinical Investigation, vol. 42, No. 3, pp. 309-312, (1998).

Molding Symposia 1995, "Improvement of Flow Length of Injection Molded Polymer Products Utilizing a Radiactive Heating", pp. 241-242, (1995).

Molding 1996, pp. 69-72, (1996).

Manz, A. et al., "Miniaturized Total chemical Analysis Systems: a Novel Concept for Chemical Sensing", Sensors and Actuators, B1, pp. 244-248, (1990).

McCormick, R.M. et al., "Microchannel Electrophoretic Separations of DNA in Injection-Molded Plastic Substrates", Analytical Chemistry, vol. 69, No. 14, pp. 2626-2630, (1997).

Jacobson, S.C. et al., "Precolumn Reactions with Electrophorectic Analysis Integrated on a Microchip", Analytical Chemistry, vol. 66, No. 23, pp. 4127-4132, (1994).

Kuroda, N. et al., "Determination of Methamphetamine and Related Compounds by Capillary Electrophoresis with UV and Laser-Induced Fluorescence Detection", Journal of Chromatography A, No. 798, pp. 325-334, (1998).

Regehr, M.F. et al., "Chemiluminescent Detection for Capillary Electrophoresis and EMMA Enzyme Assays", Journal of Capillary Electrophor., vol. 3, pp. 117-124, (1996).

Boccara, A.C. et al., "Thermo-Optical Spectroscopy: Detection by the "Mirage Effect"", Appl. Phys. Lett., vol. 36, No. 2, pp. 130-132, (1980).

Earle, C.W. et al., "Simultaneous Two-Color Thermo-Optical Absorbance Detector for Capillary Zone Electrophoresis", Journal of Liquid Chromatography, vol. 12, No. 13, pp. 2575-2585, (1989).

Harada, M. et al., "Photothermal Microscopy with Excitation and Probe Beams Coaxial under the Microscope and Its Application to Microparticle Analysis", Analytical Chemistry, vol. 65, No. 20, pp. 2938-2940, (1993).

Manz, A. et al., "Micromachining of Monocrystalline Silicon and Glass for Chemical Analysis Systems; A Look into Next Century's Technology or Just a Fashionable Craze?", Trends in Analytical Chemistry, vol. 10, No. 5, pp. 144-149, (1991).

Verpoorte, E.M.J. et al., "Three-Dimensional Micro Flow Manifolds for Miniaturized Chemical Analysis Systems", J. Micromech. Microeng., vol. 4, pp. 246-256, (1994).

Verpoorte, E.M.J. et al., "Silicon-Based Chemical Microsensors and Microsystems", Interfacial Design and Chemical Sensing, American Chemical Society, Chapter 21, pp. 244-254, (1994).

Waters, L.C. et al., "Microchip Device for Cell Lysis Multiplex PCR Amplification, and Electrophoretic Sizing", Analytical Chemistry, vol. 70, No. 1, pp. 158-162, (1998).

Synthetic Resin, vol. 42, (1), 48 (1992).

K. Matsumoto, et al., "Nano-Channel on Quartz-Chip Laboratory Using Single Molecular Detectable Thermal Lens Microscope," Micro Electro Mechanical Systems, 1998. MEMS 98. Proceedings., The Eleventh Annual International Workshop on Heidelberg, Germany Jan. 25-29, 1998, New York, NY, USA, IEEE, US, Jan. 25, 1998, pp. 127-130.

* cited by examiner

FIG. 15

| LASER WAVELENGTH | | (a) | (b) | (c) | (d) | (e) | (f) | (g) | (h) | (i) | (j) | (k) | (l) |
|---|---|---|---|---|---|---|---|---|---|---|---|---|---|
| 488nm | ABSORBANCE Ave. / SD | --- | 0.0002 / 0.0004 | --- | 0.0008 / 0.0033 | 0.0007 / 0.0034 | 0.0010 / 0.0014 | 0.0030 / 0.0000 | 0.0010 / 0.0009 | 0.0023 / 0.0005 | 0.0078 / 0.0031 | 0.0513 / 0.0046 | 0.0132 / 0.0073 |
| | ABSORPTANCE CONVERTED FOR t=2.3 mm | | 0.53% | | 0.15% | 0.37% | 0.53% | 1.06% | 1.06% | 1.22% | 2.05% | 12.81% | ※5.99% |
| 633nm | ABSORBANCE Ave. / SD | --- | --- | --- | --- | --- | --- | 0.0030 / 0.0000 | 0.0011 / 0.0009 | 0.0043 / 0.0005 | 0.0073 / 0.0029 | 0.0453 / 0.0041 | 0.0085 / 0.0050 |
| | ABSORPTANCE CONVERTED FOR t=2.3 mm | | | | | | | 1.06% | 1.16% | 2.27% | 1.92% | 11.40% | ※3.88% |
| 780nm | ABSORBANCE Ave. / SD | 0.0011 / 0.0009 | 0.0025 / 0.0008 | 0.0048 / 0.0017 | 0.0048 / 0.0039 | 0.0020 / 0.0009 | 0.0022 / 0.0011 | 0.0025 / 0.0005 | 0.0008 / 0.0010 | | 0.0090 / 0.0028 | 0.0202 / 0.0041 | 0.0048 / 0.0055 |
| | ABSORPTANCE CONVERTED FOR t=2.3 mm | 0.59% | 0.89% | 0.46% | 0.84% | 1.06% | 1.16% | 0.89% | 0.87% | | 2.36% | 5.22% | ※2.20% |
| OUTPUT BY THERMAL LENS DETECTION (WAVELENGTH OF EXCITATION LIGHT:633nm) POLYMER ITSELF | | ABOUT 0.2mV | ABOUT 0.2mV | ABOUT 0.2mV | ABOUT 0.2mV | ABOUT 0.2mV | 0.3mV | 2.6mV | 0.9mV | 10.2mV | 1.8mV | 47mV | 10mV |

--- INDICATES BELOW THE MEASUREMENT LIMIT.    ※VALUE WHEN t=100μm

ANALYZER

TECHNICAL FIELD

The present invention relates to an analyzer for simply analyzing and detecting a trace amount of samples.

BACKGROUND ART

Attention is given to the importance of performing analysis or measurement at or near locations where analysis or measurement is required (hereinafter referred to generally as "POC analyses etc."), such as analysis for bedside diagnosis performing measurement necessary for medical diagnosis near a patient (POC (point of care) analyses), analysis of hazardous substances in rivers and wastes at locations such as rivers, dumping grounds and the like, and inspection of contamination in each location of cooking, harvesting, and importing foods, and emphasis is currently put on the development of detection methods and equipment applied to these POC analyses etc. These POC analyses etc. are required to be performed simply, in a short time and inexpensively.

As for conventional micro analyses methods, GCMS equipment and LCMS equipment for quantifying samples by a mass spectrometer after separating the sample by capillary gas chromatography (CGC), capillary liquid chromatography (CLC) and the like have been generally used. However, these analyzers are not suitable for use in such measurement locations as the bedside of patients, contaminated rivers and dumping grounds because mass spectrometers are large in size and operations are complicated. Furthermore, for analyzers for use in medical diagnosis using blood and the like as samples, it is desirable that sample contacting portions are disposable.

To solve these problems, a concept of analysis method generally called μTAS (micro total analysis system) intended to make conventionally used analyzers smaller and carry out reaction and separation of samples using chips of a few centimeter square including capillaries to perform electrophoresis for simply performing micro analysis has been proposed (Sensors and Actuators, B1 (1990), 244–248, A. Manz et al.). This μTAS has advantages that the amount of samples and reagents required for detection of components and the amount of wastes and effluent waste of consumable items used for detection and the like are reduced, and detection can be done in a short time.

The μTAS is constituted by samples consisting of liquids, gases and the like in the chip (hereinafter referred to as "fluid"), means for transporting reagents and means for achieving their reactions, etc. in addition to the aforesaid chips and analysis methods, for each of which research is being performed. However, each of them has disadvantages as describe below, and a comprehensive μTAS combining all of these components is not completed yet in the present circumstances.

For example, materials forming capillary are generally glass and silicon that can be finely processed with high accuracy (For example, Japanese Patent Laid-Open No. 2-245655), but they also have disadvantages that the process cost is high and careful handling is required because they are apt to break, and the like. Furthermore, as described above, for use in medical diagnosis and the like, it is desirable that chips are disposable because they contact samples originated from patients such as blood etc., but materials such as glass and silicon are incombustible, thus raising problems also in waste treatment. As research intended to solve these problems arising when glass and silicon are used, a method in which chips are produced from resin (R. M. McCormick et al./Anal. Chem. Vol. 69, No. 14 (1997) 2626–2630, Japanese Patent Laid-Open No. 2-259557, Japanese Patent No. 2639087 (Registration: Apr. 25, 1997, Shimadzu Corp.). The method of producing resin chips includes a method in which the surface of Si-wafer is processed applying semiconductor fine processing technology, followed by electrocasting Ni and removing Si by dissolution and the like to fabricate a master processed with resin, and then acrylic resin or the like is injection-molded using the above described master as a matrix to mold chips (Analytical Chemistry 69, 2626–2630 (1997) (Aclara Biosciences)).

In this way, chips made of resin are excellent in disposability and mass-producibility, but have problems as described below if fluorescent methods, absorptiometric methods and the like used in conventional detection equipment are adopted as means for detecting substances in the chip as in case of glass and silicon.

Prior arts will be further described below with emphasis on detection equipment.

Methods of analyzing samples flowing in the capillary generally include fluorescence spectroscopic methods (for example, S. C. Jacobson et al., Anal. Chem. Vol. 66, 4127–4132, 1994, Japanese Patent Laid-Open No. 2-245655), absorptiometric methods (for example, N. Kuroda et al., J. Chrom atogr., Vol. 798, 325–334, 1998), and chemical luminescent methods (for example, M. F. Regehr et al., J. Capillary Electrophor, Vol. 3, 117–124, 1996).

Of these methods, the chemical luminescent method and fluorescent method are methods in which a substance to be detected is changed into a compound in excited state in the presence of a catalyst such as an oxidizer and energy emitted as light when the compound changes from this state to a ground state is detected (in case of fluorescent method, energy is transferred to an energy acceptor coexisting with the excited compound and the energy emitted when this acceptor changes from an excited state to a ground state is detected). On the other hand, the absorptiometric method is a method in which light is introduced in a solution containing a substance to be detected for measuring the intensity of transmitted light and determining the ratio of the intensity of the transmitted light to the intensity of the incoming light. As for sensitivity, it is generally said that the ranking is, from lowest to highest, the absorptiometric method, the fluorescent method and the chemical luminescent method.

As major chemical luminescent reactions, methods by luminol and lucigenine have been known for a long time. Also the chemical luminescent reaction has advantages such as high speed and high sensitivity and relatively inexpensive equipment because no light source is required for detection, but it has disadvantages that luminescence is rapidly decayed, reagents for use are unstable, the background is high and so forth.

In a similar way, the fluorescent method has an advantage that its reaction system has been known for a long time, but it requires the source of excitation light as an optical system and optical filters for separating excitation light and fluorescence, and the like.

Also, these methods using luminescent phenomena have a problem of poor light-intercepting efficiency because emitted light is diverged in all directions. In case of fluorescent method, general versatility is not high because the yield of emitting fluorescence is low and it is necessary to establish a reaction system for converting an object substance to be measured into a limited fluorescent substance.

In particular, in the field of clinical investigation for medical diagnosis, since integration of measured values into those with standard methods defined by academic societies and the like is in progress, substantial changes in measurement systems may raise problems.

Also, the absorptiometric method has a disadvantage that it is necessary to make the length of optical path large so as to obtain accurate results and particularly long optical path is obtained for detecting a trace amount of samples, thereby making the structure of detection cells complicated, because the ratio of incoming light to transmitted light is detected in principle.

In this way, the detection with conventional absorptiometric methods and fluorescent methods using cuvettes and the like can be carried out using relatively small equipment, but the measurement with chips equipped with capillaries intended for application to the POC analyses etc. allows only small length of optical path because the diameter of the capillary is reduced, and only low sensitivity can be obtained.

Methods in which light is not applied to the capillary vertically but is applied in the flow direction in order to make the length of optical path larger have been proposed (for example, Japanese Patent Laid-Open No. 8-304339), but these methods have a disadvantage that detection in the flow direction is not easy in case of capillaries formed on the plane chips and the chip structure and the structure of detecting portions are more complicated.

As another method of detecting a trace amount of components, the photothermal detection method (thermal lens detection method) has been long known in which samples in liquid are excited with an excitation light to form so-called thermal lens and changes in the thermal lens are measured with a detection light (Japanese Patent Laid-Open No. 60-174933, A. C. Boccara et al., Appl. Phys. Lett. 36, 130, 1980).

In the photothermal detection method, a thermal lens with thickness of about 0.1 μm to 1 mm is usually formed by excitation light. In case sufficient length of optical path, for example, about 1 cm can be provided, the photothermal detection method is not usually used because two kinds of light sources, i.e. excitation light and detection light are usually required, in contrast to the absorptiometric method and fluorescent method. Also, the excitation light and detection light are made coaxial and are let in the capillary, thus causing the equipment to be complicated. However, methods in which two lasers are not made coaxial but made to cross or face each other (J. Liquid Chromatography 12, 2575–2585 (1989), Japanese Patent Laid-Open No. 10-142177 (Molecular Biophotonics)) and methods in which one laser is diverged for use and the shift in focal position itself due to photothermal conversion is detected (Japanese Patent Laid-Open No. 4-369467 (Yokogawa Electric Corp.)) have also been proposed.

One example of photothermal detection methods using Ar laser and He—Ne laser is a method in which a sample is placed on a glass plate and sandwiched with another glass plate (Anal. Chem. 65, 2938–2940 (1993)).

Furthermore, there is an example that application has been made from the outside of a plane chip comprising capillaries to an analyzer that sends liquid using pumps. (Analysis No. 4, 280–284, 1997, M. Harada et al., Anal. Chem. Vol. 65, 2938–2940, 1993, Kawanishi et al., Japan Analytical Chemistry, Abstracts of 44th Annual Meeting, p. 119, 1995, etc.)

These photothermal detection methods are mainly intended to improve local absolute sensitivity as of "How many molecules can be detected." Thus, methods are dominating in which laser is focused as much as possible, the excitation light is concentrated in a small volume and the thermal lens occurring in the micro space is detected.

Furthermore, among these examples, those showing a concept that chemical reaction systems such as reaction tanks, fluid control elements and detecting portions are integrated in a chip (Journal of Japan Mechanics Association 100, 615–617 (1997), Sensor/Actuator/Week 1997 General Symposium Abstracts "Microsensor" Session 3, pp. 19–23 (Apr. 17, 1997)) are also found. Furthermore, in these examples, capillaries are formed and thus glass is used as a material for making grooves on the surface.

In case silicon and glass are used as materials for chips, etching protection coats (Cr etc.) are formed in thickness of several thousand Å on a substrate made of glass, quartz or Si substrate using a technique such as vacuum evaporation, and patterning resists are applied thereon using a spinner. Then, the resist is exposed to ultraviolet light using a mask for photolithography, followed by carrying out development (removing a non-cured portion with a solvent) patterning resulting in a desired shape. Next, using the patterned resist as an etching mask, the etching protection coat is dissolved and removed with potassium ferricyanide solution and the like resulting in patterning. Next, using the patterned resist and the etching protection coat as masks, the substrate is etched with hydrofluoric acid solution, for example, to form a groove. Then, the resist and the protection coat are etched away. Also, in addition to the above described substrate, a substrate such as glass provided with through holes using a technique such as ultrasonic processing is prepared. Finally, after the substrate provided with grooves and the substrate provided with through holes are laminated with the groove being at the inner side thereof and the laminated substrates are heated, for example, in a vacuum furnace (in case both of them are glass plates, at around 600° C. for several hours), followed by leaving them to cool for fusion to produce the chip.

As described above, in case of glass, a groove must be formed on plane glass one by one to produce chips using a method as an extension of a technique for producing semiconductor integrated circuits (a combination of photolithography technique and etching technique). Also, in the process of production, many hazardous chemicals are used, and the production process takes long hours and requires expensive large equipment for use in production of semiconductors and the like. Furthermore, the above described chip made of glass has a disadvantage that it is apt to splinter and should be handled carefully.

Furthermore, for use in medical diagnosis and the like, the chip may be contacted by samples originated from patients such as blood, and it is desirable that the above described chip is made disposable, but glass material is incombustible, thus raising problems also in waste disposal. Therefore, it is not suitable for POC analyses etc. requiring inexpensiveness.

On the other hand, for medical diagnosis, the concentrations of a variety of substances in samples originated from biological bodies such as blood, urine and cerebrospinal fluid are widely detected quantitatively or qualitatively. Items to be detected in samples originated from biological bodies include the enzyme activity of GOT, GPT, γ-GTP and ALP, total cholesterol, triglyceride, glucose, hemoglobin Alc (HbAlc), and further proteins such as creatinine kinase, C reactive proteins (CRP) and cytokinins, antigens originated from bacteria and virus and antibodies against them.

Detection of these substances to be detected is performed by reacting the sample with an enzyme and antibody specific to the substance to be detected to thereby convert the substance ultimately to a substance (coloring dyes, fluorescent substances, luminescent substances, etc.) that can be detected by absorbance, fluorescence, chemical luminescence and so forth and determining the amount of the final substance (Ogawa, Z. et al., Clinical Investigation, 41:981 (1997), Kanno, T., Clinical Investigation, 42:309 (1998)).

These detection reactions are carried out by weighing a fixed amount of a sample and one kind or more of reagent solutions respectively and mixing them to implement reaction at a predetermined temperature for fixed time period.

In central laboratories of major hospitals and automatic analyzers adopted by clinical examination companies, a fixed volume or weight of samples and reagent solutions are weighed respectively with automatic pipettes. Also, in case of manual analysis, examiners weigh a fixed amount of samples and solutions using pipettes and quantitative capillaries.

Examination of contamination for food is performed in a similar way (Japanese Patent Laid-Open No. 4-64063, Method of Detecting Food Contaminating Bacteria).

In case of determining the amount of environmental pollutants, various kinds of reagents are often made to react using river water and soil extracts as samples to detect object substances (Japanese Patent Laid-Open No. 9-72898, Method of Analyzing Soils).

Methods in which these reactions for detection are carried out in the chip, that is, some reactive reagents and standard reagents are mixed with samples in the chip to implement reaction, and the post-reaction sample is analyzed include methods described below.

One of them is a method in which predetermined amounts of the sample and reagent solutions are weighed outside the chip and are then injected in the chip. Also, there is a method in which a predetermined volume of channel (reservoir) such as messcylinder is provided in the chip and delivered liquid is controlled accurately by means of combination of a pump with valves or applying electric field, thereby weighing and mixing the sample and reagent solution in the chip (for example, A. Manz et al., Trends Anal. Chem., Vol. 10, 144, 1991). Furthermore, there is a method in which the sample and reagent solution are poured into the chamber and are mixed to implement reaction, followed by weighing a fixed amount of them to separate components and analyzing quantitatively the amount of each of the separated components (S. C. Jacobson et al., Anal. Chem., Vol. 6, 4127,1994). In any of these methods, a process of weighing the sample and reagent solution or their mixture is required, and a method in which analysis is carried out while delivering liquid continuously at a constant flow rate ratio has not been proposed.

On the other hand, a concept of mixing two liquids in a predetermined ratio without weighing operations has also been proposed (U.S. Pat. No. 5,785,831 (HP), Japanese Patent Laid-Open No. 8-261986 (Japanese Patent of corresponding to U.S. Pat. No. 5,785,831)). However, the concept is to simply mix two liquids in the diverged channel, and it does not include a concept of carrying out predetermined chemical reaction continuously and using the reaction for detection of specific substances. Similarly, methods in which among two laminar flows contacting each other at a predetermined flow rate, interaction near the interface is used have also been proposed (WO 9739338, U.S. Pat. No. 5,716,852, WO 9747390). However, also in this case, it is basically means for extracting or measuring necessary molecules and particles using difference in diffusion rate due to difference in sizes of particles and molecules contained in each flow, and is not to implement predetermined chemical reaction.

Also, there are examples of carrying out necessary chemical reactions without weighing operations (J. Micromech, Microeng. 4, 246–256 (1994), Verpoorte E. M. J., //Manz A., deRooij N. F. INTERFACIAL DESIGN AND CHEMICAL SENSING, Chapter 21 pp. 244–254, America Chemical Society (1994)). That is, two or more chips made of silicon having grooves on the surface are overlaid on one another to form the capillary and reactive reagent solution is delivered by a pump to the capillary at a constant flow rate, thereby mixing the sample solution with the reactive reagent solution at a predetermined ratio and implementing reaction in the capillary.

However, in this method, the sample solution is simply mixed with the reactive reagent solution at a predetermined ratio, and for actual implementation processes, it is not substantially different from the batch system in which the sample solution and the reactive reagent solution are put in a mixing tank at a predetermined ratio.

Furthermore, in a structure like this having a plurality of chips overlaid on one another, a channel has a three-dimensional structure, thus making it difficult to go up step by step in the channel and obtain measured values at variety of reaction time. That is, quantification can be done at the endpoint of the enzyme reaction, but it is difficult to do quantification in a rate assay in which the amount of enzyme is determined from the reaction rate.

For analyzers, research and development aimed at POC analyses etc. is currently in progress, including the fact that chips comprising capillaries have been proposed. However, as described above, the material of chip comprising capillaries is generally glass and silicon to which fine processing can be applied with high accuracy. Therefore, the cost for processing is high and there are also disadvantages that the chip is apt to splinter and careful handling is required, and so on. Furthermore, for use in medical diagnosis and the like, the chip may be contacted with samples originated from patients such as blood, and it is thus desirable that the chip comprising a capillary is disposable, but glass material is incombustible thus raising problems also in waste disposal.

Also, considering an analyzer combining channel equipment and detection equipment, for a method using luminescent phenomena, light-intercepting efficiency is not high because emitted light is diverged in all directions.

Of methods using luminescent phenomena, chemical luminescent reactions have advantages of high speed and high sensitivity and of relatively inexpensive equipment because no light source is required for detection, but have disadvantages that luminescence is rapidly decayed, reagents are unstable, the background is high, and so forth.

Furthermore, in a similar way, the fluorescent method has an advantage that its reaction system has been known for a long time, but it requires as optical systems, excitation light sources and optical filters for separating excitation light from fluorescence, and so on.

Also, the fluorescent method is not suitable for the case in which a trace amount of sample in a fine capillary for use in the present invention is detected because the yield of emitting fluorescence is low and so on.

Also, the absorptiometric method has a disadvantage that it is necessary to make the length of optical path large so as to obtain accurate results and particularly long optical path is obtained for detecting a trace amount of samples, thereby making the structure of detection cells complicated, because the ratio of the incident light to the transmitted light is detected in principle.

In this way, for analyzers detecting a trace amount of sample in the fine capillary for use in the present invention, those that are easy for handling and economical, and are capable of performing analysis of high sensitivity, and can be downsized are not available, and analyzers suitable for POC analyses etc. are desired in the present circumstances.

On the other hand, detecting paper that enables the value of blood sugar and the like to be detected by dissolving solid reagents (freeze-dried reagents or paper and fiber impregnated with a predetermined amount of reagents) in the sample using only plasma are on the market. These solid reagents are convenient because it is not necessary to weigh reagents, but have a disadvantage that they are poor in quantitative accuracy compared to liquid reagents.

Furthermore, methods in which the sample and reagent are weighed outside the chip and are injected into the chip thereafter to implement reaction for detection not only require much manpower but also produce wastes in addition to wastes of chips. Also, in case man does not weigh the sample and reagent, a weighing system is required in addition to the chip, thus leading to large scale equipment as a whole. Furthermore, it is necessary to provide a channel in the chip for weighing the sample and reagent, thereby making the channel in the chip more complicated and leading to high costs. Also, these methods have a disadvantage that introduction of the operation of weighing the sample and reagent causes the process of analysis to be more complicated without distinction of inner and outer sides of the chip. Furthermore, the prior art requires additional means for adjusting timing for each process that is continuous and needs to control time accurately, because of the batch-type sample process and detection.

DISCLOSURE OF THE INVENTION

An analyzer of the present invention consists of a chip comprising a capillary, which is easy for handling, capable of having a complicated structure and excellent in safety, disposability and mass-producibility, and detection equipment that is easily downsized and is able to detect a trace amount of components with high sensitivity. Then, an object is to provide an analyzer that is excellent in operability, compact and inexpensive, wherein predetermined mixing and chemical reaction are performed only in the capillary of the chip without weighing samples and reagents and so on separately, and it is not necessary to adjust timing delicately for each process across all processes.

The present invention uses at least in part an organic polymer, as material of the chip comprising the capillary in which a fluid flows. The chip made of organic polymer that is molded with good accuracy of size is suitable for micro analysis, can be produced inexpensively, and can easily be disposed by incineration, and is thus useful as a disposable chip. Furthermore, the chip is easy for handling, capable of having a complicated structure, and is excellent in safety and mass-producibility.

Also, in this applied invention, the flow rate of a fluid-like sample and fluid-like reagents in the capillary formed in the chip made of organic polymer are controlled at predetermined values respectively, and these fluids are flowed continuously, thus merging the fluid-like sample with the fluid-like reagent at a predetermined ratio of flow rate. After merger, the capillary having length necessary and sufficient for allowing the fluids to flow for a time period required for mixing and reaction in a predetermined flow rate is provided to perform predetermined operations such as mixing, dilution and chemical reaction. By this means, predetermined operations such as mixing and dilution of a plurality of fluids can be performed without carrying out weighing (without distinction of inner and outer sides of the chip), allowing the necessary chemical reaction to be implemented accurately and simply, without requiring delicate adjustment of timing for each process across all processes.

Also, when the post-reaction product produced by the above described means is irradiated with excitation light focused by an objective lens and the like, change in physical quantity accompanying partial change in temperature (photothermal effect) due to excitation and absorption, more specifically change in refractive index occurs. With this analyzer comprising detection equipment (thermal lens detection equipment) that measures this change in refractive index using detection light and the like irradiated in addition to the excitation light, it has been possible to measure the concentration of substances to be detected and the like that was difficult to measure with prior arts because of the length of the optical path being as small as vertical width of the chip (the angle is not necessarily a right angle to the chip surface), namely as small as the depth of a groove (about 1 to 1000 $\mu$M).

However, the thermal lens detection method conventionally used is a general-purpose method of detecting substances in micro spaces, but in this method, in order to improve absolute sensitivity of how many molecules can be detected at minimum, the excitation light is focused wherever possible by the objective lens and the like and is converged in the sample solution, thus reducing the thickness of the thermal lens to be formed.

For example, in one of conventional thermal lens detection methods, "Development of Integrated Liquid Phase Chemical Analysis System Using Micro Channel on Glass Substrate and Thermal Lens Microspectrometry (I)" (Japan Analytical Chemistry, Abstracts of 44th Annual Meeting, p. 119, 1995) by Kawanishi et al., it is described that the beam diameter of excitation light near the focus is reduced to about 4 $\mu$m by setting the magnification of a microscope to 70 times, and the beam diameter of excitation light can be further reduced to the order of sub-micron by setting the magnification of a microscope to 280 times. However, in these conventional thermal lens detection methods, concentration sensitivity of determining the amount of substances in a certain volume of the sample solution is low.

For medical diagnosis and environmental analysis, it is important that the concentration sensitivity, not absolute sensitivity, is high. Then, the inventors of the present invention and so on have found that the concentration sensitivity is increased by reducing the condensed degree of excitation light and enlarging the thermal lens to approximately the cross-sectional area of the channel in contrast to conventional thermal lens detection methods, thus making it possible to detect substances with high sensitivity even in a capillary having a small cross-sectional area that allows a stable electroosmotic flow.

Also, when the chip made of organic polymer comprising a capillary was applied to the above described thermal lens detection equipment, the background signal of output in the thermal lens detection method was increased depending on materials of chips. In case of glass material that has been used conventionally, glasses of which transmittance excluding reflected laser for use in the thermal lens detection method (for example, He—Ne laser (wavelength: 633 nm), Ar laser (wavelength: 488 nm), semiconductor laser (for example, wavelength: 780 nm)) is not lower than 99% or almost equal to 100% are easily obtained as normally available commercial items. Thus, problems have not been raised in implementing the thermal lens detection method.

However, concerning the organic polymer, normally available commercial items contain additives, plasticizers, stabilizers and the like, and those having high transmittance as glass are not generally available. Therefore, it has been found that base materials made of organic polymer applicable to the thermal lens detection equipment are limited. In particular, it is absorption of the excitation light and the like in the optical path of the excitation light and the like that has strong influence on the thermal lens detection equipment. Then, an acceptable range of the absorption amount has been acquired by experiments.

That is, the analyzer relating to the present invention is an analyzer for flowing fluid-like samples or fluid-like samples and fluid-like reagents in a capillary to analyze predetermined components in the above described samples or the mixed fluid of the above described samples and the above described reagents, characterized in that the analyzer consists of a chip configured at least partially by organic polymer and comprising the above described capillary and photothermal detection equipment for irradiating the above described predetermined components with an excitation light to measure change in physical quantity accompanying the resultant partial change in temperature in the above described capillary.

Furthermore, the fluid in the present invention means substances having fluidity, in addition to liquid and gas.

Also, as for the fluid-like sample to be flowed in the capillary, only the sample may be flowed, and the sample may be mixed with a fluid-like carrier to be flowed or the sample may be mixed with a fluid-like reagent to be flowed as long as the mixed product is a fluid.

They may be mixed before they are supplied to the capillary, or each of them may be supplied to the capillary individually and then mixed in the capillary.

The above described chip can be constituted by laminating a pair of plane plate members at least one of which comprises grooves on the plane surface and at least one of which is made of organic polymer, with the above described plane surface comprising grooves being at inner side thereof.

Furthermore, for a pair of the above described members, both of them may be made of organic polymer, or only one of them may be made of organic polymer. However it is desirable that the above described plane plate member which comprises grooves is made of organic polymer.

Also, considering the above described change in physical quantity as change in refractive index, the above described photothermal detection equipment may be an equipment for letting detection light in a thermal lens formed by the above described change in refractive index to measure the change in the above described detection light caused by the above described thermal lens.

It is desirable that the member constituting the above described chip does not cause the substantial effect of photothermal effect by absorbing the above described excitation light.

For example, it is desirable that the member constituting the above described chip has absorptance of the above described excitation light being 5% or less.

Furthermore, it is desirable that the condensed degree of the above described excitation light is already adjusted so that the partial change in temperature in the above described capillary occurs in a range in which concentration sensitivity sufficient for analyzing the above described predetermined components can be obtained.

However, more preferably, the optical axis of the above described excitation light is perpendicular to the direction of flow of the above described sample and the above described mixed fluid, and the condensed degree of the above described excitation light is already adjusted so that the partial change in temperature in the above described capillary occurs in a range in which concentration sensitivity sufficient for analyzing the above described predetermined components can be obtained, in a cross section perpendicular to the above described direction of flow and including the above described optical axis.

Furthermore, the optical axis of the above described excitation light may be oblique to the direction of flow of the above described sample and the above described mixed fluid.

Furthermore, the condensed degree of the above described excitation light can be adjusted using the numerical aperture of an objective lens irradiating the above described capillary with the above described excitation light.

Furthermore, the above described capillary of the analyzer relating to the present invention may be a configuration having sample channels for flowing the above described sample and channels for performing the above described measurement, and in addition thereto, having at least one reagent mixing means between the above described sample channels and the channels for performing the above described measurement;

wherein the above described reagent mixing means consists of at least one reagent channel for flowing the above described reagent, a confluence of the fluid flowing from the above described sample channel side and the regent flowing from the above described reagent channel, and a mixing channel placed downstream of this confluence for mixing the fluid flowing from the above described sample channel side and the regent flowing from the above described reagent channel at a predetermined flow ratio to carry out reaction for a predetermined time period, in case the number of the above described reagent mixing means is two or more, each reagent mixing means is arranged in series, and a flow rate adjusting mechanism for adjusting the flow rate in the above described sample channel and the above described reagent channel in accordance with the above described mixing ratio is comprised.

In case of such a configuration, the above described sample and the above described reagent are flowed continuously in the above described capillary, and the above described mixing channel may be a channel with length enough for the fluid merged just before its confluence to flow for a time period required for completing predetermined mixing and reaction under a predetermined flow rate.

Furthermore, the above described sample or the above described sample and reagent can be flowed by applying a voltage to the above described sample or applying a voltage to the above described sample and reagent individually.

Furthermore, the above described sample may be a sample originated from biological material.

Furthermore, in case the above described chip is constituted by a pair of the above described plane plate members, one of a pair of the plane plate members may be a plane plate member made of organic polymer, which is molded using one of a compression molding method, an embossing molding method, an injection molding method, an injection molding method in which a glass transition temperature of a resin is lowered in the presence of gas, injection compression molding and injection molding using mold surface heating by electromagnetic induction or a combination thereof.

In this case, the gas used in the above described injection molding method in which the glass transition temperature of a resin is lowered in the presence of gas may be carbon dioxide.

Thus, the analyzer relating to the present invention detects a predetermined component with the photothermal detection method using a detection system of photothermal detection equipment after making predetermined mixing and reaction occur, without weighing the sample and reagent in the chip. By using the photothermal detection method as a detection method, a trace amount of predetermined component can be detected with high sensitivity. Furthermore, since it is not necessary to perform weighing without distinction of inner and outer sides of the chip, not only excellent operability but also the downsize of equipment can be achieved.

BRIEF DESCRIPTION OF THE DRAWINGS

FIG. 15 is a table showing results of measuring the absorptance of laser beam of polymer base materials and the output in the thermal lens detection method;

BEST MODE FOR CARRYING OUT THE INVENTION

Figure 1:
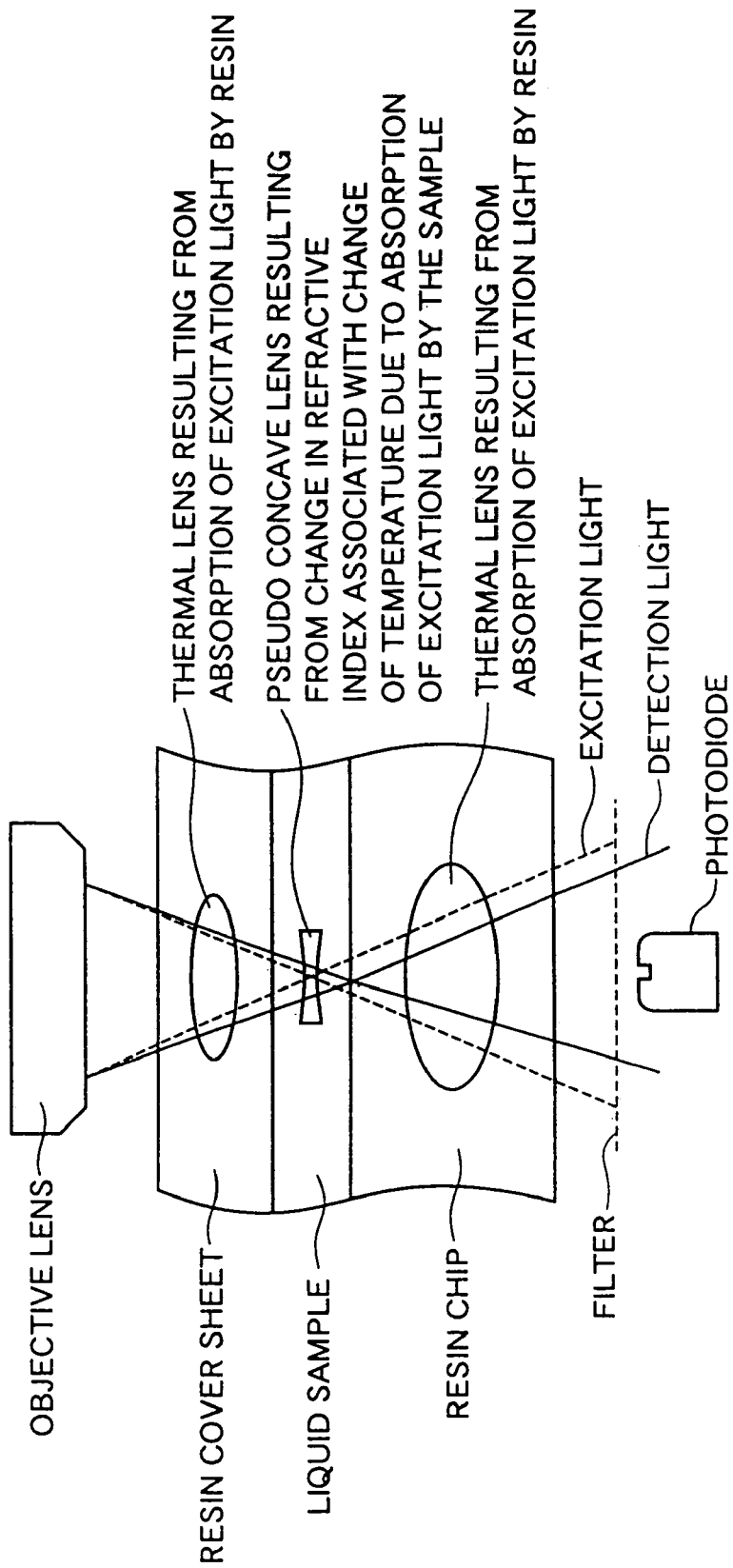
FIG. 1 is a schematic diagram of a thermal lens detecting portion of an analyzer based on a photothermal detection method according to the present invention.

An analyzer relating to the present invention consists of a chip comprising a capillary and detection equipment.

The chip consists of a pair of plane plate members made of polymer, and grooves in which fluids flow are made on the surface of at least one of the members. These plane plate members are laminated with each other with the groove being at the inner side thereof to form the capillary. This capillary has a channel for a sample and a channel for at least one kind of reagent solution, and also has a merging point at which such channels merge in succession or at a time. Furthermore, this capillary has at the downstream side of the merging point a channel of predetermined length or larger required for mixing and chemical reaction of the above described sample and the above described reagent solution, and also has a structure in which the channel is coupled to a channel for performing measurement. Since these samples and reagent solution need to be controlled so that they are delivered at a predetermined flow rate, the above described analyzer has an arrangement for this requirement. That is, the arrangement in which the above described sample and the above described reagent solution flow in the capillary at a predetermined flow rate.

Then, the detection equipment comprises a mechanism for irradiating excitation light and detection light, and consists of an optical detection system based on a photothermal detection method (for example, Analys is No. 4, 280–284 (1997)).

(Polymer Chips)

In the present invention, the shape of cross section of the groove formed on the surface of the plane plate member includes polygonal shapes such as quadrangle and triangles, semicircles and semi-ellipses, and is not particularly limited. Also, the chip may have on the surface a channel constituted by combination of several kinds of grooves of different shapes. The width of the upper face (open face) of the groove may be same as or larger than that of the lower face (bottom) of the groove. Furthermore, in order to implement detecting means based on the photothermal method described below more simply and accurately, it is desirable that the shape of the cross section of the groove is quadrangle.

If this groove is too small, the flow may be disturbed by fine particles. Also, if it is too large, not only the area of the plane plate member must be enlarged when many channels are made on the surface of one plane plate member, but also problem arises in terms of the diffusion distance when mixing by diffusion is performed. Thus, preferably, the width of the groove is 1 to 1000 μm, the depth is 0.1 to 1000 μm, and the cross-sectional area is 1 to 1000000 μm². More preferably, the width of the groove is 2 to 500 μm, the depth is 1 to 500 μm, and the cross-sectional area is 2 to 250000 μm², and furthermore preferably, the width of the groove is 2 to 200 μm, the depth is 1 to 200 μm, and the cross-sectional area is 2 to 40000 μm².

For the plane plate member made of organic polymer of the present invention, the accuracy of dimension of the groove that the member has on its surface is not particularly limited. However, in performing analysis of ultra-micro components and quantitative analysis, accuracy of dimension is preferably good. That is, in order to achieve operational accuracy and reproducibility among individual analyzers, the accuracy of dimension of the groove preferably has accuracy of dimension (dimensional accuracy of transfer) within ±5% in width and depth and within ±7% in cross-sectional area for the convex shape of the mold (transferred by molding, with grooves being formed in case of the plane plate member). For performing quantitative analysis with high accuracy, further more preferably, it has accuracy of dimension within ±2% in width and depth and within ±4% in cross-section.

The chip comprising the capillary of the present invention is made by laminating two plane plate members at least one of which has on the surface the groove in which the fluid flows with the above described groove being at the inner side thereof, using supersonic fusion, thermal fusion, adhesion with adhesives such as hot-melt adhesives and UV adhesives, tacky adhesion with sticking agent, press-contact performed directly or via a thin elastic sheet and the like. In any case, preferably, a vacuum laminator allowing crimping to be carried out in a vacuum system is used, and methods in which crimping is carried out from the center toward the peripheral while expelling bubble and soon are used, in order to prevent bubble being trapped during lamination.

As the plane plate member having no grooves (hereinafter referred to as "covering plate"), plane plate sheets made of resin such as methacrylic resin, polycarbonate and polystyrene or glass sheets (thin glass plate) and the like may be used. The thickness of these sheets is not particularly limited unless there is a problem with photothermal analysis described below such as problems of light absorption and the like, but it is preferably in a range of 0.05 to several mm.

Also, the chip has an opening for introducing the sample or reagent and installing an electrode in one of the two plane plate members to be laminated, as a through hole. It is desirable that the through hole is provided at the end of each channel of the plane plate member or is provided in the portion of the other plane plate member to be laminated, which is merged with the above described end of each channel. The size of the through hole is not particularly limited, but the diameter of the opening is preferably in a range of 0.1 to several mm.

Molding processability is an important element in selecting the material of organic polymer base used in the plane plate member having grooves. Materials that can be favorably used in terms of molding processability include transparent thermoplastic resins to which general melting process can be applied and transparent resins obtained by UV curing and heat curing. Furthermore, the former is more favorable in that the plane plate member having grooves on the surface can be fabricated in large quantity and inexpensively. Of these resins, non-crystalline thermoplastic resins, thermoplastic polymer alloys having non-crystalline resin as a main component, or a part of crystalline thermoplastic resins having low crystallinity are favorable. Resins that can be used particularly favorably are rigid resins, including specifically styrene-type resins such as polystyrene and styrene-acrylonitrile copolymers, methacrylic resins such as polymethyl methacrylate (PMMA) and methyl methacrylate-styrene copolymers, polycarbonate (PC), polysulfone, polyether sulfone, polyetherimide, polyarylate, polymethyl pentene, polyvinyl chloride, polycyclohexadiene and polyester.

Also, 1,3-cyclohexadiene type polymers are favorably used. 1,3-cyclohexadien type polymers can use homopolymers, but may also use copolymers. These copolymers include copolymers with conjugated diene type aliphatic monomers such as 1,3-butadiene, isoprene, 1,3-pentadiene and 1,3-hexadiene, aromatic vinyl monomers such as styrene, α-methyl styrene, p-methyl styrene, 1,3-dimethyl styrene, vinyl naphthalene and vinyl styrene, polar vinyl monomers such as methyl methacrylate, methyl acrylate, acrylonitrile, methyl vinyl ketone and methyl α-cyanoacrylate or polar monomers such as ethylene oxide, propylene oxide, cyclic lactone, cyclic lactam and cyclic siloxane, or ethylene and α-olefin type monomers. The ratio of copolymerization in this case is preferably 1,3-cyclohexadiene monomer/comonomer=75/25 to 100/0 in weight. Cycrohexadiene type polymers of high light transmittance are described in detail in the Japanese Patent Application No. 9-277045. Such polymers can also be detected with a light source of short wavelength since they have little absorption of wavelength of 200 nm or larger as materials and they are amorphous C—H polymers.

For chips of the present invention that are made of these polymer bases, a pair of plane plate members configuring the chip both consist of materials that allow detection light to go through, and at least one of both plane plate members consists of a material that allows excitation light to go through. The analyzer of the present invention consists of such a chip and photothermal conversion detection equipment, thereby making it possible to detect with high sensitivity even detection object substances having absorption only in ultraviolet region, which is difficult to measure with an analyzer using conventional resin chips, and its general versatility is high. This fact is very important for use in analysis for medical diagnosis because many of biological substances have absorption only in the ultraviolet region (that is, those colorless to human eyes).

Now, a few additional explanations will be presented about analysis of substances having absorption only in the ultraviolet region. The organic polymer (resin) is superior to glass as a chip material in terms of producibility, costs and waste disposal. However, the organic polymer generally has absorption in the ultraviolet region. Thus, detecting an object substance using the absorptiometric method that is a general detection method, the absorption by the chip material is so large that a correct measured value cannot be obtained. Furthermore, with optical path length of 100 µm or so, it is difficult to detect a trace amount of component even though a wavelength that the chip material does not absorb is used. Detection can be performed with fluorescence, but detection object substances are limited to substances emitting fluorescence, leading to deterioration in general versatility.

By contrast, in the photothermal conversion detection method, the wavelength of the detection light can be freely selected from wavelengths that the organic substance does not absorb, as long as the excitation light is absorbed in the object substance. In the chip consisting of a pair of plane plate members, if both plane plate members are "transparent" to the detection light of a wavelength not absorbed by the organic polymer (usually visible light), and one of a pair of plane plate members has transmittance allowing sufficient excitation light to go through so that the object substance is excited, general-purpose measurement can be made. As a specific example, the case where the thickness of the plane plate member having grooves is in a range of about 1 to 5 mm, the plane plate member (covering plate) to be laminated with the plane plate member having grooves is a thin sheet with thickness of about 500 µm or less, and this sheet consists of a material having high transmittance for the excitation light. In this case, the excitation light is applied from the thin sheet side, thereby making it possible to detect the detection object substance with high sensitivity even though the plane plate member having grooves has low transmittance to the excitation light.

The organic polymer for use in the present invention needs to be a resin having transparence to the light of wavelengths for use in the photothermal method. Considering the power loss of laser, those having transmittance of 80% or higher, preferably 90% or higher at wavelengths of excitation and detection laser used in the photothermal detection are desired. Considering the wavelength of excitation and detection laser, generally, those having light transmittance of 80% or higher, preferably 90% or higher are desired when measured in a range of wavelength of 600 nm to 800 nm, preferably of 400 nm to 800 nm in accordance with ASTM D1003.

The aforesaid light transmittance is the value obtained by subtracting the sum of reflectivity on the surface of the chip and absorptance by the organic polymer base itself from 100%. Light scattered on the surface of the chip and the like has no effect on the organic polymer, while light absorbed by the organic polymer base has the effect of causing the organic polymer to generate heat. Therefore, an effect like thermal lens is produced when the light goes through the organic polymer, which leads to a background to the output in the thermal lens detection method, thus causing an error in measurement. Thus, it is necessary to evaluate the organic polymer material before making an actual chip and determine the range of absorptance having no influence on the actual thermal lens detection method.

In case of detection with absorbance, if about 10% is absorbed by the organic polymer, total quantity of light is only reduced to 90%, having little influence on the detection sensitivity. However, in case of the photothermal detection method, even 10% or less of absorption has significant influence on measurement due to the thermal lens formed in the resin.

In view of the measurements shown in the examples described below, in case the analyzer with thermal lenses of this application is applied for uses intended to perform quantitative measurement, it has been proved that percentage of excitation light absorbed by the organic polymer in whole optical path in which the excitation light passes through the chip needs to be 5% or less.

However, in case high sensitivity is required for measurement, such as the case where the concentration of the measuring object is low and the capillary is thin (the groove is shallow), even a slight amount of absorption may cause a background that has negative influence on the measurement of substances in the capillary.

In case the measuring object is a component in the blood and a reagent kit currently sold is used as reagents, measurement in which absorbance for 1 cm cuvette is about 0.1 is often carried out. Assuming that this measurement is carried out using a chip made of organic polymer of the present invention, which comprises a 50 µm capillary (that is, the optical path length is 50 µm), absorbance of 0.1 for 1 cm of optical path length is the equivalent of 0.103% of absorptance for the 50 µm capillary. Absorptance would be 1% if the absorption by the chip made of organic polymer (formation of the thermal lens) is accepted by up to 10 times, and absorptance would be 0.2% if the absorption is accepted by up to 2 times.

That is, to carry out measurement in which the absorbance for 1 cm of optical path length is about 0.1 using the analyzer of the present invention, it is desirable that light absorption by the organic polymer forming the chip is 1% or less, more preferably 0.2% or less.

However, these values may be changed depending on modification of reagent kits and difference in the depth of capillaries. For example, increasing absorbance for the 1 cm cuvette to about 0.5 is not so difficult with current technologies. In this case, absorptance for the 50 µm capillary is the equivalent of 0.342%, and the absorptance would be about 3.5% if the absorption by the chip made of organic polymer (formation of the thermal lens) is accepted by up to 10 times, and the absorptance would be slightly smaller than 1% if the absorption is accepted by up to 2 times.

Also, as for detection light, for fear of resulting in change of its own optical path due to absorption, it is desirable that similarly, the percentage of the light being absorbed by the organic polymer in entire optical path in which the light passes through the chip is made to be several percent or less.

In this way, it has been proved that a material configuring the chip should be appropriately selected in case analysis and measurement are carried out using the thermal lens detection method. In case of either excitation light or detection light, the accepted absorptance by the polymer base changes depending on the concentration or absorbance of measuring objects. Thus, the absorption of the excitation light and detection light by the material comprising the chip should be such a level that measurement by the thermal lens detection method is not substantially influenced. Taking a biochemical reaction system as an example, it is desirable that the absorptance by the polymer base is several percent or less.

The plane plate member consisting of the organic polymer selected on the basis of the aforesaid criteria may be made by methods such as cutting process and etching process with laser and the like, UV curing and heat curing of monomers and/or macro monomers in the mold, and melting process and plastic process of thermoplastic resin. Molding methods that can be used favorably are the melting process and plastic process of thermoplastic resin in that the plane plate member having grooves on the surface can be molded in large quantity and inexpensively. Methods that can be further favorably used are the injection molding of thermoplastic resin using molds and/or the compression molding method and the emboss molding method. The injection molding method including injection compression molding is a molding method that is excellent in mass-producibility and economy. Compression molding is inferior in mass-producibility to the injection molding, but allows the mold surface to be formed with good transferability. Specifically, thermoplastic resin that is molded in plate-like shape in advance is put into the mold, and the thermoplastic resin is then heated up to the softening temperature by a heat press. Then, pressuring compression (pressing) is carried out and the mold surface is transferred, followed by allowing the heat press to cool under a pressurized condition and cooling and solidifying the thermoplastic resin at a softening temperature or lower. Particularly, the injection molding method in which injection molding is carried out while lowering the solidification temperature of the surface of resin contacting the mold during process of filling resin in the mold cavity (Japanese Patent Laid-Open No. 10-128783, Japanese Patent Application No. 10-50719) may be an especially preferable molding method because plane plate members made of organic polymer having fine grooves of high moldability can be fabricated with good producibility. Specific examples of this injection molding method include methods in which carbon dioxide is filled in the cavity before injection molding is carried out. The pressure of carbon dioxide is preferably 10 MPa or lower, and further preferably 0.3 to 2 MPa, considering a compromise between the prevention of gas from being trapped and the effect of lowering the solidification temperature of the surface of resin.

Also, injection molding methods in which the surface of the mold is heated to carry out molding such as injection molding methods in which the surface of the mold is heated with high-frequency induction heating immediately before molding (described in Japanese Patent Publication No. 62-58287, U.S. Pat. No. 4,439,492) and injection molding methods in which the surface of the mold is heated with radiation heating immediately before molding (described in Molding Symposia 1995, 241 <1995>, Molding 1996, 69 <1996>, Synthetic Resin, Vol. 42 (1), 48 <1992> and the like) are methods preferable for production of the plane plate member made of organic polymer of the present invention. This is because the above described molding methods are methods in which the mold temperature is set low and only the surface of the mold is selectively heated immediately before molding with a heat source such as high-frequency induction heating and halogen lamp, thus making it possible to achieve compatibility between the transferability of mold surface and the molding cycle time.

The plane plate member made of organic polymer of the present invention can also be produced based on Method of Producing Circuit Board of Japanese Patent Laid-Open No. 6-283830. According to this method, directions of scattered particles are better oriented in the vertical direction with thick resists than with usual thin resists, thereby enabling sharper molding to make grooves of high aspect ratio. Furthermore, a method in which a resin substrate is coated with photosensitive resists and portions other than grooves are exposed to light, followed by removing uncured portions to form groove-shaped resist patterns on the substrate can also be implemented.

As for molds, metal molds composed of iron or steel materials containing iron as a main component, aluminum or alloys containing aluminum as a main component, zinc alloys, beryllium-copper alloys, nickel or the like, which are generally used for molding of synthetic resin can be favorably used.

One example of mold fabrication methods will be presented. First, one matrix having a surface shape of the plane plate member made of organic polymer having desired fine grooves is fabricated from a material such as metal, plastic, silicon or glass, with a method such as cutting process and etching process, or photolithography process of ultraviolet cured resin. Then, a mold is fabricated from this matrix using electrochemical casting of nickel and the like.

Also, the mold can be fabricated using the above described method of forming resist patterns in Japanese Patent Laid-Open No. 6-283830. A resist pattern is formed on a metal substrate, followed by filling the portion having no resist by metal plating. Then, the resist is removed to form a metal plate having a fine pattern formed on the surface of the substrate. Using this plate as a mold, resin can be processed.

Also, for the chip constituted by the plane plate member made of organic polymer of the present invention, protein adsorption inhibiting treatment can be applied to the inner surface of the capillary by graft polymerization of polyethylene glycol and the like. Also, in case an electroosmotic flow described below is used as liquid delivering means, the surface of the capillary may be treated with sodium hydroxide solution so as to generate a stable electroosmotic flow. When PMMA is used as an organic polymer, in particular, treating with sodium hydroxide causes ester on the surface to undergo hydrolysis to expose carboxylic acids, thereby making the electroosmotic flow enlarged and stabilized, which is preferable.

Also, when the electroosmotic flow (EOF) described below is used as liquid delivering means, the chip may have on its surface a metal electrode composed of metal needles, metal plates, metal foils and the like, an electrode made of inorganic or organic polymer to which conductivity-adding treatment has been applied, or an electrode printed with conductive ink. In this case, it is preferable that an electrode contacting reservoirs (in to which reagents, samples, buffers, waste liquid, etc. are put) placed in the capillary and at the end or at some midpoint of the capillary, an electrode that can be connected with the detection equipment and leads between the electrodes are also comprised in the chip.

In case the metal needle is inserted, a nail, a needle, an eyelet matter or the like composed of platinum, copper, brass, aluminum, iron or the like, which has a diameter of 0.1 to 2.5 mm and length for reaching near the groove of the plane plate member is preferably fixed in the through-hole.

In case of printing with conductive ink, the electrode may be formed by for example screen printing using ink containing fine particles of gold, silver, copper, nickel, carbon black, graphite and so on. For printing the inner wall of the through-hole by screen printing, through-hole printing technology with conductive ink by a screen printer, which is implemented to be continuity each layer of the current multi-layered print board may be applied. The through-hole printing is performed by placing a sample to be printed on a sample stage with the through-hole of the sample being aligned with a suction hole of the sample stage, and sucking the ink trapped in the periphery of the through-hole to make the ink creep on the inner wall of the through-hole while or after printing the sample.

Vacuum deposition and sputtering, in case of either the whole or part of inner wall of the through-hole, gold or platinum is deposited or printed deeply enough to reach near the groove of the plane plate member. In this case, if the through-hole is shaped into taper, an electrode can be formed on the inner wall of the through-hole without causing the plane plate member to tilt.

Also, in addition to the above described electrodes, electrodes to be connected with a power terminal in the detection equipment equipped with the chip and leads between those electrodes can be formed using conductive ink, vacuum deposition and sputter coating. Also, they may be formed by sticking a thin plate such as a copper plate and then forming a wiring pattern by etching, and transferring or sticking on the plate a copper foil, etc. on which a pattern is formed.

Also, by forming electrodes and/or wiring on a third plane plate member and a fabricated item other than the plane plate member having grooves and the plane plate member to be laminated with it (covering plate) using a method as described above, and then laminating this third plane plate member and fabricated item therewith, the equipment equipped with electrodes and/or wiring can be provided.

In any case, the material and size should be selected so that heat generated when high voltage is applied can be controlled to have no influence on the electrophoresis.

(Fluids)

Fluids that the present invention targets for analysis are principally liquids and gases, and especially aqueous solutions of all. Organic solvents and gaseous substances can be treated, but in any case, they should not exert corrosiveness, solubility, whitening of resin and the like on chip materials and adhesives. In case of electrical liquid delivery, aqueous solutions are particularly preferable targets.

(Thermal Lenses)

In the chip of the analyzer relating to the present invention, the sample has its flow rate controlled accurately by the electroosmotic flow, electrophoresis or other appropriate means. Then, after the sample is diluted and reacts with other reagents as necessary, the object substance is detected at the downstream of its channel using methods described below.

FIG. 1 shows the principle of the detection method using the thermal lens formed based on the photothermal effect. When the sample is irradiated with the laser beam (excitation light) condensed through lens, heat is generated by the excitation light from the measuring object contained in the sample (photothermal effect), the refractive index of the vicinity of the focal point of the laser is decreased due to the heat. Then, spatial distribution of the refractive index is formed due to effects such as thermal diffusion. Light passing through this area does not travel in a straight line due to the distribution of the refractive index, but causes same optical effects as those caused by lens. These effects of the virtual lens are called thermal lens effects. For example, in case of substances such as water whose temperature coefficient of the refractive index is negative near room temperature, same effects as those caused by the concave lens are given. The strength of lens effects (degree of lens) is proportional to the amount of generated heat, namely the number of excited molecules. Then, when another laser beam for detection (detection light) is let in, the detection laser beam expands and contracts due to lens effects compared to the original optical path. From the magnitude of this change of the detection laser beam, the amount of generated heat, or the amount of absorbed light by the measuring object can be measured, and quantification of the measuring object is possible. In principle, since the thermal lens is formed near the focal point of the excitation laser beam, it does not require a long optical path and is suitable for detection of the samples in micro areas.

By providing thermal lens detection equipment with this analyzer, it has been possible to measure the concentration of substances to be detected and the like that was difficult to measure with prior arts because of the length of the optical path being as small as vertical width of the chip surface (the angle is not necessarily a right angle to the chip surface), namely as small as the depth of a groove (about 1 to 1000 µm).

As described previously, the width and depth of the groove of the plane plate member made of organic polymer are about 1 to 1000 µm, and therefore the optical path length in the direction vertical to the plate surface (the angle is not necessarily a right angle to the chip surface), namely in the direction vertical or oblique to the flow of the fluid is as small as the depth of the groove. However, using the thermal lens detection method, the object substance can be detected with adequate sensitivity even with this level of optical path length. Thus, since the photothermal detection method does not require complicated channel structures to provide a long optical path, the cost of the chip can be reduced. Also, detection can be carried out using compact, inexpensive and simple optical detection equipment such as a combination of semiconductor laser and photodiode. However, as for the material of the chip to be used for detection, there is a requirement that absorptance for the excitation light be small. Otherwise, as shown in FIG. 1, an area corresponding to the thermal lens is created in addition to the thermal lens for essential detection of concentration, thereby causing an error.

As detection equipment using the photothermal detection method, an excitation light source having a wavelength that the detection object substance absorbs and having adequate output for forming the thermal lens is needed. The excitation light may be light of a needed wavelength, which is taken from a xenon lamp using a prism, or a laser having a wavelength capable of exciting the detection object substance. As lasers, He—Ne lasers, Ar lasers, carbon dioxide lasers, YAG lasers and the like are used, but using semiconductor lasers allows the detection equipment to be compact, which is suitable for use in POC analyses etc. and environmental measurements. The source of the detection light may have an output smaller than that of the excitation light, and its wavelength may be identical to or different from that of the excitation light. Preferably, both the excitation light and detection light come into focuses in the capillary channel or near the capillary, and condenser lenses are required in that case.

The excitation light is made by a chopper and the like to be pulse light of about 0.1 to 10 ms. Then, the detection light captured by a photodiode, CCD camera, photomultiplier and the like is subjected to signal processing by a lock-in amplifier synchronizing with the above described chopper and the like, and its only changed portion caused by the thermal lens is taken out. Furthermore, for detection of the detection light, use of photodiodes is suitable in terms of downsized equipment.

The lock-in amplifier can be simplified with simple-functional semiconductor elements. Also, for pulsing of the excitation light, the semiconductor laser may be modulated electrically. Also, when detecting the detection light, the lock-in amplifier is generally used, but the luminous flux near the axes of the excitation light and detection light may be shielded with a screening plate using the method of a dark field type photothermal spectral analyzer disclosed in Japanese Patent-Laid-Open No. 9-229883, thus detecting only the detection light emitted by the thermal lens. Alternatively, it may be replaced with an LSI etc. concentrating functionality for the pulses of the excitation light.

Also, in the present invention, absolute sensitivity involving the counting of the number of molecules in micro spaces is not required, but it is only necessary that the concentration of a substance in the capillary can be measured with high sensitivity. That is, high concentration sensitivity is required. In other words, the thermal lens should be spread over an entire predetermined cross section of the capillary wherever possible, so that the number of molecules of the measuring object substance existing therein is increased and the effect of the thermal lens is enhanced.

Furthermore, the predetermined cross section is a cross section by the flat face including the optical axis among plane faces perpendicular to the plane face including the flow direction of the fluid in the capillary and the above described optical axis of the excitation light. Furthermore, this optical axis is preferably perpendicular to, but may be oblique to the flow direction of the fluid in the capillary.

However, the quantity of light per unit of volume is decreased and the effect of the thermal lens is reduced due to the influence of thermal diffusion and the like if the excitation is too much spread, and thus there is an optimal value for the width of the excitation light. In case of the present example 1, an objective lens of NA=0.4 is used for 50 µm of depth of the capillary and the beam diameter of the excitation light (13.5% for the maximum quantity of light) at the center of the direction of depth of the capillary 38 µm, providing the maximum value of output with the thermal lens detection method. If the thermal lens widened, then a thermal lens is formed also in the chip made of organic polymer, thereby causing a background and reducing the measurement sensitivity apparently as described before.

In this way, the thermal lens should be formed in a part of the above described predetermined cross section such that the concentration sensitivity of a predetermined component is sensitivity sufficient for analyzing the above described predetermined component. For this purpose, the excitation light should be adjusted to have an appropriate condensed degree of the excitation light and come into a focus at an appropriate position.

There are a variety of methods for adjusting the scale of this thermal lens (range in which change in temperature occurs), but it may also be achieved by adjusting the numerical aperture of the objective lens through which the capillary is irradiated with excitation light. When a normal lens, for example a microscopic lens system described in Japan Analytical Chemical Association 44th Meeting (1995) Abstracts IC05 was used directly for the chip relating to the present invention, the detection sensitivity of an object substance was not necessarily high. The size of the capillary of the detecting portion for the thermal lens is preferably approximately 20 µm or larger in both width and depth. On the other hand, it is described that in the microscopic thermal lens described before, about 4 µm of the beam diameter of the excitation light is achieved with a magnification of 70 times, and further the magnification of the microscope is increased and the beam diameter is reduced to the order of sub-microns in order to enhance the absolute sensitivity. The inventors, measured the output with the thermal lens detection method with excitation light having a beam diameter of about 4 µm, using a chip with the size of capillary of the detecting portion being 50 µm in depth and 50 µm in width, and the detection sensitivity was found to be low.

Then, the numerical aperture was reduced to about 0.1 to increase the beam diameter to about 50 µm as a result of experiments considering a variety of numerical aperture of the condenser lens, and in the present example, the detection sensitivity was found to be improved. This may be ascribed to the fact that in conventional thermal lens detection methods, the excitation light is strongly focused with an optical condenser lens and the like to condensed light on the sample solution and the thickness of the formed thermal lens is reduced in order to enhance the absolute sensitivity involving how many molecules of the substance in micro spaces can be detected at minimum, the concentration sensitivity of quantification of the amount of the substance per a fixed volume of sample solution is low.

On the other hand, in the fields of medical diagnosis, environmental analysis and the like, it is important that the concentration sensitivity, not absolute sensitivity is high. Therefore, unlike conventional thermal lens detection methods, the condensed degree of the excitation light is reduced and the thermal lens is widened to achieve an area approximately equal to the cross-sectional area of the channel ensuring a stable electroosmotic flow, thereby making it possible to increase the concentration sensitivity and detect the substance with high sensitivity with a capillary of small sectional-area that enables a stable electroosmotic flow.

Procedures for analyzing actually a substance in the capillary formed in a chip as of the present invention using the thermal lens detection method will be described.

Figure 2:
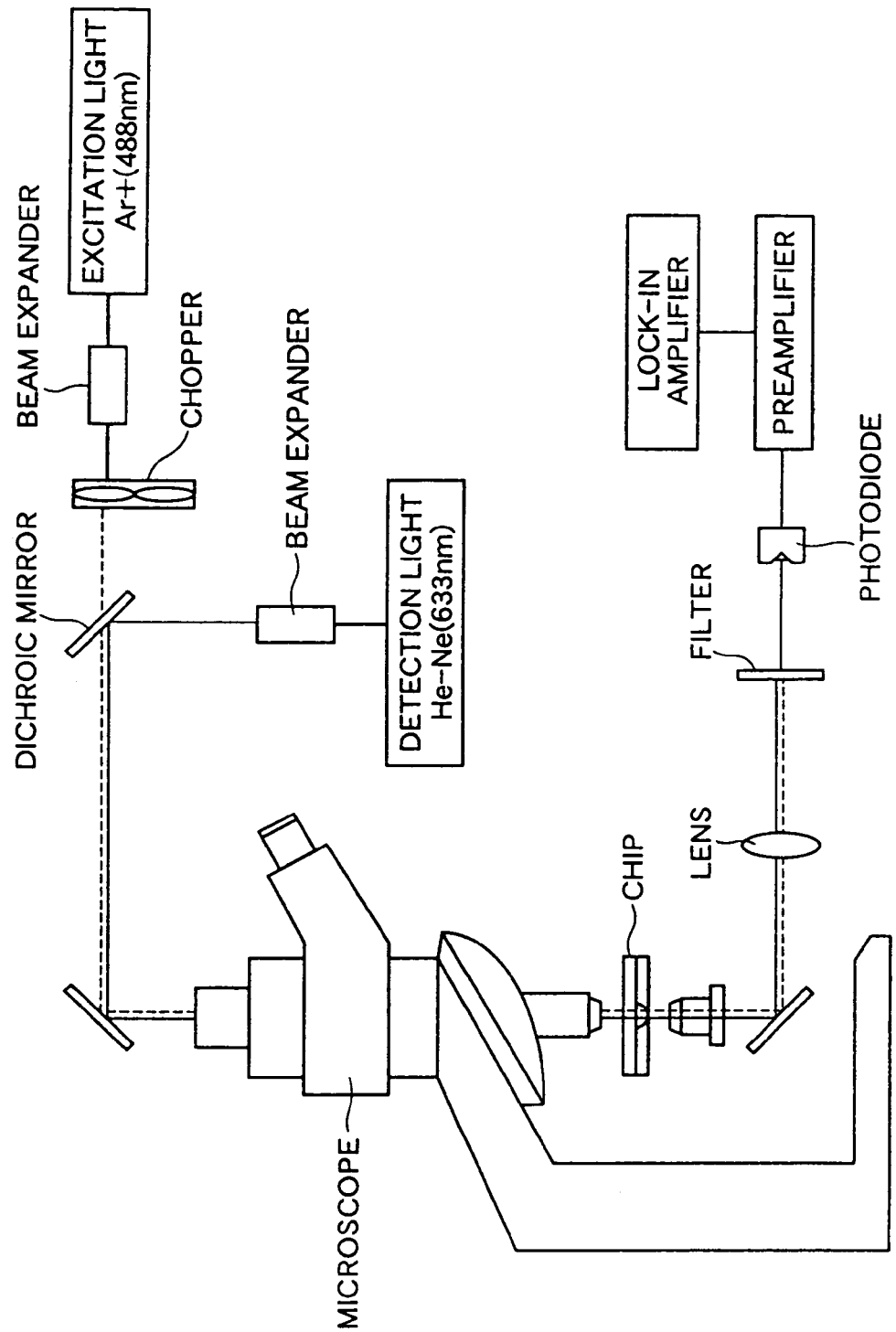
FIG. 2 is a block diagram of photothermal detection equipment according to the present invention.

Each optical part including a microscope shown in FIG. 2 is placed on a stabilized laboratory table. The laboratory table desirably has an anti-vibration effect. Also, the microscope for letting laser beams condense comprises an inlet port allowing the laser beams to be introduced directly from the outside. Furthermore, the frequency of the chopper placed on the optical path of the excitation light was adjusted to 116 Hz. This value can be changed as long as care is taken so as to prevent picking up noise from a noise source such as an electric power source.

First, the optical axes of excitation light, detection light and beam expanders placed at some midpoint in the respective optical path of excitation light and detection light are adjusted. For the detection light, in particular, a strict adjustment is carried out so that the axis is not shifted even when the collimation degree of the beam is varied. In this time, the magnification rate of the beam expander was set to be 10 times. Next, these two laser beams are arranged to be coaxial using a dichroic mirror. The dichroic mirror has a transmittance of 90% or higher for the excitation light and a reflective index of 80% or higher for the detection light. Due to these characteristics, it was possible to arrange both the excitation light and detection light to be coaxial while reducing the loss of quantity of the light. After they are arranged to be coaxial, the collimation degree of the beam expander of the detection light is varied, and by visual inspection under the microscope, the coaxial property of the excitation light and detection light is enhanced at such a level that the coaxial property with the excitation light is not reduced.

A chip for use in measurement is placed under the microscope and a measurement sample is introduced into the capillary formed in the chip. Then, height adjustment is carried out so that the focal point of the excitation light is at the center of the direction of depth of the capillary. The objective lens may be adjusted in the range of 0.2 to 0.8 of NA if the depth (width) of the capillary is in the range of 50 to 100 μm, and the sensitivity was studied for three points of 0.2, 0.4 and 0.6 of NA. The height adjustment is carried out by moving the chip slightly up and down while watching the reflection at the air/substrate interface or the substrate/capillary interface. In this case, an error approximately equal to focal depth of the excitation light due to a visual observation may be caused, and the scale of the error may be 2 μm in case an objective lens whose numerical aperture is 0.4, but errors at this level cause no problems. First, the height of the chip into which the sample is introduced is adjusted as described above using an objective lens whose numerical aperture is 0.2. At that time, the beam expander is adjusted so that difference between focal positions of the excitation light and detection light is almost equal to the depth of the capillary and the focal position of the detection light is shifted from the focal position of the excitation light towards the objective lens. It is about 50 μm in this case. The beam expander is adjusted so that the detection light converges, and the focal position of the detection light is shifted from the excitation light towards the objective lens. In this condition, the output of the lock-in amplifier, namely the output with the thermal lens detection method is verified. At this time, the time constant of the lock-in amplifier was set to one second. In this condition, in order to ensure that a sufficiently significant value is generated and that stray light of excitation light does not exist in a light detector, whether the aforesaid output with the thermal lens detection method is sufficiently reduced is checked under the condition that only excitation light is applied. Next, the convergent angle of the beam expander for the detection light is adjusted, and is adjusted to a position at which the signal reaches its maximum while watching the output with the thermal lens detection method. The aforementioned operations are carried out for three points of 0.2, 0.4 and 0.6, and the numerical aperture providing an optimal sensitivity is selected. Taking the capillary with depth of 50 μm as an example, when an objective lens whose numerical aperture is 0.4 was used, highest concentration sensitivity could be obtained with the thermal lens detection method.

Furthermore, objects that can be detected with the thermal lens detection method are not limited as long as they absorb excitation light, but they should be separated from other substances in the sample, especially substances absorbing excitation light and substances absorbing detection light or having fluorescence for the wavelength of the detection light before photothermal conversion is performed. The degree of absorption of detection light is preferably in the range of 1,000 to 100,000 of molar absorptivity in terms of sensitivity.

Detection object substances absorbing no or little excitation light are converted into substances absorbing the excitation light (pigment in case of visible rays) for measurement with combination of reactions using enzymes having the detection object substance as substrates in combination. Alternatively, using an antibody against the detection object substance, the antibody or a secondary antibody is marked with a substance absorbing excitation light, and excitation light generated directly or as a result of the enzyme reaction is measured.

In case biological materials are detected as detection object substances, for example, it is possible to convert them ultimately into the following substances with reactions using enzymes having the detection object substance as substrates in combination (Aoyama, N. Clinical Examination, 41:1014 (1997)). That is, conversion into substances absorbing excitation light, which are condensation products of N-ethyl-N-(3-methyphenyl)-N'-acetylethylenediamine (EMAE), N-ethyl-N-(3-methylphenyl)-N'-succinylethylenediamine (EMSE), N-ethyl-N-(3-sulfopropyl)-3,5-dimethoxyaniline (DAPS), N-(3-sulfoprpyl)-3,5-dimethoxyaniline (HDAPS), N-ethyl-N-(2-hydroxy-3-sulfopropyl)-3,5-dimethoxyaniline (DAOS), N-(2-hydroxy-3-sulfopropyl)-3,5-dimethoxyaniline (HDAOS), N-(2-hydroxy-3-sulfopropyl)-3,5-dimethoxyaniline (HSDA),
N-ethyl-N-(2-hydroxy-3-sulfopropyl)-3-methylaniline (TOPS),
N-ethyl-N-(2-hydroxy-3-sulfopropyl)-3-methylaniline (TOOS),
N-ethyl-N-(2-hydroxy-3-sulfopropyl)-3,5-dimethylaniline (MAPS),
N-ethyl-N-(2-hydroxy-3-sulfopropyl)-3,5-dimethylaniline (MAOS), N,N-bis(4-sulfobutyl)-3,5-dimethylaniline (MADB),
N,N-bis(4-sulfobutyl)-3,5-dimethoxyaniline (DADB), etc. and 4-aminoantipyrine, or substances absorbing excitation light, such as bis {4-[N-3'-sulfo-n-propyl]-N-n-ethyl} amino-2,6-dimethylphenyl} methane (Bis-MAPS—C2), bis{4-[N-3'-sulfo-n-propyl]-N-n-propyl}amino-2,6-dimethylphenyl} methane (Bis-MAPS-C3) and bis{4-[N-3'-sulfo-n-propyl]-N-n-butyl}amino-2,6-dimethylphenyl}methane (Bis-MAPS-C 4).

When these reactions are carried out in the chip, the reagent solutions may be supplied from the outside of the chip using a tube and needle. Alternatively, the reagent solutions contained in small containers such as plastic bags (materials may be polyethylene, polypropylene, polyester, nylon, polyvinyl chloride and the like as long as they don't interact with the reagent) are set, and then such bags may be broken by pressing the plastic bags with the needles in the chip from outside to transport the reagent solutions into reagent reservoirs in the chip. Furthermore, there is a method among others in which the reagent is contained in the chip as dried solids, and then water in or outside the chip or water or a buffer from a buffer reservoir is put in portions in which the solid reagents are contained to make reagents in predetermined concentrations.

Also, the sample may be put directly in the chip. Also, in case of analysis of pollutants in the river and analysis of urine, the sample may be concentrated as a pretreatment using a membrane filter that can be separate by molecular weight and so on. Also the sample may be introduced into the capillary after dusts and blood cells are removed by providing the chip with a filter.

(Flow Rate Ratio)

In the capillary of the chip of the present invention, channel portions intended for different operations as main purposes portion by portion, such as a channel portion intended primarily for sampling of a fixed amount, a channel portion intended primarily to mix reagents and samples and a channel portion intended primarily to transport reagents and samples can be made. In case an electroosmotic flow is used as liquid delivering means, a channel portion intended primarily for electrophoretic separation may also be made in addition to the aforesaid channel portions. Of course, one channel portion may have two or more purposes regardless of liquid delivering means such as pump delivery and an electroosmotic flow by which liquid is delivered. Also, for the chip of the present invention, the channel may be constituted by a channel portion intended primarily for one operation, but may also be constituted by a combination of plurality of channel portions that are intended primarily for different operations. In this way, equipment allowing not just a simple qualitative analysis, but a high level analysis involving a quantitative analysis and reaction to be performed may be provided.

Figure 3:
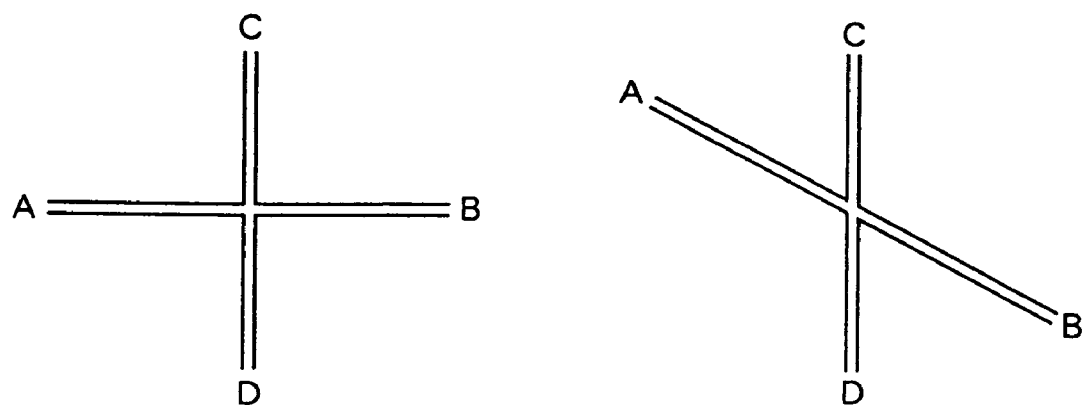
FIG. 3 is a channel pattern-1 intended for sampling of a fixed amount.
Figure 4:
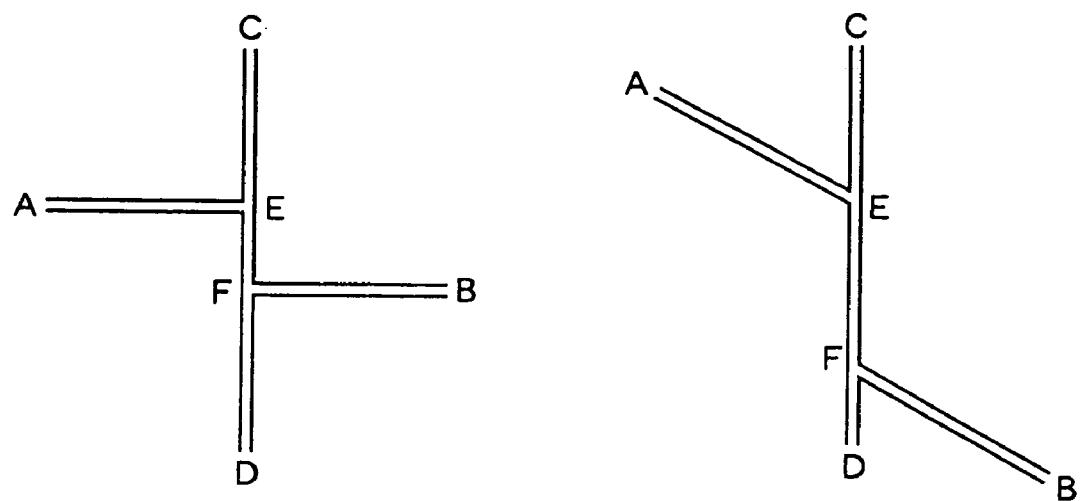
FIG. 4 is a channel pattern-2 intended for sampling of a fixed amount.

The shape of the channel portion intended primarily for fixed amount sampling is a shape as shown in FIG. 3 in which two channels cross each other in the shape of a cross, or a shape as shown in FIG. 4 in which two channels are merged with one channel in the shape of T, respectively, and the shape shown in FIG. 4 is preferable. In a channel having the shape shown in FIG. 3, fixed amount sampling is performed by flowing the sample from A towards B, followed by stopping the flow toward B, and then flowing the sample from A towards D for a certain time period, followed by stopping the flow from A, and further flowing the fluid from C toward D. In this case, fixed amount sampling is carried out by the cross-sectional area, flow velocity and time.

Also, in a channel having the shape shown in FIG. 4, fixed amount sampling is performed by flowing the sample from A toward B, followed by stopping the flow, and then flowing the fluid from C towards D. In this case, fixed amount sampling is carried out by the cross-sectional area of the capillary and the length between the T-shaped channel merging point E and the T-shaped channel merging point F. For this shape, the amount for sampling is determined only by the cross-sectional area of the capillary and the length between the merging point E and the merging point F, regardless of the flow velocity of the fluid and the time period during which the fluid flows, as long as the capillary is fabricated with good dimensional accuracy. Also, it may be a further preferable sampling method since the amount for sampling can be set arbitrarily by changing the cross-sectional area of the capillary and the length between the merging points E and F.

The shape of the channel portion primarily intended for mixing and dilution of reagents and samples includes a shape with a widened and/or deepened area at some midpoint in the channel (It may be preferable that the size of this area is set to the order of millimeters to centimeters) for performing the mixing and dilution in combination with sampling. Furthermore, it is preferable that uniformizing processes of stopping delivery of liquid temporarily to render the fluid uniform by diffusion, of rendering the fluid uniform by mechanical agitation, and so on are adopted. In particular, a structure allowing mechanical agitation (for example, an agitation bar is placed and agitation is made using magnetic power) is preferable in that it does not requires time substantially for rendering the fluid uniform.

Also, depending on channel structures, shapes of channel intended primarily for mixing and dilution of samples and reagents can include a shape in which one channel is merged with another channel and a shape in which a plurality of channels are merged with one channel at one point. By merging one channel with another channel or plurality of channels to make one channel, mixing and dilution operations can be carried out only with channel shape. Also, at this time, mixing and dilution can be carried out at different ratios by varying each flow rate. In case of liquid delivery using pumps, it is possible to vary mechanically the flow rate in each channel to be merged. Also, in case of liquid delivery using electroosmotic flows, the flow rate in each channel to be merged can be varied by varying the size of cross section and the length of each channel to be merged, varying the way of applying voltages to each channel and varying the charged condition of the inner surface of each channel with surface treatment and the like. Also, in case of having a pump at the outer side, the kind of the pump is not limited, including a system in which pneumatic pressure is generated with a syringe pump and the fluid is pushed out with that pressure, a system of suction, and so on. In this case, it is preferable that a baffle structure is provided in the merging area, and a channel for rendering the liquid uniform by diffusion is provided behind the merging area. Shapes of channel portions for rendering the fluid uniform include shapes such as linear shape and bent shape like meander and helices. In addition, it is necessary to secure a time necessary and sufficient for the mixed fluid to carry out predetermined reaction, but needed reaction was carried out without using additional means for measuring reaction time, by making the channel distance between a merging point and a next merging point or a detecting portion to be a required distance according to a predetermined flow rate obtained after mixing.

As for means for transporting fluids, mechanical means such as pumps or electrical means such as electrosomotic flows can be used.

In case the fluid in the capillary is transported using liquid delivery pumps or suction pumps operated by drivers outside the chip (also including a case where pumps in the chip is operated by drivers outside the chip), the flow rate can be controlled by the discharge or suction rate of the pumps, or can be controlled with mechanical means including use of a flow rate control valves.

Furthermore, in contrast to what is describe above, diversion can also be achieved by making one channel branching into multiple channels (diverting a channel).

Shapes of channel portions intended primarily for electrophoretic separation in case the electroosmotic flow is used as liquid delivering means include linear shapes and bent shapes like meander and helices. The bent shape like meander and helices can enhance separation capability compared to the linear shape because it is possible to render the length of the channel for separation longer than the length of the longer side of the chip.

The analyzer of the present invention can be used for multiple analytical purposes by varying channel patterns (configurations). For example, it is possible to provide a configuration centering on a channel intended primarily for mixing and separation for use in qualitative analysis, to provide a configuration with a channel intended primarily for quantitative sampling and a channel intended primarily for separation in combination, to provide a configuration centering on a channel intended primarily for quantitative mixing for use in quantitative analysis involving separation and quantitative analysis involving reactions, to provide a configuration with a channel intended primarily for quantitative sampling and a channel intended primarily for mixing in combination and a channel intended primarily for separation in combination for use in quantitative separation analysis involving reactions, and to provide a configuration principally with a channel intended primarily for quantitative sampling and a channel intended primarily for mixing for use in analysis that does not involve so much separation.

In the chip of the analyzer relating to the present invention, samples are controlled by an electroosomotic flow, electrophoresis or other appropriate means, and dilution and reaction with other reagents are performed. Also, for operations such as merging of these fluids, timing should be generally accurately controlled. It has been found that performing these operations accurately, simply and without using extra devices such as timers can be realized by mixing and reacting respective fluids at a predetermined flow rate, and giving a capillary of length necessary and sufficient for flowing for a time period required for mixing and reaction to the merged fluid flowing at a predetermined flow rate. It will be described in detail below. Furthermore, the flow rate according to the present invention means a volume of the fluid moving in the capillary for a certain amount of time.

Using figures, apart of this technique related to mixing and reaction will be described further in detail. In the following description, it is assumed for the purpose of simplification that all channels have the same depth, but the depths may be different from each other in case of actual implementation. Similarly, for the purpose of simplification, it is assumed that the flow velocity of the fluid before being merged, namely the travel length per unit of time equals v for all fluids. Also in this case, it may be different for each fluid in case of actual implementation. In the following description, it is assumed that each fluid before being merged continues to move at a rate of v and never stops.

Figure 5:
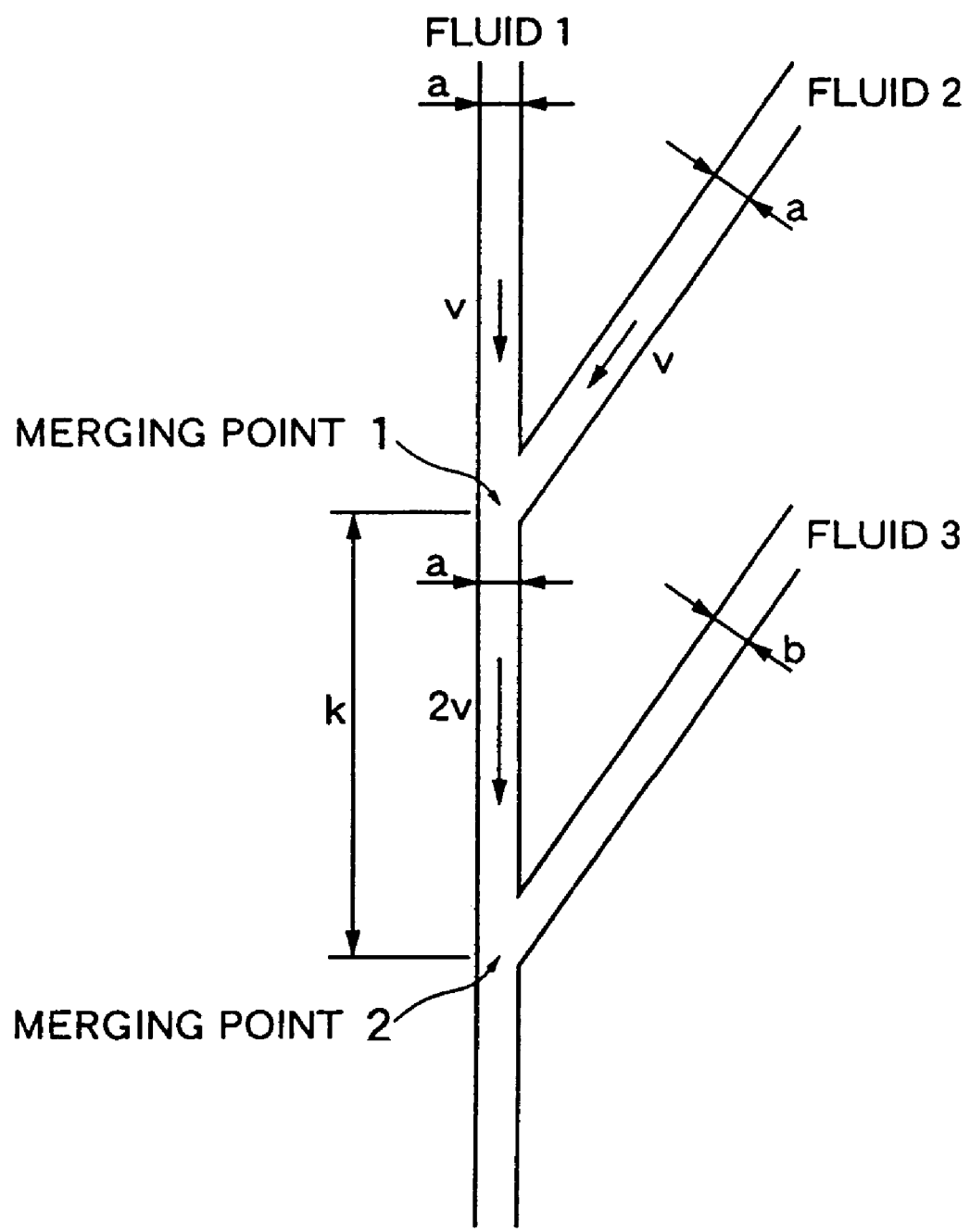
FIG. 5 is a schematic diagram-1 of a channel in which a plurality of fluids are merged with each other to have dilution, mixing and the like performed according to the present invention.

FIG. 5 shows a channel in which a fluid 1 and a fluid 2 are merged at a merging point 1 and mixing and reaction are carried out spending a predetermined time, followed by merging a fluid 3 with a mixture of the fluid 1 and the fluid 2. In FIG. 5, the widths W of the channels through which the fluid 1 and the fluid 2 flow before reaching the merging point 1 are equal to a and the width of the channel from the merging point 1 to a merging point 2 after they are merged is also equal to a. Under this condition, it is apparent that the flow velocity of the mixture of the fluids 1 and 2 flowing between the merging point 1 and the merging point 2 equals 2v. Also, it is apparent that the mixing ratio of the fluid 1 and fluid 2 is 1:1. Assuming that the length of the channel between the merging point 1 and merging point 2 equals k, time to be taken for the merged fluid to move from the merging point 1 to the merging pint 2 would be k/(2v). Since the values, k and v can be individually adjusted by adjusting the layout of the capillary and liquid delivering means and so forth, k and v are adjusted so as to provide a time adequate for mixing and reaction, thereby making it possible to adjust accurately the time before merging with a fluid 3, a next process, without recourse to external timers and the like. Furthermore, the number of fluids to be merged ultimately is three or larger, three fluids or more may be merged at the same point. This remains unchanged in the following description.

Figure 6:
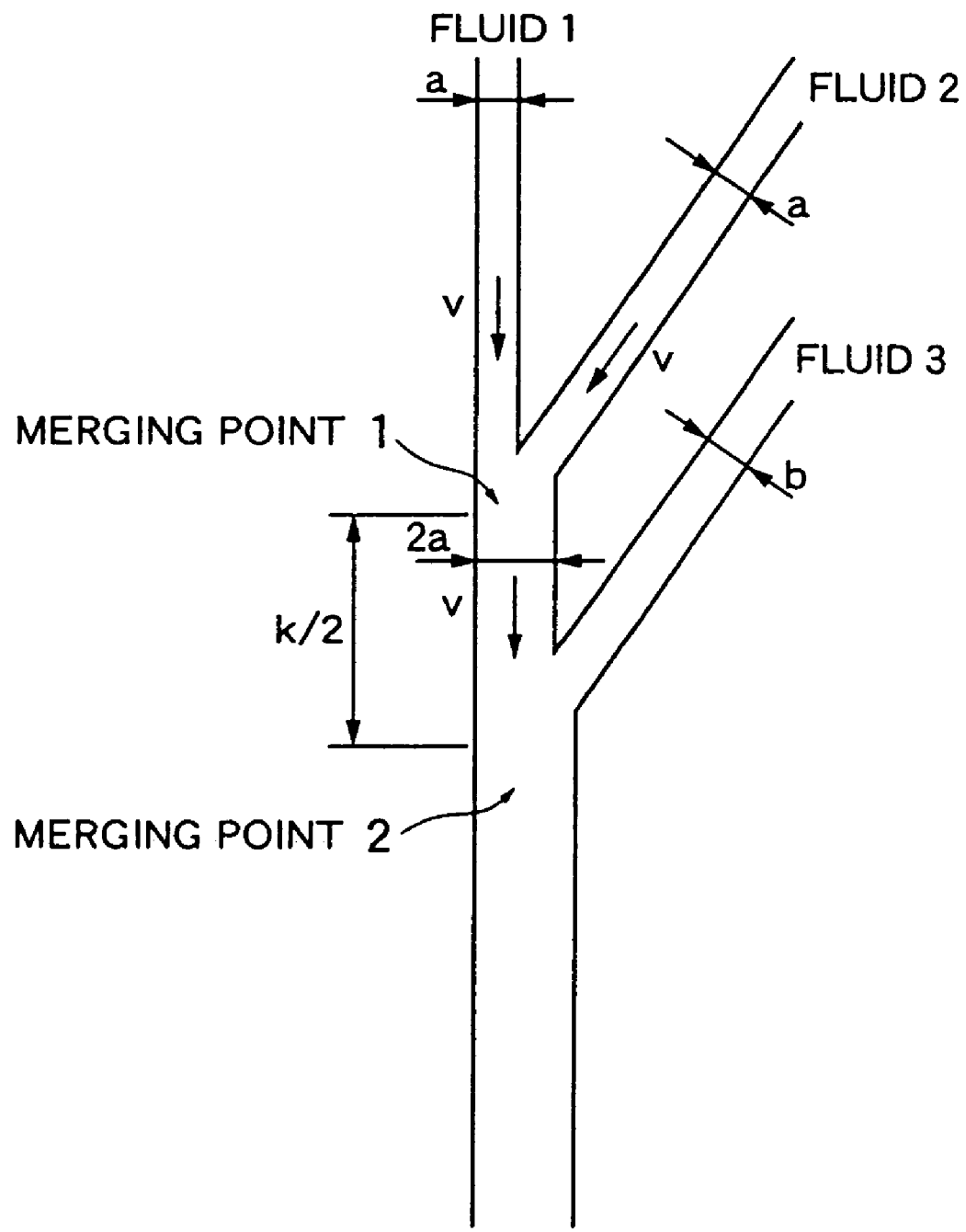
FIG. 6 is a schematic diagram-2 of a channel in which a plurality of fluids are merged with each other to have dilution, mixing and the like performed according to the present invention.

FIG. 6 shows another example, and in this figure, the widths W of the channels through which the fluid 1 and the fluid 2 flow equal a as in case of FIG. 5, but the width W of the channel after they are merged at the merging point 1 equals 2a. Under this condition, it is apparent that the flow velocity of the mixture of the fluids 1 and 2 flowing between the merging point 1 and merging point 2 is kept at v. In this case, if the time required for mixing and reaction of the fluid 1 and fluid 2 is identical to the time described for FIG. 5, in order to implement that, the length of the channel between the merging point 1 and merging point 2 may be set to k/2 as shown in FIG. 6, or the ratio of the flow velocity v in FIG. 6 to the flow velocity v in FIG. 5 may be set to 2:1 while keeping the length at k. Whether any one of them is adopted, or another appropriate combination of values if v and k is used can be basically freely decided through sometimes it may be limited by the size of the chip and liquid delivering means. Furthermore, if the width W of the channel from the merging point 1 to the merging point 2 is set to a value other than 2a, the optional range can be further widened. Furthermore, the mixing ratio of the fluid 1 and fluid 2 is 1:1 also in this case.

Figure 7:
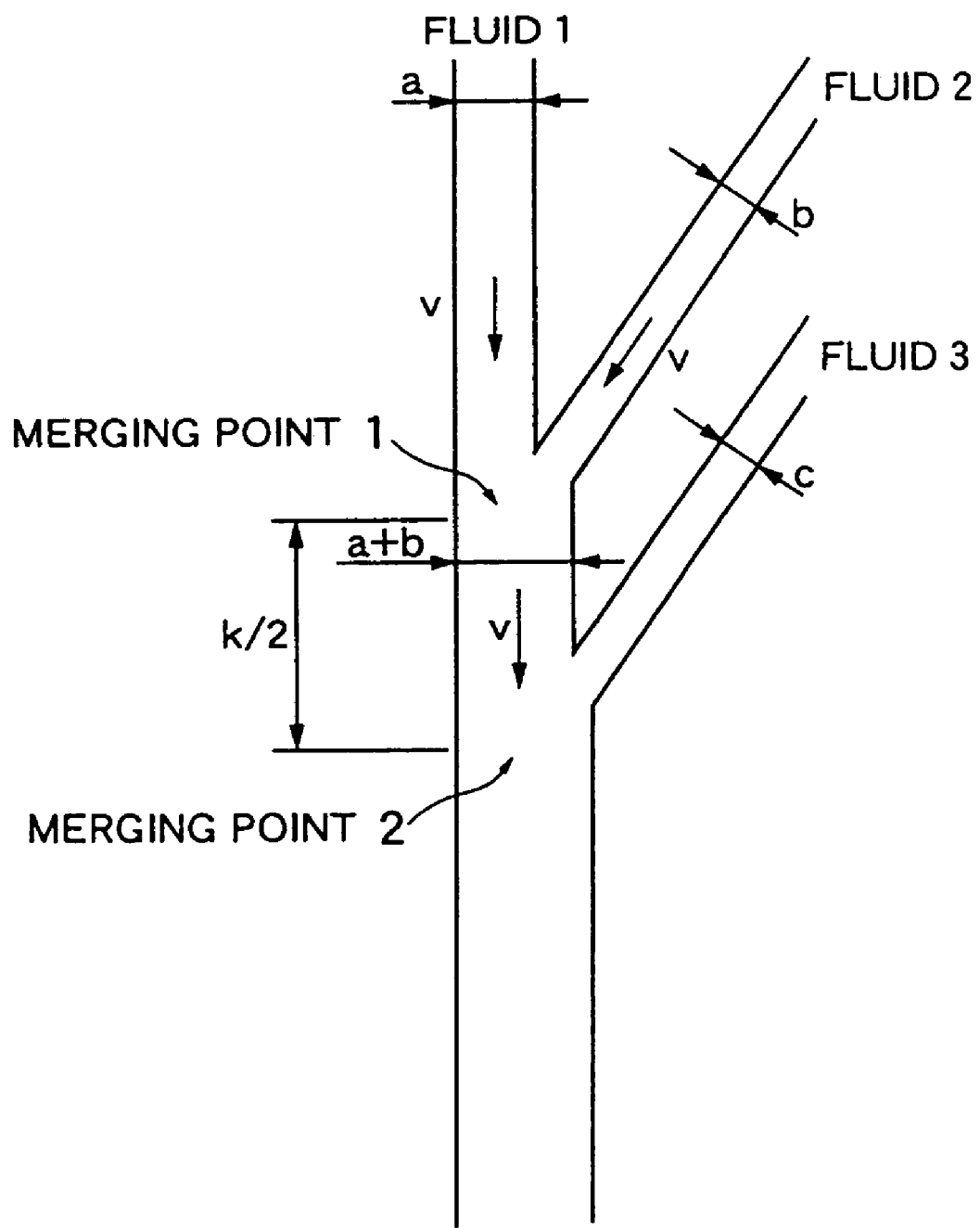
FIG. 7 is a schematic diagram-3 of a channel in which a plurality of fluids are merged with each other to have dilution, mixing and the like performed according to the present invention.

FIG. 7 shows still another example, and in this figure, the width W of the channels through which the fluid 1 and the 2 flow equals a and b, respectively, unlike the cases of FIGS. 5 and 6, the width W of the channel after they are merged at the merging point 1 equals a+b. Also under this condition, it is apparent that the flow velocity of mixture of the fluids 1 and 2 flowing between the merging point 1 and merging point 2 is kept at v. In this case, if the time required for mixing and reaction of the fluid 1 and fluid 2 is identical to the time described for FIG. 5 and FIG. 6, in order to implement that, the length of the channel from the merging point 1 and the merging point 2 may set to k/2 as described for FIG. 6, or the ratio of the flow velocity v in FIG. 7 to the flow rate in FIG. 5 may be set to 2:1. Whether any one of them is adopted, with another appropriate combination of values of v and k is used can be basically freely decided, though sometimes it may be limited by the size of the chip and liquid delivering means. Furthermore, if the width W of the channel between the emerging point 1 and emerging point 2 is set to a value other than a+b, the optional range can be further widened, as described for FIG. 6. In this way, it is possible to mix the fluids 1 and 2 at a mixing ratio of a:b and implement needed reaction without using a complicated mechanism.

Figure 8:
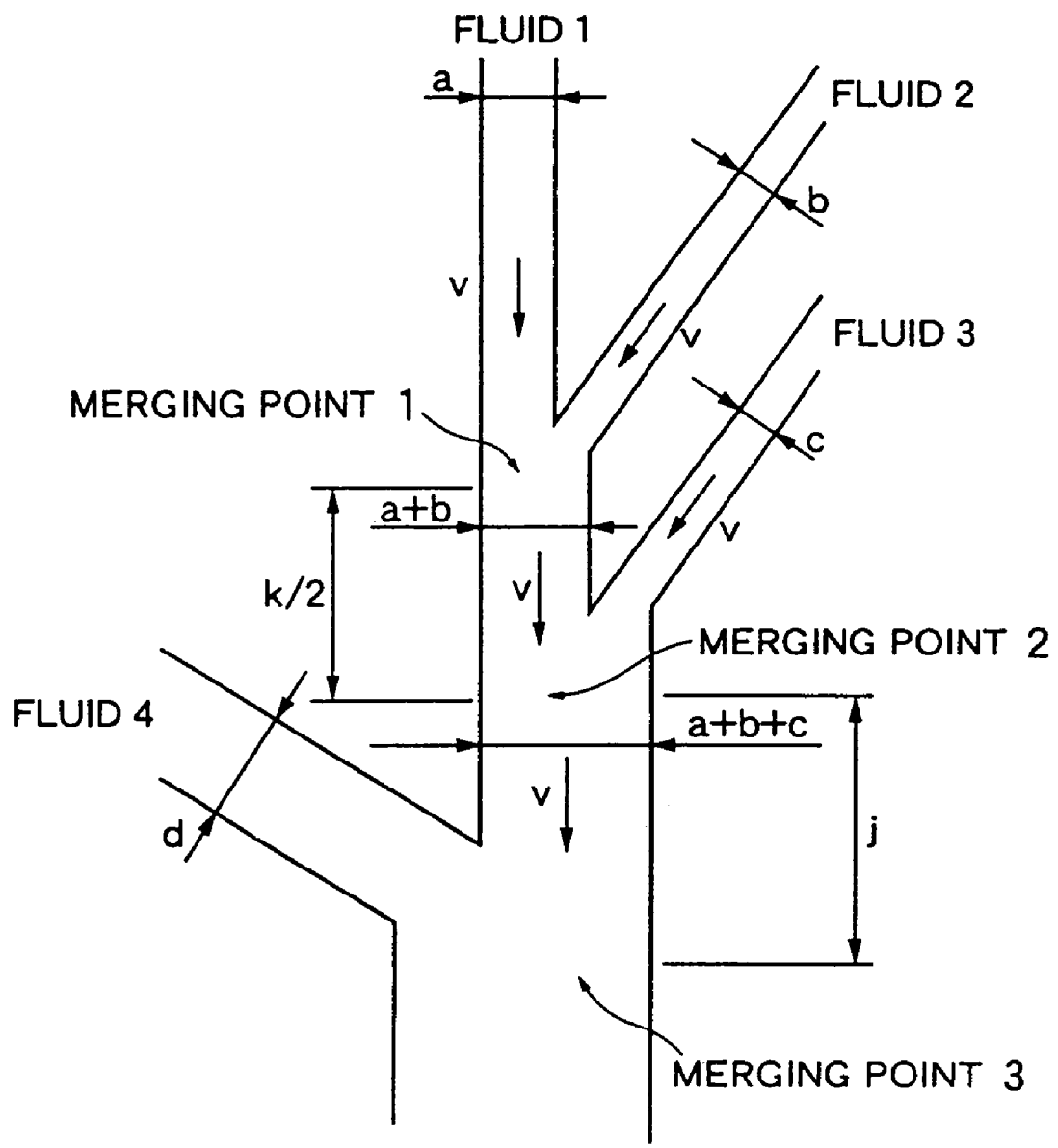
FIG. 8 is a schematic diagram-4 of a channel in which a plurality of fluids are merged with each other to have dilution, mixing and the like performed according to the present invention.

FIG. 8 shows an example further extending FIG. 5 to FIG. 7. The widths of the channels through which the fluids 1 to 4 flow equal a, b, c and d, respectively, and they are merged at the points 1 to 3, respectively, and the lengths between merging points equal k/2 and j, respectively. Also, the width of the channel from the merging point 1 to the merging point 2 equal a+b, and the width of the channel from the merging point 2 to the merging point 3 equal a+b+c. Of course, because of some limitation put on the diffusion length required for mixing and the size of the chip, these values are subject to channel width/channel length tradeoffs, and can be changed in the actual step of design. To present an explanation according to the figure, the flow velocity after emerging equals v as described for FIGS. 5 to 7, and the time between the merging of the fluid 1 and fluid 2 and the subsequent merging of the fluid 3 with them equals k/(2v), and the time between the merging of the fluid 3 with the mixture of the fluid 1 and fluid 2 and the subsequent merging of the fluid 4 with them equal j/v. The values of k/(2v) and j/v, which are determined by the length required for mixing and the time required for reaction, may be identical, but are not necessarily identical. In this way, it is possible to mix the fluids 1 to 4 in succession at a mixing ratio of a:b:c:d and at a predetermined time interval. Then, even if the number of fluids to be merged is increased, needed fluids can be mixed in succession at a predetermined mixing ratio, at a predetermined time interval and continuously in the same manner.

An embodiment for implementing the above description will be described further in detail, using FIGS. 9 to 11.

In the following description, the electroosmotic flow is used as a liquid delivering means.

The capillary of this embodiment is formed by laminating a pair of plane plate members with each other, and is constituted by a grooved plate 31 having on its surface plane-shaped grooves in accordance with defined channels and a covering plate 32 laminated with the groove-bearing surface side of the grooved plate. In the following description, this grooved plate 31 and covering plate 32 laminated with each other will be called a chip. FIG. 9 is a plan view showing the groove-bearing surface side of this grooved plate 31, FIG. 10 is a plan view showing a surface opposite to the groove-bearing surface side of this grooved plate 31, and FIG. 11 is a partial sectional view of the chip and corresponds to the a–a' line section in FIG. 10.

Respective positions corresponding to portions for introducing liquid and for reserving waste liquid and the like of the groove forming the channel of the grooved plate 31 are provided with circular through-holes 19 to 22 cutting through the plate surface. Of these through-holes, the through-holes 19 to 21 of the liquid introducing side are used as reservoirs of samples, reagents and the like, the through-hole 22 is used as a buffer reservoir and waste liquid reservoir. This grooved plate 31 can easily be formed by injection molding of PMMA and the like, using a mold provided on the cavity surface with bumps and dips corresponding to the plane-shaped groove in accordance with the defined channel.

Figure 9:
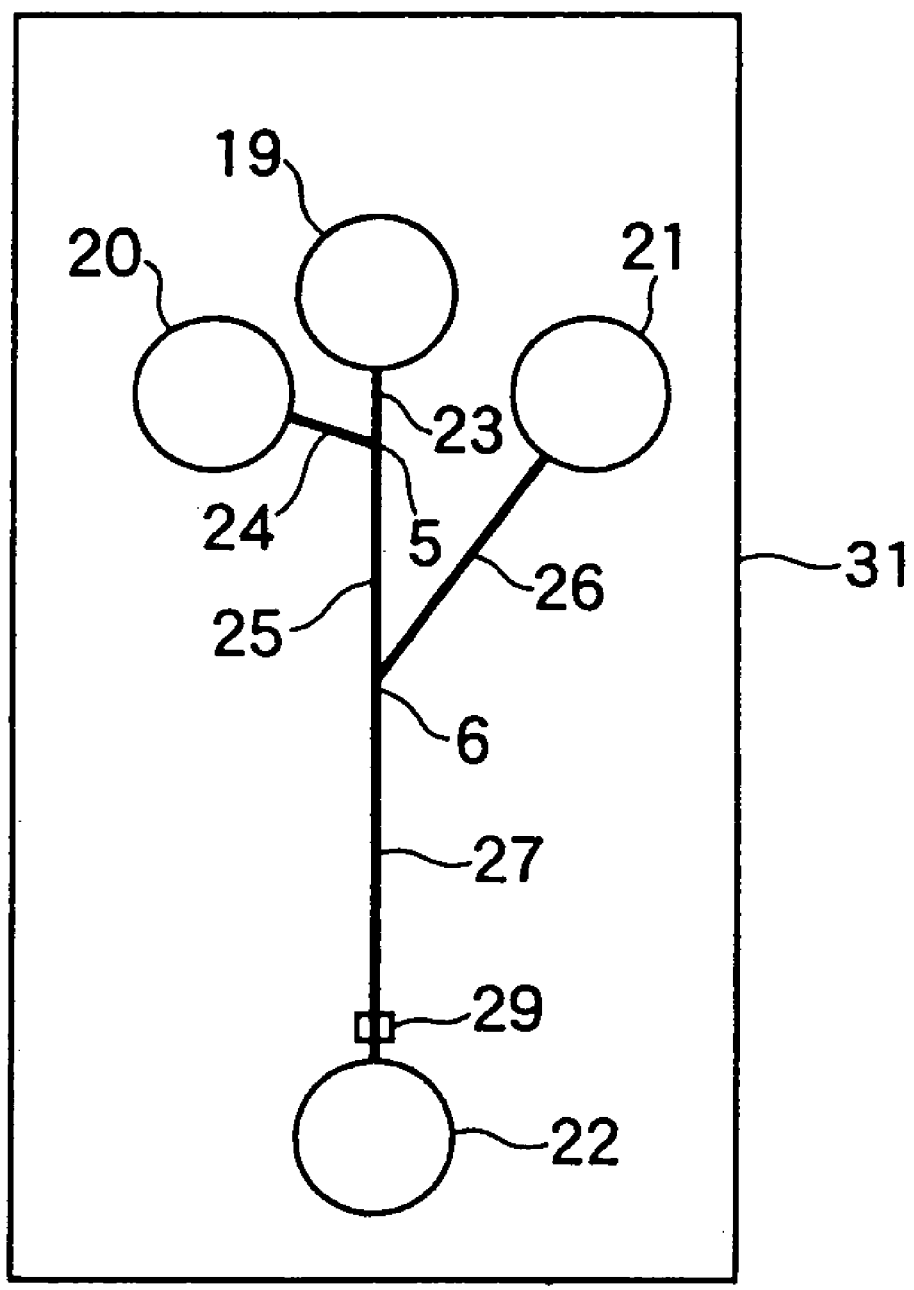
FIG. 9 is a diagram-1 showing a groove pattern of a plate member made of organic polymer having on the surface fine grooves on which the fluid flows, which is molded by injection molding.

As shown in FIG. 9, this capillary comprises a sample channel 23 connected to a sample introduction reservoir 19, a first reagent channel 24 connected to a first reagent introduction reservoir 20, a second reagent channel 26 connected to a second reagent introduction reservoir 21, a first mixing channel 25 provided in length in accordance with the time of reaction between the sample and the first reagent and a second mixing channel 27 provided in length corresponding to the time of reaction between the sample and the second reagent, and uses an edge on the side of buffer/waste liquid reservoir 22 of the second mixing channel 27 as a detecting portion 29 for a detector.

Then, the sample channel 23, the first mixing channel 25 and the second mixing channel 27 (including the detecting portion 29) are formed like continuous straight lines, a merging point 5 of the first reagent channel 24 is set in a predetermined position on the upstream side of this straight line-shaped continuous channel, and the distance from the merging point 5 equals the length corresponding to the time of reaction between the sample and the first reagent. In addition, a merging point 6 of the second reagent channel 26 is set so that the distance between the detecting portion 29 of the second mixing channel 27 and the upstream side equals the length corresponding to the reaction between the sample and the second reagent. Also, the first reagent channel 24 and the second reagent channel 26 are merged with the straight line-shaped channel at an acute angle.

Furthermore, reagent mixing means is constituted by the first reagent channel 24, the merging point 5 and the first mixing channel 25, and the second reagent channel 26, the merging point 6 and the second reagent channel 27, respectively.

Figure 11:
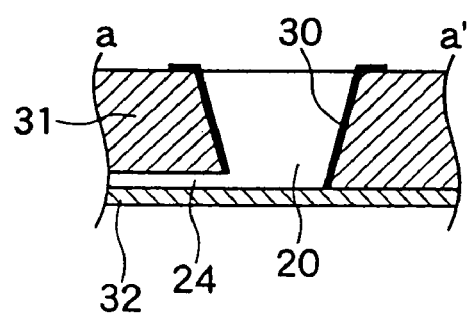
FIG. 11 is a sectional view of the a–a' line of FIG. 10.

As shown in FIG. 11, a electrode 30 is provided on the inner surface of a through-hole 20 that is the equivalent of the edge of the upstream of the first reagent channel 24. In a similar way, electrodes are also provided on the inner surfaces of a through-hole 19 that is the equivalent of the edge of the upstream of the sample channel 23, a through-hole 21 that is equivalent of the edge of the upstream of the second reagent channel 126 and a through hole 22 that is the equivalent of the edge of the downstream of the mixing channel 27.

Figure 10:
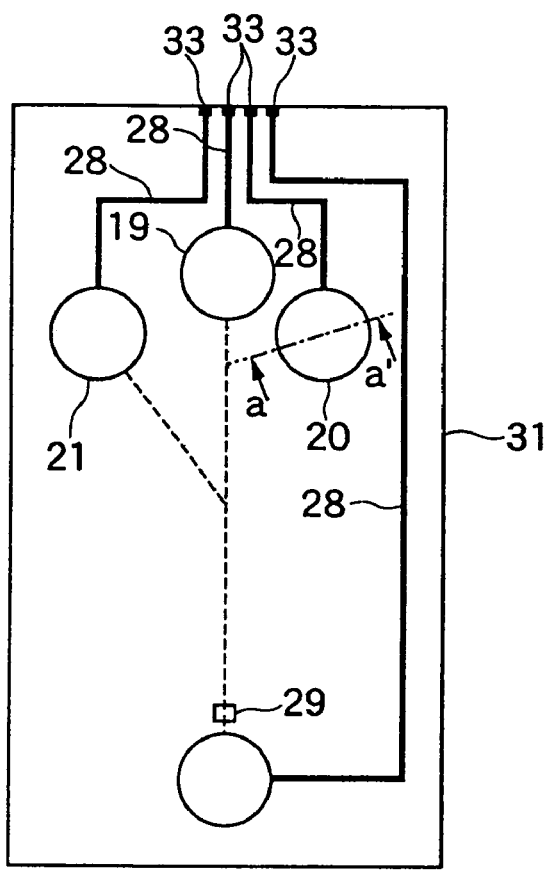
FIG. 10 is a diagram-1 showing a chip which is constituted by laminating a pair of plate members made of organic polymer, and on which a wiring, an electrode for trapping liquid and an electrode for connecting power terminals in detection equipment are printed with conductive ink.

As shown in FIG. 10, each electrode 30 is connected to a different electrode 33 provided on the edge of the liquid introduction side of the grooved plate 31 with different wiring 28. These electrodes 33 are connected to the terminal of the power supply in the detector, and are arranged so that voltage is separately supplied from each electrode 33 to between the through-hole 19 and through-hole 22, to between the through-hole 20 and through-hole 22, and to between the through-hole 21 and through-hole 22. Voltage to be supplied to each electrode 33 is controlled in response to each defined flow rate at the sample channel 23, the first reagent channel 24, the second reagent channel 26, by a voltage control device in the detector.

Furthermore, these electrodes 30, 33 and the wiring 28 are formed by performing printing on the surface opposite to the groove-bearing surface side of this grooved plate 31 with conductive ink containing particles such as silver and copper after laminating the grooved plate 31 with the covering plate 32 with adhesive. Also, as shown in FIG. 11, the section of the through-hole 20 is shaped into a taper with the groove-bearing surface side being narrower, thereby making it possible to provide the electrode 30 on the inner surface of the through-hole 20 by printing while keeping horizontal plate surface of the grooved plate 31.

In case this analyzer is used, first, a predetermined amount of buffer is added in the aforesaid buffer reservoir 22 of the chip to fill buffer in all the channels 23 to 27, and then a predetermined amount of first reagent, second reagent and sample are put in the first reagent reservoir 20, the second reagent reservoir 21 and the sample reservoir 19, respectively. Next, voltage generating electroosmotic flows corresponding to the set value of the flow rate of each channel is applied separately to between the through-hole 19 and through-hole 22, between the through-hole 20 and through-hole 22, and between the through-hole 21 and through-hole 22 by means of voltage setting of the voltage control device. At this time, the set value of the flow rate is set so that the ratio of the flow rate of the sample channel 23 to the flow rate of the first reagent channel 24 equals the mixing ratio of the sample to the first reagent, and the ratio of the flow rate of the first mixing channel 25 to the flow rate of the second reagent channel 26 equals the mixing ratio of the sample and first reagent to the second reagent.

In this way, the liquid in each channel moves at a flow rate corresponding to the set value for each channel by means of electroosmotic flows. Specifically, the sample and first reagent move to the merging point 5 at a flow rate corresponding to the mixing ratio, and are mixed at a ratio corresponding to the ratio of their flow rates in the first mixing channel 25. Then they reach the merging point 6 after reaction between the sample and the first reagent is completed, and they flow through the second mixing channel 27. Also, the second reagent moves from the second reagent channel 26 to the merging point 6 at a flow rate corresponding to the mixing ratio to the sample, is mixed with the mixture of the sample and first reagent at a ratio corresponding to the above described mixing ratio in the second mixing channel 27, and flows through the detecting portion 29 after reaction between the sample and the second reagent is completed.

Thus, according to this analyzer, once this chip is set in the detector described later, the mixing and reaction of the sample with the first and second reagents at a predetermined ratio are automatically carried out. Detection is made for the detecting portion 29 using the detector described later to detect an analysis component automatically.

For describing the present invention more clearly and specifically, the case of a sample and two reagents, such as a measurements of total cholesterol in a serum that is one of specific measurement items in medical diagnosis will be described as an example.

Usually, the sample is weighed and taken using, for example, a 3 µl pipette and is mixed with, for example, 200 µl of a first reagent solution (reagent 1) that is weighed and taken, and they are left to react, for example, for three minutes. After that, 100 µl of a second reagent solution (reagent 2) that is weighed and taken is added to the reactant solution and is mixed. After they are allowed to react with each other for a predetermined time, for example, ten minutes, the absorbance of the coloring reagent in the reactant mixture is measured, thereby determining the amount of a detection object substance (such as cholesterol) in the sample.

For performing this using the method of the present invention, a channel through which the reagent 1 flows at a flow rate of 2000 nl/min is merged with a channel through which the sample flows at a flow rate of 30 nl/min to provide a flow rate of 2030 nl/min, and the channel length is designed so that three minutes of reaction time can be obtained. Then, this mixture channel of the reagent 1 and the sample is merged with a channel through which the reagent 2 flows at a flow rate of 1000 nl/min to provide a flow rate of 3030 nl/min, and the channel length is designed so that ten minutes of reaction time can be obtained, and finally, detection such as photothermal detection is performed.

That is, the flow rate can be accurately controlled by pumps, voltages and the like, thereby making it possible to carry out mixing and reaction at determined ratio without weighing and taking a fixed volume of solution. In particular, in case the post-reaction liquid can be set directly in the detector without performing special separation, the present invention is especially useful, for example, in measurements among Biochemical Items I for medical diagnosis.

Furthermore, in the above explanation, the linear velocity may be changed by changing the cross-sectional area of the capillary by means of varying the depth as necessary and so on, just as described before.

Figure 12:
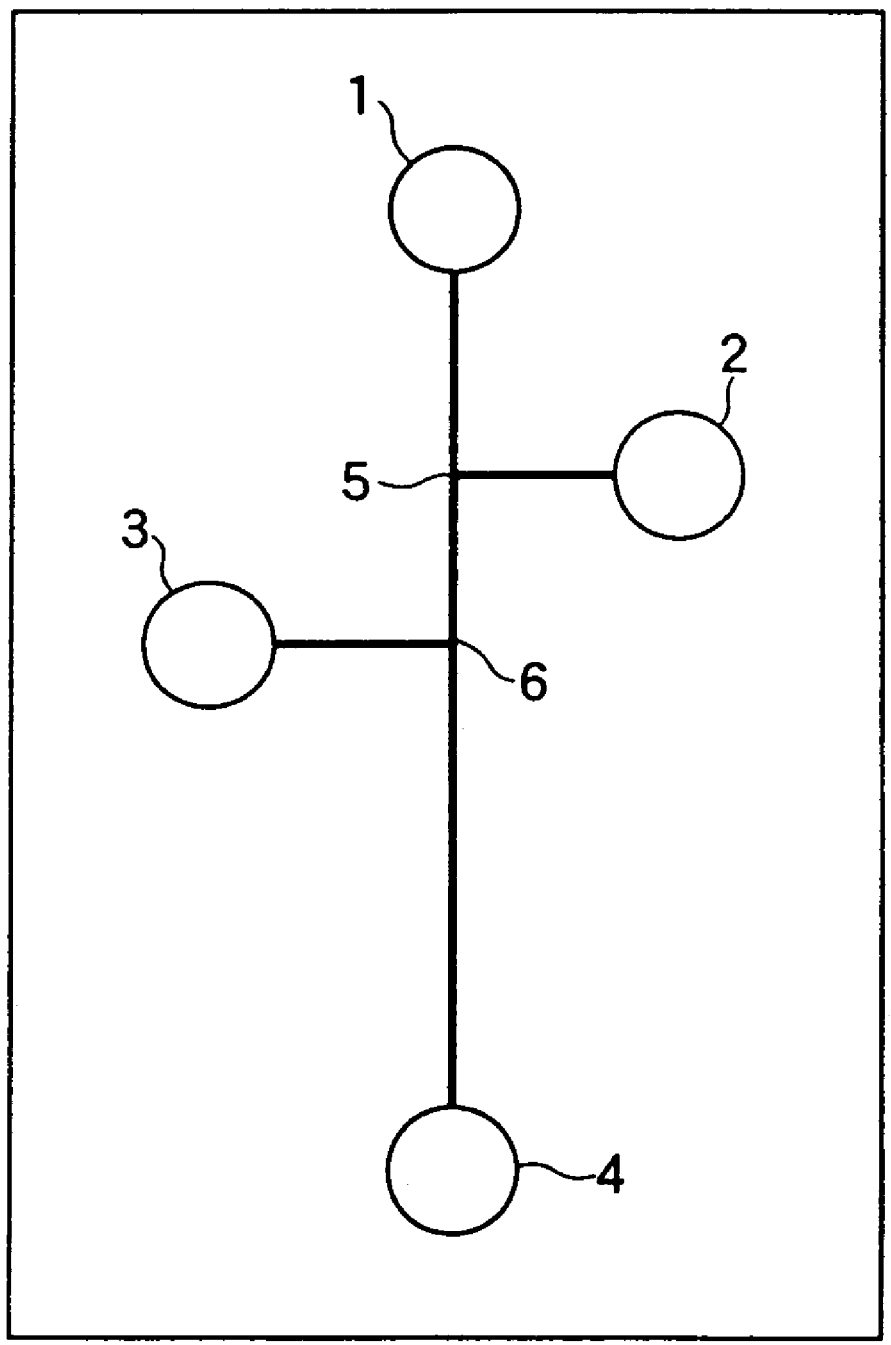
FIG. 12 is a diagram of a channel in which at a merging point, side flows merge at right angles to have two reagents merged with each other.
Figure 13:
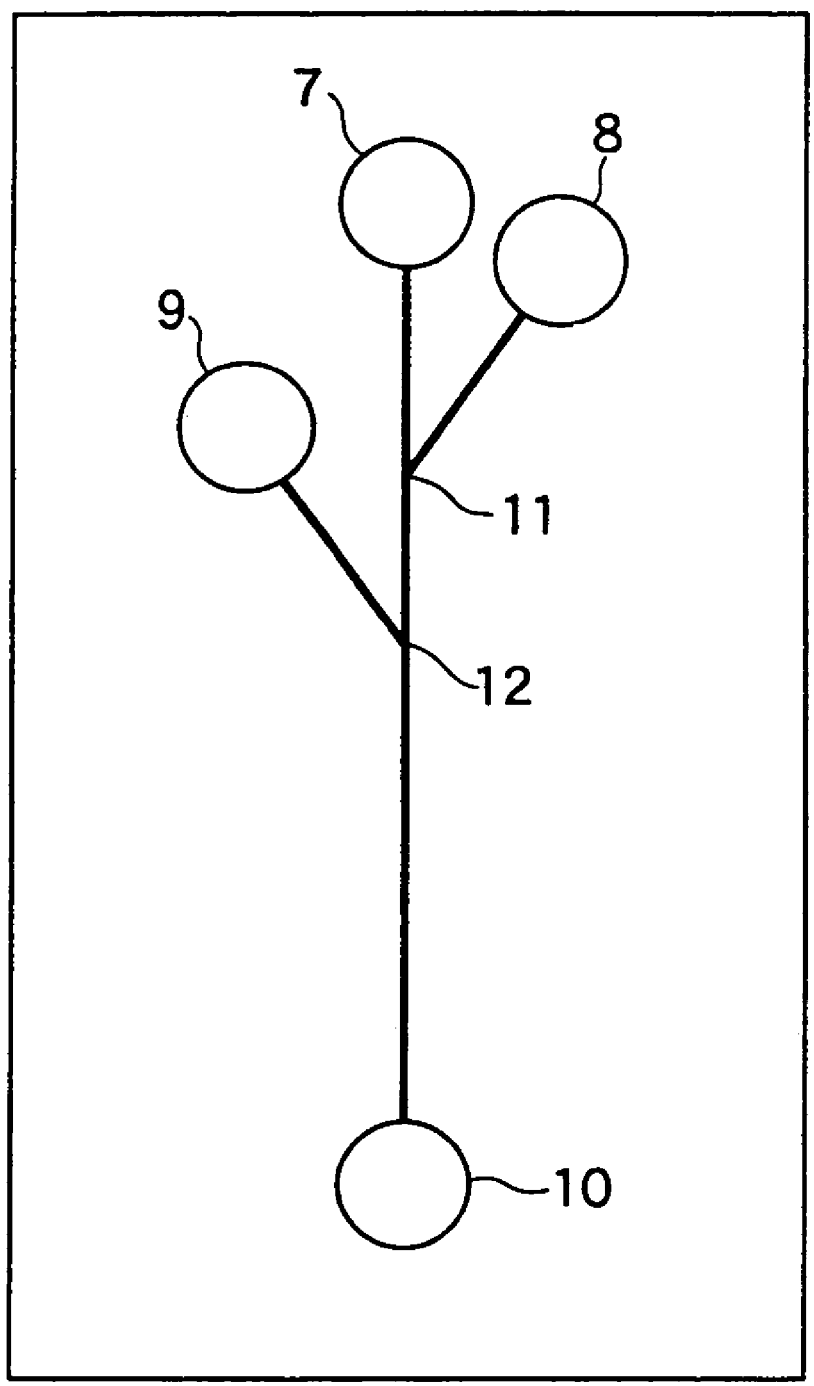
FIG. 13 is a diagram of a channel in which at a merging point, side flows merge at an acute angle to have two reagents merged with each other.

An example of a pattern of a channel is shown in FIG. 12. A reservoir 1 is a reservoir for the sample, a reservoir 2 is a reservoir for the reagent 1, a reservoir 3 is a reservoir for the reagent 2 and a reservoir 4 is a reservoir for waste liquid. The sample is mixed with the reagent 1 at the merging point 5 and is further mixed with the reagent 2 at the merging point 6. The angle formed by both grooves is a right angle in this case, but as shown in FIG. 13, they may be merged at an acute angle, thereby making it possible to further reduce the influence by the change in flow rates due to pressure from the merging counterpart and so force to perform mixing. Furthermore, to perform mixing more efficiently, a protrusion such as a baffle for disturbing the flow may be provided on the emerging area, or mixing may be performed by means of diffusion with the groove width of the merging area being enlarged and the residence time being increased.

In case detection can be carried out without requiring separation after reaction between the sample and reagent as described before, especially in case of Biochemical Examination Items, processes can be continuously carried out in a consistent channel from mixing to reaction to detection without weighing and taking a fixed amount for separation. Generally, for example, in case a component to be detected can be detected without being interrupted by other impurities depending on absorption wavelengths, and in case a substance to be detected is subject to change such as the case where hydroxyl groups in the sample are oxidized and resultant carbonyl groups are detected by a spectrophotometer, processes can be performed in a continuous channel from mixing at a predetermined flow ratio to reaction and detection without separation.

The method of the present invention can be performed continuously over long hours, but is not necessarily performed over long hours. For example, in the description of the previous paragraph, assuming that it takes ten seconds to carry out detection, the reagent 1 and the sample may be merged for 10 seconds at the minimum (normally, slightly longer, that is about 20 seconds), and after three minutes, they may be merged with the reagent 2 for ten seconds at the minimum in the same manner. Then, after ten minutes, detection is carried out. That is, in the method of the present invention, flow rates are controlled programmatically over time, thereby making it possible to perform micro analysis efficiently with a minimum amount of reagent and sample and without weighing and taking a fixed volume. Thus, the accuracy and programmability of flow rate control and quick-response are important. For the verification of the flow ratio, correction can be easily carried out by passing a standard sample instead of a sample and so on. Alternatively, the size of the channel in the chip is verified lot by lot in advance, and their correction values may be used.

Figure 14:
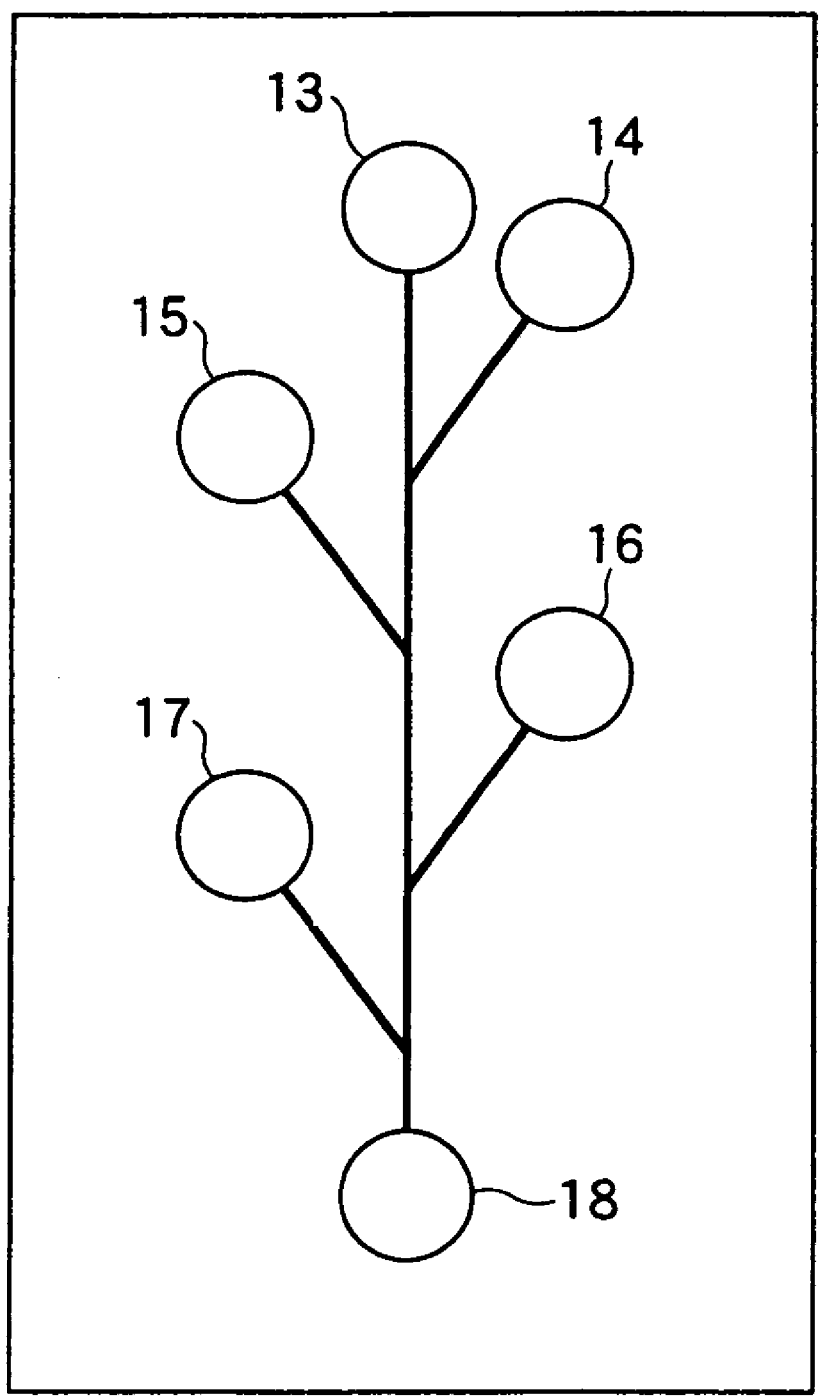
FIG. 14 is a diagram of a channel in which two or more reagents are merged at two or more merging points.

Using the method of the present invention, not only one object but also a plurality of objects in the sample can be measured by sharing of the channel, namely with a simple channel design (FIG. 14). That is, in the aforesaid illustrative example, the reagent 1 and the sample are made to react with each other for a necessary time, and then after a small time interval, the channel of the sample of a predetermined flow rate (not necessarily identical to the flow rate when mixed with the reagent 1) is merged with the channel of the reagent 3 flowing at another predetermined flow rate. Then, after reaction for a predetermined time, the reagent 4 is merged therewith and a product from reaction of the sample with the reagents 1, 2 is measured, and then a product from reaction of the sample with the reagents 3, 4 can be detected using the same detection channel.

When the amount of substances on the sample such as total cholesterol, triglyceride and bilirubin is directly determined, the product from reaction can be measured at a so-called endpoint, and detection may be carried out for only one point at the minimum. On the other hand, when the activity of enzymes in the sample such as GOT, GPT and γ-GTP in the blood, detection may be carried out for one point, but a plurality of measurements (detection) are preferably carried out over time in order to ensure high accuracy (rate assay).

In this case, detection may be carried out at plurality of points on the channel through which the final reaction mixture flows, namely at a plurality of points on the channel with distances from the point of merging with the final reagent (that is reaction time) being different. For this purpose, a plurality of detection systems may be placed on the channel of the final reaction mixture in the detector, or in case of one detection system, the detection system (optical system) or the chip may be shifted. The thermal lens detection system is shifted along the channel, or a plurality of thermal lens detection edges are placed on the channel, thereby making it possible to understand changes over time in a short time or instantly. That is, the channel length corresponds to the reaction time. This is difficult to implement for stereo chips that are overlaid three-dimensionally, but is easy to implement by combining the plane chip of the present invention with the high-sensitive thermal lens detector.

(Electrical Liquid Delivery)

In this applied invention, a variety of means such as mechanical pumps and electrical means may be adopted for liquid delivery since each fluid is mixed at a predetermined flow ratio. Among them, precise and simple liquid delivery controlling means includes electrical means such as electroosmotic flows as preferable configurations. Furthermore, in electrical means mentioned herein, voltage controlling means and current controlling means can be also used separately as necessary.

Methods in which liquid delivery is controlled by controlling voltage include a method in which an electrical field is applied to the liquid in the capillary to deliver liquid by means of the electrophoresis and electroosmotic flow (described in detail in "Capillary electrophoresis" Kodansha Co., Ltd., etc.). The electroosmotic flow is a method in which the liquid moves as ions on the inner surface of the capillary move, and in case the capillary is formed by glass and silicon, protons of silicic acid on the surface of glass, etc, provide the mobility power. Also, even in case a special kind of ion does not exist on the inner surface of the capillary in the chip made of organic polymer such as PMMA and PC, it is possible to have an electrolyte in the liquid adsorbed by the inner surface of the capillary and have the electroosmotic flow generated by the movement of the electrolyte, depending on the composition the liquid flowing in the capillary. To generate a stable electroosmotic flow, an organic polymer having sulfonic groups and carbonic groups may be added to the inner surface of the capillary by means of graft polymerization and the like.

In case of liquid delivery by the electroosmotic, the flow rate in each channel to be merged may be changed by changing the length and the size of the section of each channel, by changing the way of applying voltage to each channel, and by changing the charged condition of the inner surface of each channel capillary by the surface treatment.

Theoretically, the electroosmotic flow is proportional to $\zeta$ potential dependent on the material of the wall face of the capillary and potential difference applied to the capillary. To determine the velocity of the electroosmotic flow taking water at 20° C. as an example, when 100 V/cm is applied in a capillary having 75 mv of $\zeta$ potential, a value slightly more than 0.5 mm/sec is obtained for the velocity of the electroosmotic flow. No special functions are required for power sources for generating the electroosmotic flow, but considering the fact that potential difference larger of 1 kV or larger may be generated depending on the capillary length, power sources able to output high voltage (1 kV or higher) may be preferable. These high voltage power sources preferably have a capability to link directly or via an interface board and the like to an external computer for performing control. In that way, timing for applying potential difference to generate the electroosmotic flow and so forth is programmed, and more elaborate control of the electroosmotic flow can be performed. In the chip of the analyzer relating to the present invention, the sample is accurately controlled by means of the electroosmotic flow and/or electrophoresis, is put through separation and reaction with other reagents, and then is subjected to photothermal analysis at the downstream of the channel. Particularly, in terms of elaborate control, since the electroosmotic flow makes it possible to control the flow rate finely and in quick response by control of voltage and accurately in accordance with a set program, adoption of the electroosmotic flow is one of preferable embodiments for applications in which the flow ratio is elaborately controlled to carry out necessary chemical reactions.

Furthermore, methods in which a reaction product corresponding to the time after start of reaction is detected quantitatively such as a rate assay used for detection of organism originated substances using enzymes and the like may raise a problem in accurate measurements in case of liquid delivery by pumps causing velocity distribution in the section of the capillary. In the electroosmotic flow as described above, however, accurate detection is possible because the flow of liquid is in principle a laminar flow having no difference in velocity in the sectional direction of the capillary.

Also, a laminar flow protruding at the center of the flow is caused in the case using a pump, and difference in concentration of the substance between the tip and the root of the bump may be detected in the thermal lens detection method, but the fluid is made into a flat laminar flow and thus stable detection is possible by using the electroosmotic flow, which can also be listed as a feature.

In liquid delivery by pumps, however, by taking measures of promoting mixing and diffusion of liquid constituents by a baffle, etc. provided in the capillary and providing a channel length sufficient for enzyme reaction, etc. and so forth, accurate detection is also possible.

As power sources for generating electroosmotic flows, high voltage power devices (for example, Mode 1 HCZE-3OPNO, 25, Matsusada Precision-Co., Ltd. capable of up to 30 kV) are used, and these devices can be output-controlled from external computers via interface boards (for example, DAQCard-1200, CB-50 Connector Block, National Instruments Co., Ltd.). Programs for application timing of applying voltage, etc. can be made using, for example, NI-DAQ Drive Software, LabVIEW and the like.

Using the analyzer of this embodiment described above makes it possible to carry out bedside diagnosis in the medical work site and inform outpatients of examination results on the same day when they receive diagnosis, thus enabling selection of remedies and therapies based on the results to be made quickly. Also, quantitative and qualitative analyses of pollutants in the river and hazardous substances in wastes and the like can easily be carried out at polluted sites. Furthermore, pollution examination during customs clearance and immediate analysis at cooking sites are possible for imported foods.

Detection object substances include chemical substances, proteins, nucleic acids and the like without specific limitation, but environmentally polluting chemicals, biological substance in blood/cerebrospinal fluid/saliva and urine, biological substance originated from organs/tissues/mucosa, proteins such as bacteria and virus providing infectious sources, DNA, RNA, allergen and various kinds of antigens may be targeted.

Advantages of the present invention will be described further specifically using examples.

EXAMPLE 1

As an example of the present invention, the example in which quantitative measurement of total cholesterol in serum by the end point assay was carried out, controlling the flow of total three solutions that are a lipid measurement standard serum and two reagent solutions for detecting reaction from total cholesterol detection kit (product name: Cholesterol E-HA TESTWAKO (manufactured by Wako Chemical Co., Ltd.) will be shown. Liquid delivery was performed using the electroosmotic flow by application of voltage.

(Chip Making)

First, fabrication of a chip comprising a capillary will be described.

The absorbance of plate-like organic polymer bases was measured to predict influence on a thermal lens, providing basic data for selection the material of usable polymer bases. The measuring method and results will be described.

For measuring equipment, UV-2200A (UV-VIS Recording Spectrophotometry) manufactured by Shimadzu Co., Ltd. was adopted. For a measuring method, samples made of same materials that are different in thickness are prepared and cut in a size sufficient for covering an entire optical path, followed by erecting the sample on a measuring cell inserting portion so that the plate surface is perpendicular to the optical path without using a measuring cell. First, of the prepared plates made of same materials, two thinnest plates were used to make initial correction. For actual measurement, absorbance was measured using thinnest plates for reference and plates that were different in thickness as samples for measurement. For measuring wavelengths, three wavelengths of 488 nm, 633 nm and 780 nm were used. Details such as materials used will be described below.

(1) Samples for Measurement (a) Methacryl resin (Delpet 560 F: t=2 mm, 3 mm) manufactured by Asahi Chemical Industry Co., Ltd.

(b) Acrylicresin(Clarex:t=0.3 mm, 0.5 mm) manufactured by Nitto Jushi Kogyo Co., Ltd.

(c) Acrylicresin (Sumipex: t=4.5 mm, 10 mm) manufactured by Sumitomo Chemical Co., Ltd.

(d) Methacryl resin(Acrylite:t=2 mm, 5 mm) manufactured by Mitsubishi Rayon Co., Ltd.

(e) Polycarbonate resin (Panlite AD 5503: t=1 mm, 2 mm) manufactured by Teijin Chemical Co., Ltd.

(f) Methacryl resin (Deraglass A: t=2 mm, 3 mm) manufactured by Asahi Chemical Industry Co., Ltd.

(g) Polycarbonate resin (Eupilon/Sheet: t=0.5 mm, 1.0 mm, 2.0 mm) manufactured by Mitsubishi Engineering-Plastics Co., Ltd.

(h) Polycarbonate resin (PCSM PS600 t=0.5 mm, 1 mm) manufactured by Takiron Co., Ltd.

(i) Polycarbonate resin (Rectangle Plate: t=1 mm, 3 mm) manufactured by Takiron Co., Ltd.

(j) Polyester resin (PETEC PET6010: t=1 mm, 3 mm) manufactured by Takiron Co., Ltd.

(k) Polyvynil Chloride resin (ESS8800A t=1 mm, 3 mm) manufactured by Takiron Co., Ltd.

(l) Laminate film (MS Pouch: t=100 μm, 150 μm) manufactured by Meiko Shokai Co., Ltd.

(2) Measurement Results

A summary of measurement results is shown in FIG. 15. Furthermore, for bases of (a) to (l), the output by thermal lens detection was measured together. For measurement, excitation light and detection light were applied only to polymer bases to be measured and values at focal positions providing highest output by thermal lens detection were recorded. At this time, samples having thickness closest to the thickness of the real chip (2 mm) were measured, or measurements for two samples different in thickness were averaged.

Furthermore, for polycarbonate resin manufactured by Mitsubishi Engineering Plastic Co., Ltd. (g), variation in output by thermal lens detection due to measuring locations is significant and uneven distribution of substances such as micro crystals absorbing light can be predicted.

From the results shown in FIG. 15, it became evident that there is a correlation between absorptance (converted from absorbance) possessed by polymer bases in essence and obtained output by thermal lens detection. (Wavelength of excitation light of thermal lens detection: 633 nm).

When measurement was carried out, having xylene cyanol pigment (concentration of 5 μM) sandwiched between two glass plates as a reference measurement, the output by thermal lens detection was about 20 mV.

Then, a polycarbonate base having grooves on the surface was covered with the aforesaid laminate film (t=100 μm) manufactured by Meiko Shokai Co., Ltd., and xylene cyanol pigment (concentration of 5 μM) was to be measured in a similar way using a chip having grooves formed into a capillary, but 10 mv was detected as a background and precise measurement became difficult due to this background. From the above described measurements, the absorbance of the laminate film used is 0.0085 for t=50 μm (150 μm–100 μm), thus equaling about 4% for t=100 μm when converted to absorptance. In this case, however, a thermoset adhesive is used for the laminate film used, variation in background values that can be ascribed to its uneven distribution is observed. In the measurement of absorbance, however, since this variation is averaged, it is conceivable that partial absorptance is larger than 4%. Also, considering a possibility that a sample having higher concentration than the above described xylene cyanol pigment is measured, the acceptable absorptance of excitation light by the polymer base in case of measurement in this concentration range can be 5%. This value is a reasonable one if compared to the value evaluation described below.

The measurement value of 20 mV in the above described reference measurement is a quite standard value in measurement of biochemical substances measured in medical diagnosis and the like, and the value of 0.0005 is obtained as a value of absorbance when converted for a capillary with depth of 50 μm used in the measurement. In the thermal lens detector used in the present example, the lock-in amplifier output as a detection limit when using synthetic quartz considered as the most ideal transparent base material (background=0 mV) is about 0.5 mV. Thus, measurement of high sensitivity in which the concentration is further reduced by a factor of one to ten is possible, and imparting further high sensitivity to real measurement values is preferable in maintaining accuracy of a measuring system, regardless of whether medical diagnosis or not. As shown in FIG. 5, however, if the polymer base to be used for the chip itself have absorbancy for the excitation light and the like, output by the thermal lens detection is generated as a background, thus causing an error. Assuming that relative to 20 mV of thermal lens output for the above described xylene cyanol pigment (concentration of 5 μM), measurement is made for up to one-ten of the concentration, and that it is possible to accept up to ten times, desirably up to five times and further desirably up to two times as high as the signal from a measuring object substance as acceptable ranges of the background, the output would be 20 mV when accepting up to ten times, 10 mV when accepting up to five times and 4 ml when accepting up to two times. Looking at these values together with measurement values shown in FIG. 15, with a variation in measurement in consideration, the absorptance may be desirably 5% or less, preferably 2% or less, and further preferably 1% or less.

Further, a numerically reasonable value will be calculated. Assume that as a practical value, an object substance with absorbance in the range of 2 to 0.01 as value of absorbance converted when a cubette with optical path length of 1 cm is used is measured. This value equals 1 to 97.7% as transmittance and 99 to 2.27% as absorptance.

Assuming that absorption is performed uniformly along the optical path length, absorptance would be 0.495 to 0.011% for 50 μm of optical path length. Assuming that it is possible to accept up to ten times, desirably up to five times and further desirably up to two times as high as the signal from the measuring object substance as a background, and that decrease in thermal lens effect due to shift from the focal position of the excitation light is cut in half, values of 9.9 to 0.22% when accepting up to ten times, 4.95 to 0.11% when accepting up to five times and 1.98 to 0.044% when accepting up to two times would be obtained.

That is, these values show absorptance of the excitation light between its entrance and outgoing by the plate member forming the chip, which is accepted in case a substance with absorbance of 2 to 0.01 in a cuvette having optical path length of 1 cm is put in the capillary with depth of 50 μm to measure the same by thermal lens detection. Furthermore, it means that if absorptance of the excitation light between its entrance and outgoing by the chip comes to 10%, measurement of substances that can be measured by an absorptance meter using a cuvette of 1 cm becomes impossible even though it is possible to accept a maximum as background. Thus, the upper limit of the acceptable range of practical absorptance may be 2 to 5%. This value may be reasonable if compared to the relationship between the above described practical absorptance of the polymer base and the output by the thermal lens detection.

However, when measuring in the future a measurement substance having absorbance much higher than 2 converted for the case where the current cuvette having optical path length of 1 cm, the value of absorptance of acceptable resin polymers can be further increased. Furthermore, it is needless to say that even if the depth of the capillary is increased, similar effects are obtained and the absorptance of the accepted resin polymer can be increased.

Also, it is apparent that there is no influence of the above described background in case the optical axis of the detection light is largely shifted from the optical axis of the excitation light in a chip area.

Now, a method of fabricating a chip used for detection for an actual biochemical system will be described.

The plane plate member comprising the chip is molded with injection molding. The resin used for the injection molding is a methacryl resin (Delpet 560 F manufactured by Asahi Chemical Industry Co. Ltd.). As for gas, carbon dioxide with purity of 99% is used. SG 50 manufactured by Sumitomo Heavy Industries Co., Ltd. is used as a molding machine. Equipment shown in FIG. 16 is used as mold equipment.

Figure 16:
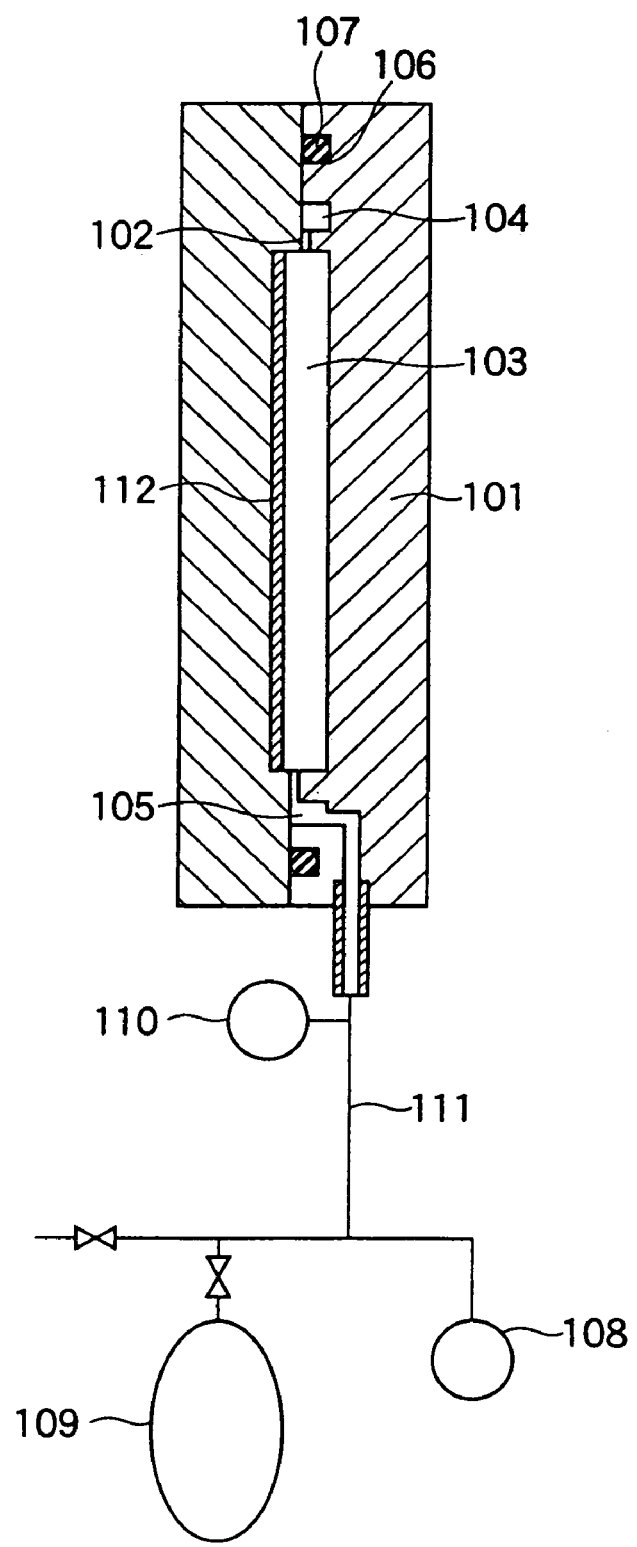
FIG. 16 is a diagram showing a cross section of mold equipment for molding the plate member made of organic polymer having on the surface the fine grooves in which the fluid flows.

In FIG. 16, around a mold cavity 103 of a mold 101 is a suction and exhaust slot 104 for suctioning and exhausting carbon dioxide from and to the mold cavity 103 through a gap 102 of a parting face, and such a suction and exhaust slot 104 is linked to a supply source of carbon dioxide through an out-of-mold aeration hole 105. Outside the mold cavity 103 exists an O-ring slot 106 for keeping the mold cavity 103 pressured in which an O-ring 107 is placed. The out-of-mold aeration hole 105 is linked to a carbon dioxide source 109 through a gas conductor 111. A pressure gage 110 and a safety valve 108 are coupled with the gas conductor 111.

Figure 17A:
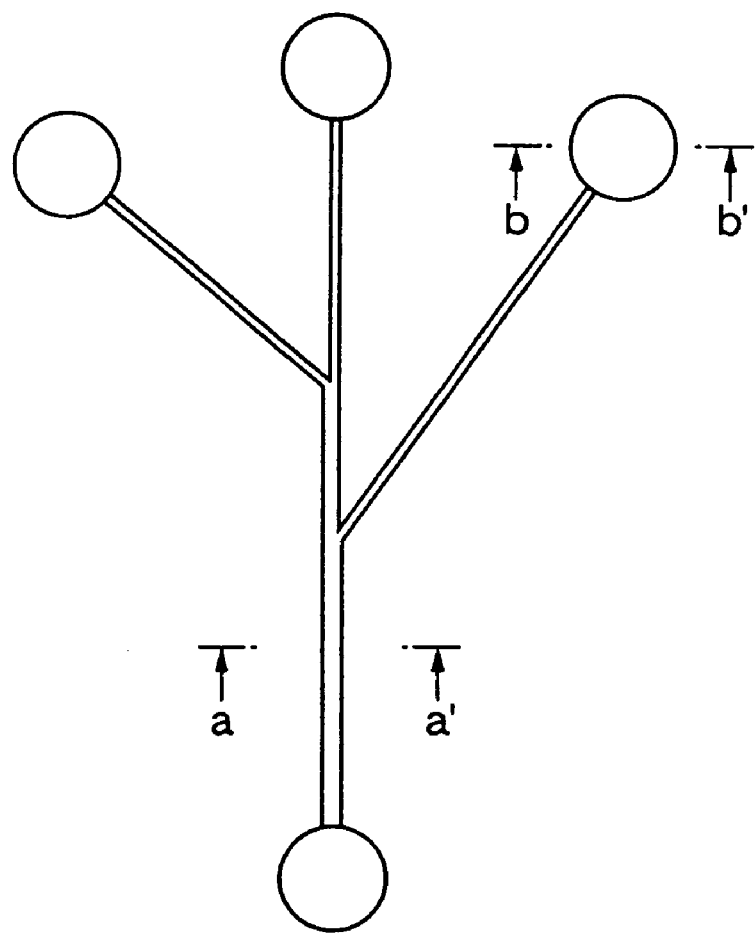
FIG. 17 is a plan view (a) showing a fine shape for molding (transferring) a channel consisting of grooves made on the mold surface portion of a mold for molding the plate member made of organic polymer having on the surface the fine grooves on which the fluid flows according to the present invention, and a sectional view (b) showing a shape of the cross section of the a–a' line of the fine shape, and a sectional view (c) showing the shape of the cross section of the b–b' line.
Figure 17B:
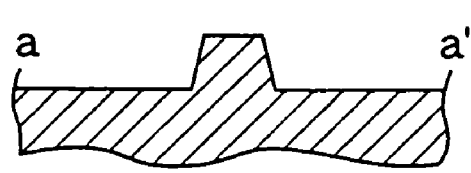
Figure 17C:
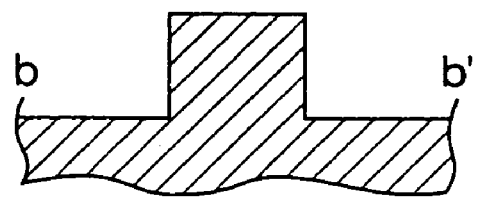

The mold surface is formed by an insert block or stamper 112, and the surface of such a nest or stamper 112 is processed into a fine shape of capillary. The fine shape is a shape shown in FIG. 17, and the shape of the groove of the cross section of the a–a' line is a trapezoid (bump) with width of 301 μm, depth of 50 μm and cross-sectional area of 14500 μm$^2$.

Resin is injected from a gate through a runner to the mold cavity 103.

The transformability of the condition of the mold surface is evaluated through observation with an optical microscope and shape measurement with a laser microscope.

Also, molded products are observed through observation with an optical microscope, observation of the shape of grooves of a cut section with an optical microscope and electron microscope, shape measurement with a laser microscope and the like.

Using the mold equipment shown in FIG. 16, carbon dioxide is charged into the mold with temperature of the mold cavity surface of 80° C. at pressure of 5.0 MPa. Then, methacryl resin with resin temperature of 240° C. is injected into the mold, the resin in the cylinder is kept at pressure of 80 MPa for ten seconds and is cooled for twenty seconds, and then a molded product is taken out. The carbon dioxide charged into the mold is released into the atmosphere concurrently with completion of filling of resin, and a plane plate member having grooves on the surface is molded.

The surface of the molded product obtained was smooth, and the transferred groove in the area corresponding to the cross section of the a–a' line of the stamper had width of 303.0 μm, depth of 49.7 μm and cross-sectional area of 14300 μm$^2$. Thus, the groove was transferred with accuracy of dimension within 2% for width and depth and within 4% for cross-sectional area.

Figure 18:
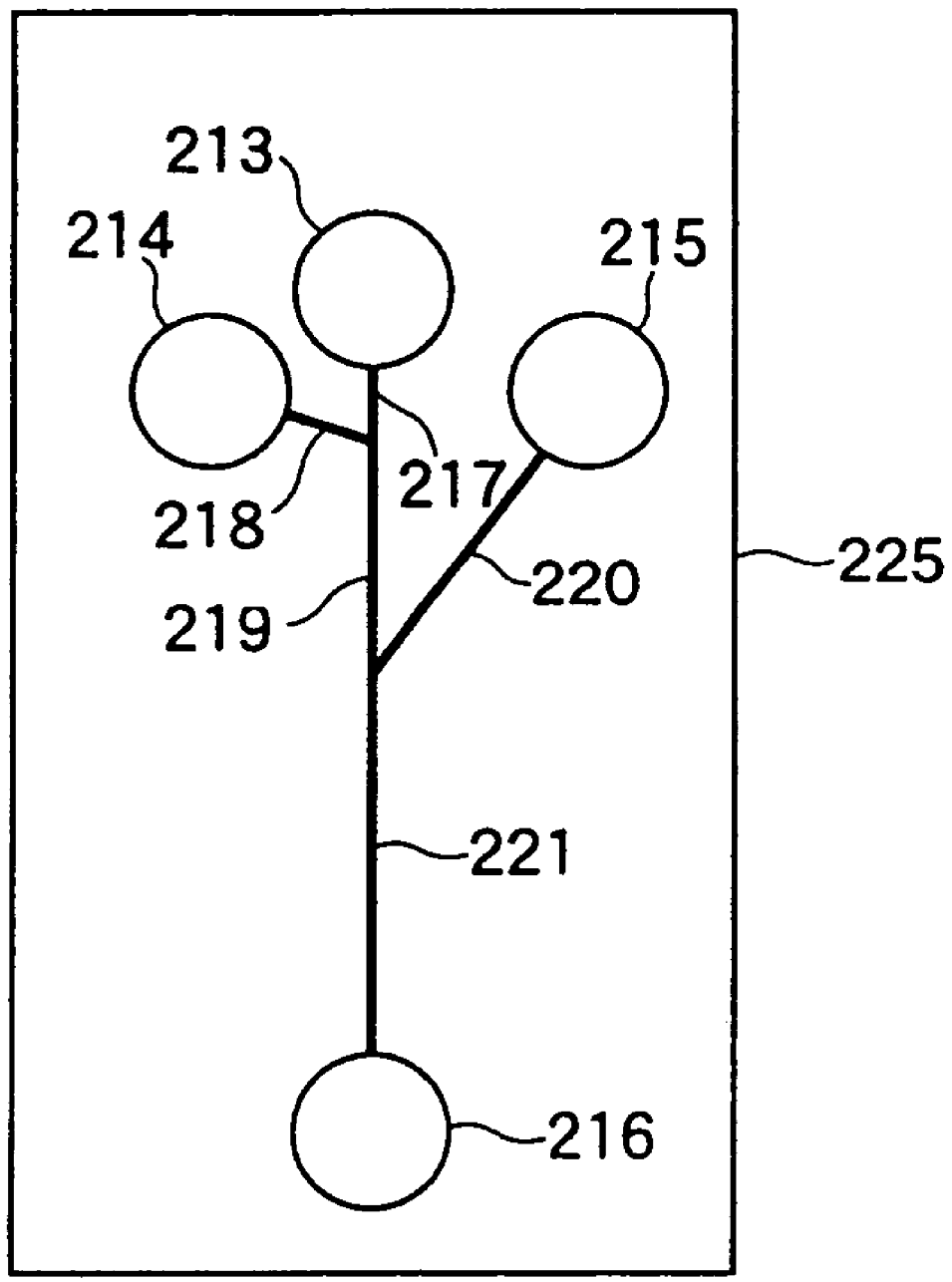
FIG. 18 is a diagram-2 showing a groove pattern of the plate member made of organic polymer having on the surface the fine grooves in which the fluid flows, which is molded by injection molding.

The molded plane plate member is 120 mm long and 80 mm wide and 2 mm thick, and is provided with grooves having patterns as shown in FIG. 18. Through-holes with diameters of 3 mm for reserving liquid are provided at four points, and a reservoir 213 is a reservoir for sample, a reservoir 214 is a reservoir for reagent 1, a reservoir 215 is a reservoir for reagent 2, and a reservoir 216 is a reservoir for wastes. The reservoir 213 is equipped with a filter for separation of blood cells, and when a sample (whole blood) is dropped, blood cells interrupting detection are removed and blood plasma is sent to the capillary. For the size of grooves, a groove 217 is 15 μm wide and 10 μm deep and 1 cm long, a groove 218 is 200 μm wide and 50 μm deep and 1 cm long, a groove 219 is 203 μm wide and 50 μm deep and 3 cm long, a groove 220 is 100 μm wide and 50 μm deep and 4 cm long, and a groove 221 (length between the merging point with the groove 220 and the detecting portion) is 303 μm wide and 50 μm deep and 5 cm long. This molded product is laminated with a methacryl resin sheet with thickness of 300 μm using a hot melt type adhesive to produce a chip.

Then, for the purpose of augmentation of the electroosmotic flow and cleaning, etc. of the inner surface of the capillary of the chip, the inside of the capillary is filled with 1N—NaOH solution (manufactured by Wako Chemical Co., Ltd.), and is heated at 60° C. for twenty four hours. After that, the inside of the capillary is washed with purified water (Kyoei Pharmaceutical Co., Ltd.) using pH as an indicator until neutralization is achieved and is dried.

Figure 19:
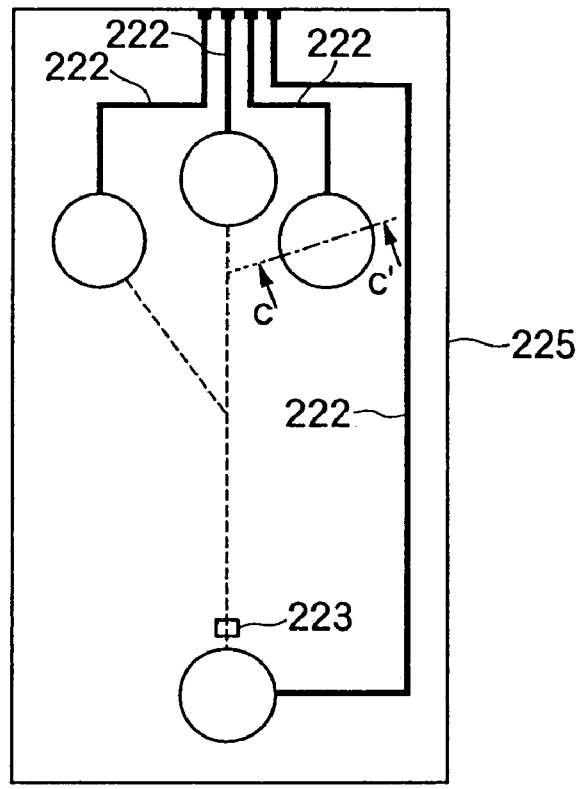
FIG. 19 is a diagram-2 showing a chip which is constituted by laminating a pair of plate members made of organic polymer, and on which a wiring, an electrode for trapping liquid and an electrode for connecting power terminals in detection equipment are printed with conductive ink.

Next, wiring and an electrode for connection of power source terminal in the detector are printed with a conductive ink (MSP-600F manufactured by Mitsui Chemical Co., Ltd.) containing silver particles on the opposite side (side with through-holes) of the plane plate member, and a platinum-plated eyelet made of brass is set as an electrode for reservoir to complete a chip (FIG. 19).

Figure 20:
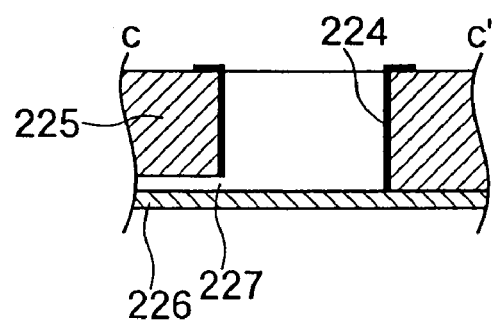
FIG. 20 is a sectional view of the c–c' of FIG. 19.

FIG. 20 is a sectional view of the c–c' line shown in FIG. 19. The analyzer is equipped with an electric power unit able to apply predetermined voltage to the reservoirs 213 to 216, a detector able to carry out detection by photothermal detection at a position indicated by a code of 223 of FIG. 19, and a printer to calculate measurements from detection data and output as well.

<Quantitative Determination of Total Cholesterol in Blood Serum>

(Preparation of Standard Serum)

The method of preparation of standard serum for measuring lipid by Kyowa Medix Co., Ltd. is partially modified, and standard serum is prepared. Specifically, one vial of freeze-dried product is dissolved using 851 μl of attached standard serum dissolving solution and is prepared so that total cholesterol equals 800 mg/dl as a calculated value, thus providing a stock solution. Then, the stock solution is diluted with attached standard serum solution to prepare solutions including 200 mg/dl and 50 mg/dl of total cholesterol as calculated values.

(Preparation of Detection Kit)

HA Test Wako Cholesterol E-HA Test Wako (Wako Chemical Industry Co., Ltd.) is used to follow an attached protocol.

(Detection of Total Cholesterol)

About 14 μl of buffer was dropped in the reservoir 216 to fill the entire capillary with buffer, followed by dropping about 14 μl of reagent 1 in the reservoir 214, about 14 μl of reagent 2 in the reservoir 215 and about 14 μl of sample in the reservoir 213. 100 V was applied to the electrodes of the reservoirs 213 to 215 against the reservoir 216, and an electroosmotic flow was generated from the reservoirs 213 to 215 to the reservoir 216. At this time, fine adjustments were made so that the flow rate in each groove was 1.5 nl/min in the groove 217, 100 nl/min in the groove 218, 101.5 nl/min in the groove 219, 50 nl/min in the groove 220 and 151.5nl/min in the groove 221. For measurement of the flow rate, the flow rate of non-polar beads (manufactured by Otsuka Electronics, φ: 520 nm) was measured for the purpose of convenience of experiments. Reaction between the sample and the reagent 1 requires three minutes, but the length of channel and applied voltage are set in advance so that the reaction is completed while the sample is mixed with the reagent to move in the groove. Similarly, reaction between the sample and the reagent 2 requires five minutes, but the length of the channel and applied voltage are set in advance so that the reaction is completed while the sample moves in the groove. The sample completing reaction was detected in the detecting portion 223 shown in FIG. 19 by the photothermal detection using a laser with wavelength of 633 nm for excitation light and a laser with wavelength of 780 nm for detect ion light as described later.

In case the volume of the channel needs to be corrected, a reservoir for standard samples is prepared in the vicinity of the reservoir 213 for samples in the chip, the standard sample together with the reagents 1, 2 is delivered, made to react and measured, and correction is made from the results.

Furthermore, for an electric power source to generate electroosmotic flows, a high voltage electric power source (Model HCZE-30PNO, 25, Matsusada Precision) was connected to an external computer, and voltage was controlled with this computer. At this time, the output of the high voltage electric power source was controlled via an interface board (DAQCard-1200, 1200CB-50 Connector Block, National Instrument), and programs for timing of application of voltage, etc. were created using software (N1-DAQ Drive Software, LabVIEW).

(Configuration of Photothermal Detector)

Figure 21:
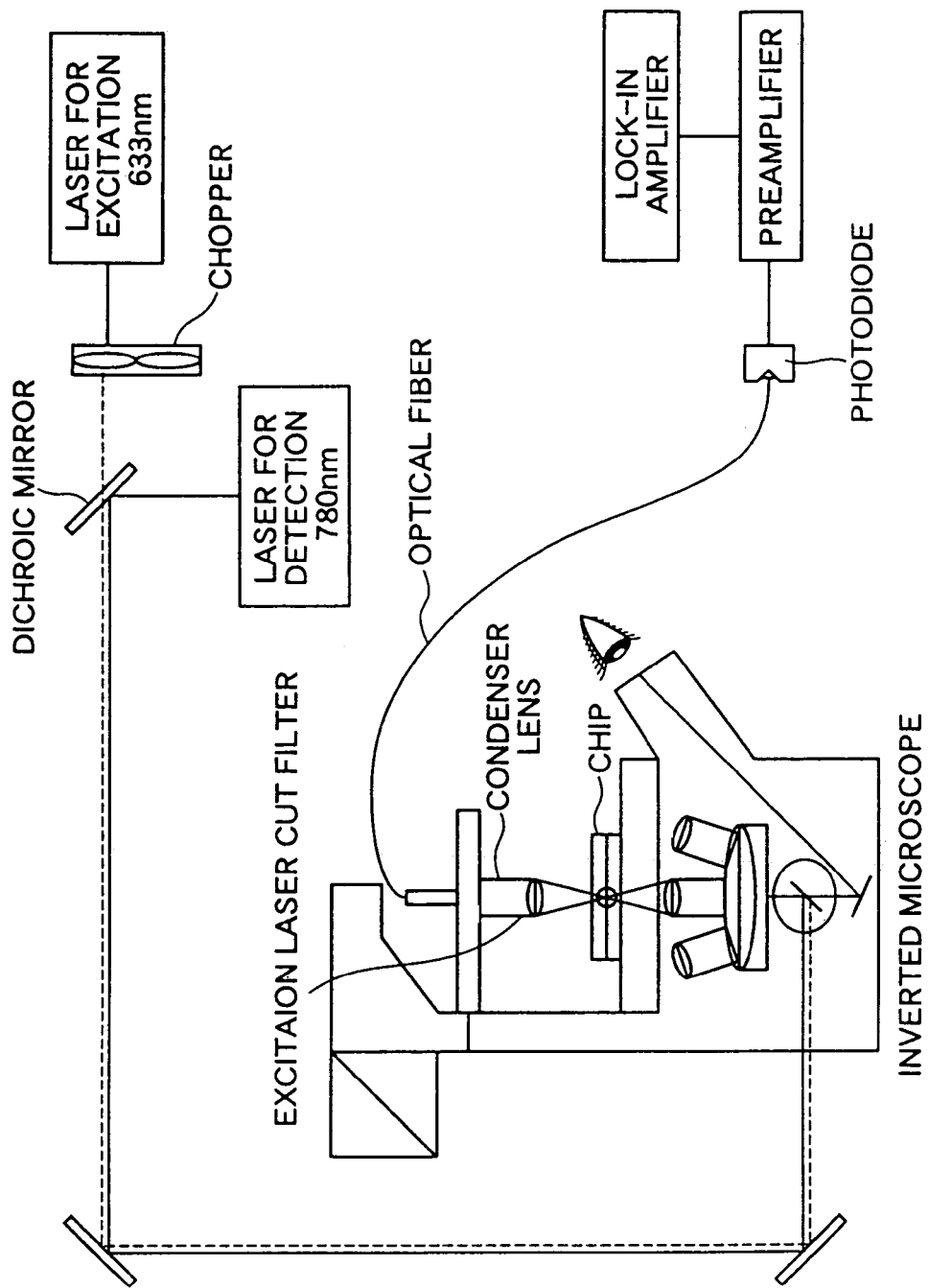
FIG. 21 is a schematic diagram of the thermal lens detection equipment used in the embodiment.

The detector based on the principle of photothermal conversion, which was used, is shown in FIG. 21 (details of optical parts are omitted). As for a microscope, an inverted microscope (IX70, manufactured by Olympus Co., Ltd.) was used, considering ease of handling of samples on the stage. This may be a falling type microscope. This microscope is already modified so that laser beams made to be coaxial can be introduced. As for lasers, a He—Ne laser (633 nm, 10 mW, manufactured by Edmund Scientific) was used for excitation, an infrared semiconductor laser (780 nm, 15 mW, DL-4034-151 manufactured by Sanyo Electric Co., Ltd.) for detection. For these lasers, lasers with appropriate frequency may be used depending on reagents used and the absorption spectrum of resulting reactants.

The type of lasers includes gas, solid and semiconductor types without limitation. For optical systems such as mirrors and beam expanders, products manufactured by Melles Griot Co., Ltd. were exclusively used. The laser beam for excitation is modulated by a light chopper, and is then made by a dichroic mirror to be coaxial with the laser beam for detection, and is guided to the microscope to be applied to the sample.

After the laser beam is applied to the sample, among the excitation light and the detection light made to be coaxial, the excitation light is removed by a filter and the detection light is guided to a photosensor. For elements of a laser beam receiving portion, a photosensor amplifier with fiber (C6386, manufactured by Hamamatsu Photonics Co., Ltd.) was used considering convenience of handling. The light receiving portion of this photosensor is covered with a cover having a pinhole. The outputs from the photosensor and the sensor amplifier are amplified with a low-noise preamplifier (LI-75A, manufactured by NF Circuit Block Co., Ltd.), and then is guided to the lock-in amplifier for signal processing.

Procedures for detecting the condition in the capillary using this detector are as follows. As shown in FIG. 21, first, the chip is put on the stage of the inverted microscope. For focusing of the objective lens, focusing at the positions of the upper edge and lower edge of a capillary pattern was carried out while referring a monitor screen, using a laser for excitation, and then the midpoint between upper and lower edges of the capillary pattern is defined as the center position of the capillary to achieve focussing.

Furthermore, as described above, when the capillary depth is in the range of 50 μm to 100 μm, the objective lens may be adjusted in the range of NA=0.2 to 0.8, the numerical aperture may be selected from the numbers of 0.2, 0.4 and 0.6 such that optimal sensitivity can be obtained. In the present example, however, the depth of the capillary is 50 μm, the highest concentration sensitivity was obtained using the thermal lens detection when using an objective lens with the numerical aperture of 0.4. In this condition, in order to ensure that a sufficiently effective value is obtained and that stray light of the excitation light does not exist in the light detector, a check is made to see that the output by the aforesaid thermal lens detection is adequately reduced under the condition that only the excitation light is let in. Next, the convergent angle of the beam expander of the detection light is adjusted to the position such that a maximum signal is provided, while looking at the output by the thermal detection.

Figure 22:
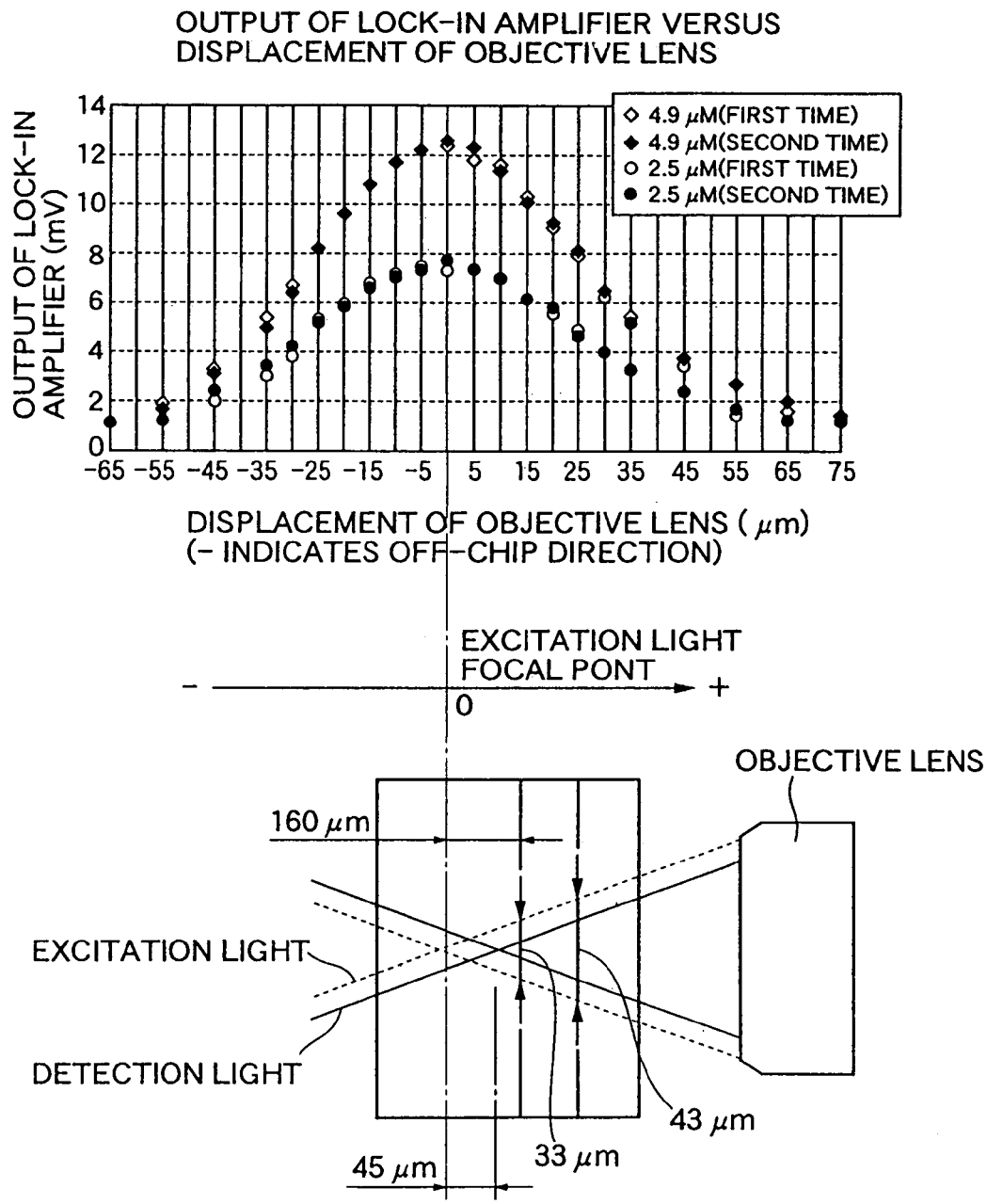
FIG. 22 is a diagram showing relationship between the laser focus position relative to the capillary of the thermal lens detection equipment and the output in the thermal lens detection method.

At this time, in order to determine an optimal focal position for the present example, the chip was put on a X-Z stage (manufactured by Sigma Koki) allowing the chip to be controlled by unit of μm in the Z direction, and the change of the output by the thermal detection when making the chip to shift in the Z direction was examined. The result is shown in FIG. 22. In case of the present example, since emphasis is put on the concentration sensitivity in a certain area rather than measurement in an ultramicro area, the focal point of the excitation light is not necessarily equal to the center of the capillary. In terms of concentration sensitivity, this excitation is more advantageously applied in the direction covering the entire capillary, but if the excitation is excessively spread in contrast, the intensity of the excitation light in a measuring area is reduced and heat diffusion affect the thermal lens detection output to be weakened, so an optimal value exists. In case of the present example, as shown in FIG. 22, output by the thermal lens detection is obtained in the range of ±50 μm around the focal position of the excitation light, namely a position at the distance of 160 μm from the capillary in the plane plate member opposite to the capillary when viewing from the irradiation side. This optimal value is obviously varied depending on the width and depth of the capillary, it is still preferable that the temperature varying area is broadened in order to enhance the concentration sensitivity.

After focussing is implemented, the sample and reagent are introduced into the chip, mixing and reaction of the sample and reagent are carried out, and the solution containing a reaction product is guided to the detecting portion, as described above.

The laser for excitation is modulated with a light chopper to, for example, 116 Hz, and then the reaction product contained in the solution flowing in the detecting portion is excited to produce heat. The frequency of the modulation by this light chopper could be changed due to the SN ratio and the like. Since the focal position of the laser for detection is shifted due to the thermal lens generated by this heat production, and thus the quantity of received light of the photosensor through pinholes varies depending on the heating values, a predetermined component contained in the sample can be analyzed from this variation.

Although the flow of the sample may be either stopped or continued during measurement, measurement was carried out after stopping the flow of the sample in the present example. The signal from the photosensor is processed by the lock-in amplifier, using one second as a time constant in this case, only signals having the same frequency as the light chopper, 116 Hz, were selectively used as output. The output voltage of the lock-in amplifier is proportional to the concentration of the reaction product excited by the excitation light, thus making it possible to quantify the reaction product.

For the result of the present example, a calibrated curve was created from five measurements using standard serums containing 800 mg/dl and 50 mg/dl of total cholesterol. The measurement of standard serums containing total cholesterol equating to 200 mg/dl is carried twenty times, and 3% of CV value was obtained. From the above described result, total cholesterol in the sample could be detected with good repeatability using such a "analyzer".

EXAMPLE 2

As one example of the present invention, an example in which total two solutions of standard serum and a reactant reagent obtained by modifying an aspartic aminotransferase (GOT) activity measurement kit (TA-LN Kainos (Kainos Laboratories Inc.)) were flow-controlled to perform quantitative determination aspartic aminotransferase (GOT) in the serum that is measured by a rate assay will be shown. Because of the rate assay, reaction stop solution was not used.

(Fabrication of Analyzer Including Chips)

Figure 23:
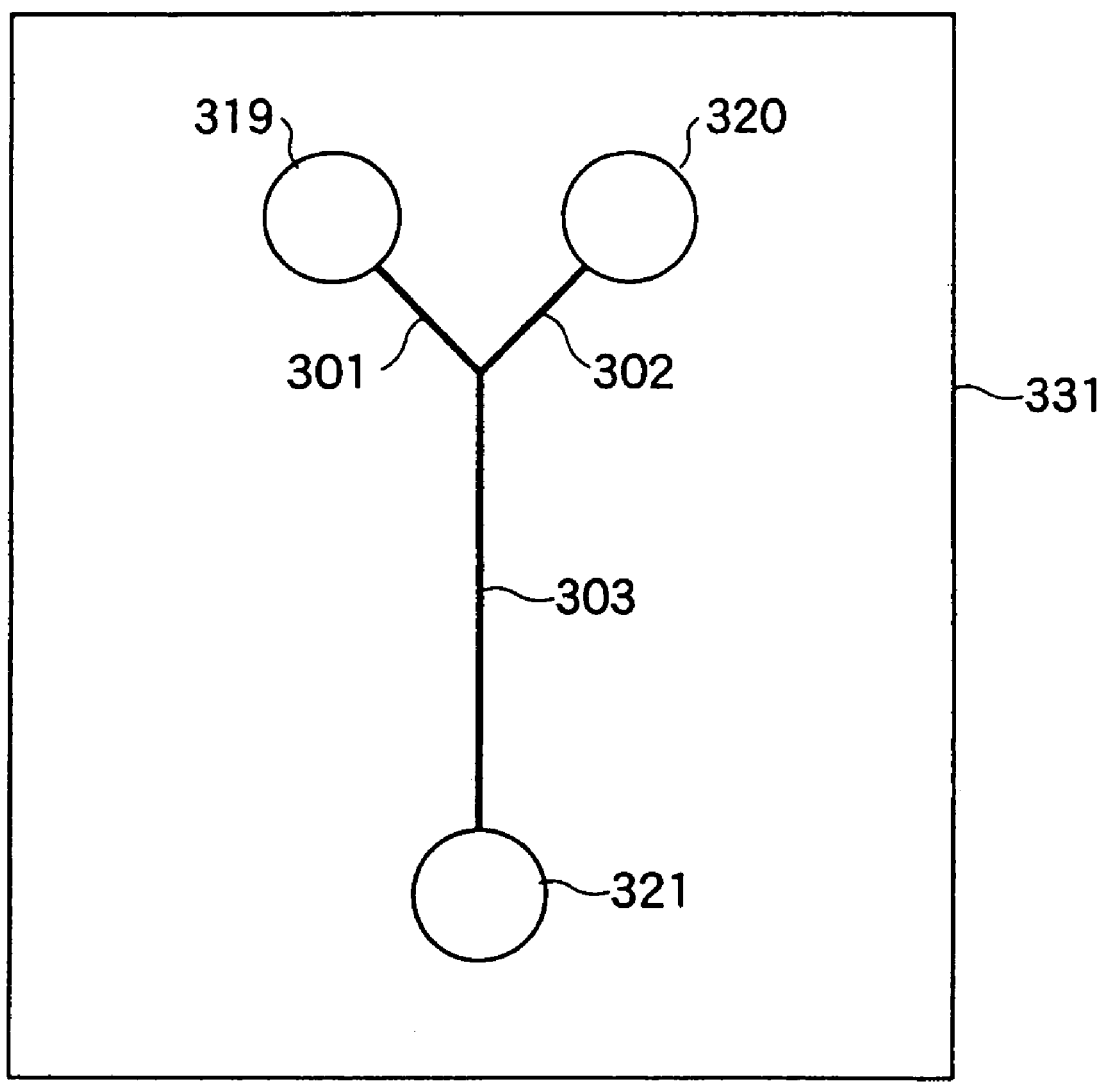
FIG. 23 is a diagram-3 showing a groove pattern of the plate member made of organic polymer having on the surface the fine grooves in which the fluid flows, which is molded by injection molding.

First, a chip is molded with injection molding in the same way as Example 1, except that modification is made such that the pressure at which carbon dioxide is charged into the mold is 2.0 MPa, 70 NHX is used as methacryl resin, and the nest and stamper having a pattern shown in FIG. 23 is used in Example 1.

The plane plate member configuring the chip is 12 cm long and 8 cm wide and 2 mm thick, and has grooves of a pattern as shown in FIG. 23 formed thereon. Through-holes with diameter of 3 mm for reserving liquid are provided at three points, reservoirs 319, 320 and 321 are reservoirs for the sample, reagent 1 and waste 2, respectively. The reservoir 319 is equipped with a filter for separation of blood cells, and when a sample (whole blood) is dropped, blood cells interrupting detection are removed and blood plasma is sent to the capillary. For the size of grooves, a groove 301 is 30 μm wide and 30 μm deep and 1 cm long, a groove 302 is 30 μm wide and 30 μm deep and 1 cm long, and a groove 303 is 60 μm wide and 30 μm deep and 5 cm long.

Next, for the purpose of cleaning, etc. of the inner surface of the capillary of the chip, the inside of the capillary is filled with 1N—NaOH solution (Wako Chemical Co., Ltd.), and is heated at 60° C. for twenty four hours. After that, the inside of the capillary washed with purified water (Kyoei Pharmaceutical Co., Ltd.) using pH as an indicator until neutralization achieved, and is dried.

Figure 24:
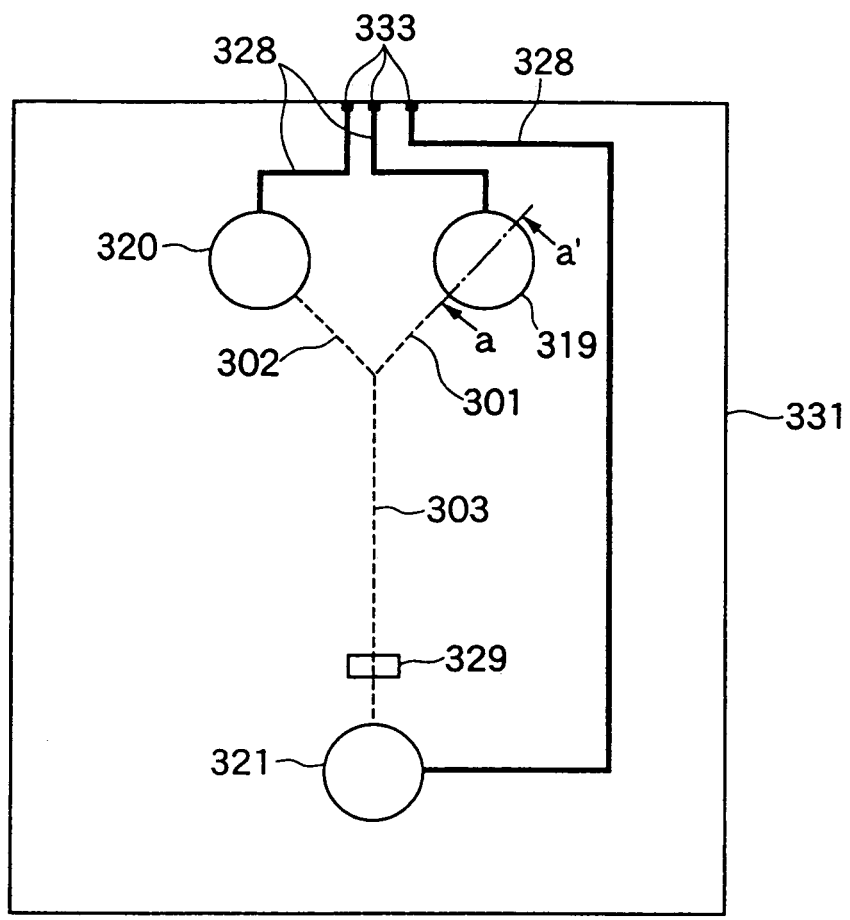
FIG. 24 is a diagram-3 showing a chip which is constituted by laminating a pair of plate members made of organic polymer, and on which a wiring, an electrode for trapping liquid an electrode for connecting power terminals in detection equipment are printed with conductive ink.

This plane plate member is laminated with a PMMA covering plate (plane plate member) having same size as the aforesaid plane plate member and thickness of 200 μm using adhesive to form a capillary. Then, in order that it can also be used for electrification for liquid delivery, wiring, electrodes for liquid reservoirs and an electrode for connection of power source terminals are printed with a conductive ink (MSP-600F, manufactured by Mitsui Chemical Co., Ltd.) containing silver particles on the opposite side (side with through-holes) of the plane plate member to complete a chip for analysis (FIG. 24). The reservoir is formed into a shape of taper so that printing can be made on the inner wall without tilting the chip.

Figure 25:
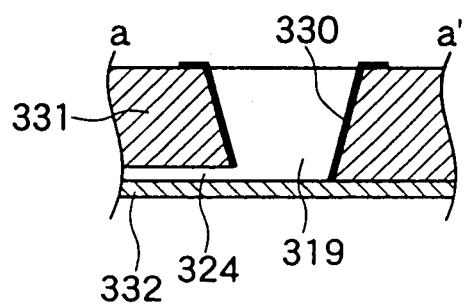
FIG. 25 is a sectional view of the a–a' of FIG. 24.

FIG. 25 is a sectional view of the a–a' in FIG. 24. The analyzer is equipped with electric power units able to apply predetermined voltage to the reservoirs 319 to 321. These electrodes units are not used in the Example 2, but are used in Example 4 in which the electroosmotic flow is used as liquid delivering means. Also, it is equipped with a detector so that detection can be made using the photothermal detection at the position of 329 in FIG. 24, and further with a printer to calculate measurement results from detection data and output as well.

(Preparation of Detection Kit)

As a detection kit, TA-LN Kainos (Kainos Laboratories Inc.) that we had asked Kainos Laboratories Inc. to manufacture in a special manner and purchased was used. The kit was different from off-the-shelf products in that a solution of sodium 3,5-dimethoxy-N-ethyl-N-(2-hydroxy-3-sulfopropyl)-aniline (DAOS) (Dojin Chemical Laboratory Co., Ltd.) dissolved in a detecting reagent made by removing only sodium N-ethyl-N-(2-hydroxy-3-sulfopropyl)-m-toluidine (TOOS) from the GOT substrate buffer so as to be in a concentration of 10 mM was used as the GOT substrate buffer.

Then, one vial of GOT reactant reagent is dissolved in 8 ml of GOT substrate buffer to provide a reagent 1. This operation was performed so that the mixing ratio of the reagent 1 with diluted serum described later was 1:1. Also, a reaction stop solution for use in the standard protocol of TA-LN Kainos was unused because of detection by the rate assay.

(Preparation of Standard Serum)

In the present example, serum was used instead of whole blood.

The preparation method of Suitrol A (manufactured by Nissui Pharmaceutical Co., Ltd. was partially modified to prepare a standard serum. Specifically, one vial of freeze-dried product was dissolved using 1174 µl of purified water (manufactured by Kyoei Pharmaceutical Co., Ltd.) and preparation was made so that the activity of GOT equaled 600 Karmen unit (KU) as a calculated value to provide a stock solution. Then, the stock solution was diluted with purified water (manufactured by Kyoei Pharmaceutical), and serum solutions (hereinafter referred to as GOT dilute serums) including GOTs showing 300 KU, 150 KU and 75 KU of activity as calculated values were prepared. Furthermore, 75 KU, 150 KU and 300KU of GOT dilute serums that had been already modified were diluted with the GOT substrate buffer of modified TA-LN Kainos by a factor of 26 in volume and were used for GOT detection evaluation. In other words, solution with 250 µl of modified GOT substrate buffer added to 10 µl of the GOT dilute solution was prepared.

(Detection of GOT)

At the edge of the top of the Y-shaped capillary, microsyringes (manufactured by Hamilton Co., Ltd.) in which the reagent 1 and the dilute serum were placed, respectively were coupled using Teflon tube and a rubber stopper.

Solution for use was preheated in advance to 37° C., the microsyringe was fitted to a syringe pump (manufactured by Harvard Co., Ltd.), and the solution was delivered.

At this time, the flow rate in each groove was 1.5 nl/min in the groove 301, 1.5 nl/min in the groove 302 and 3.0 nl/min in the groove 303.

Measurements were made from the region with reaction completed to each reaction progressing point by scanning at a fixed speed from the reservoir 321 towards the merging point of the reservoir 319 and reservoir 320 with the photothermal detection using 633 nm of wavelength for excitation light and 780 nm of wavelength for detection light.

That is, the point of measuring concentration with the photothermal detection is moved at the speed of 1.5 cm/sec along the groove. Specifically, positioning was made precisely by recognizing a positioning mark placed near the groove after one second of movement, focusing was achieved visually, and detection was carried out with the photothermal at each measuring point for ten seconds. That is, in the example, the rate of change in detection values characteristic of the rate assay can be detected in a short time depending on intervals of positioning marks being placed.

In case the volume of the channel needs to be corrected, a reservoir for a standard sample is prepared in the vicinity of the reservoir for the sample in the chip, a standard sample together with the reagent 1 is delivered, made to react and measured before or after the measurement of the sample, and correction is made from the result.

(Configuration of Photothermal Detector)

For a detector based on principle of photothermal conversion, a detector same as that in Example 1 was used (FIG. 21).

As for a microscope, an inverted microscope (IX70, manufactured by Olympus Co., Ltd.) was used, considering ease of handling of samples on the stage. This may be a falling type microscope. This microscope is already modified so that laser beams made to be coaxial in the optical system outside the microscope can be introduced. As for lasers, a He—Ne laser (633 nm, 10 mW, manufactured by Edmund Scientific) was used for excitation, an infrared semiconductor laser (780 nm, 12 mw, DL-4034-151 manufactured by Sanyo Electric Co., Ltd.) for detection. For these lasers, lasers with appropriate frequency may be used depending on reagents for use and the absorption spectrum of resulting reactants.

The type of lasers includes gas, solid and semiconductor types without limitation. For optical systems such as mirrors and beam expanders, products manufactured by Melles Griot Co., Ltd. were exclusively used. The laser beam for excitation is modulated by a light chopper, and is then made by a dichroic mirror to be coaxial with the laser beam for detection, and is guided to the microscope to be applied to the sample.

After the laser beam is applied to the sample, among the excitation light and the detection light made to be coaxial, the excitation light is removed and the detection light is guided to a photosensor. For elements of a laser beam receiving portion, a photosensor amplifier with fiber (C6386, manufactured by Hamamatsu Photonics Co., Ltd.) was used considering convenience of handling. The light receiving portion of this photosensor is covered with a cover having a pinhole. The outputs from the photosensor and the sensor amplifier are amplified with a low-noise preamplifier (LI-75A, manufactured by NF Circuit Block Co., Ltd.), and then is guided to the lock-in amplifier for signal processing.

Procedures for detecting the condition in the capillary using this detector are as follows. As shown in FIG. 21, first, the chip is put on the stage of the inverted microscope. The sample and reagent are introduced into the chip, mixing and reaction of the sample and reagent are carried out as described above. For implementation of measurement positioning is made precisely by moving the stage at the speed of 0.5 cm/sec and recognizing a positioning mark placed near the groove after one second of movement. For focusing of the objective lens, focusing at the positions of the upper edge and lower edge of a capillary pattern was carried out while referring a monitor screen, using a laser for excitation, and then the midpoint between upper and lower edges of the capillary pattern is defined as the center position of the capillary to achieve focussing.

The laser for excitation is modulated with a light chopper to 114 Hz, and then the reaction product contained in the solution flowing in the detecting portion is excited to produce heat. The frequency of the modulation by this light chopper could be changed due to the SN ratio and the like. Since the focal position of the laser for detection is shifted due to the thermal lens generated by this heat production, and thus the quantity of received light of the photosensor through pinholes varies depending on the heating values, a predetermined component contained in the sample can be analyzed from this variation.

The signal from the photosensor is processed by the lock-in amplifier, using one second as a time constant in this case, only signals having the same frequency as the light chopper, 114 Hz were selectively used as output. The output voltage of the lock-in amplifier is proportional to the concentration of the reaction product excited by the excitation light, thus making it possible to quantify the reaction product.

For the result of the present example, a calibrated curve was created from five measurements using standard serums containing GOTs showing 300 KU and 75 KU of activity, and measurement of GOT dilute serum showing GOT activity equal to 150 KU was performed twenty times, and the CV value of 1% was obtained. From the above described result, the GOT in the sample could be detected with good repeatability using such an "analyzer".

EXAMPLE 3

Measurement of total cholesterol was carried out using a photothermal detector similar to that in Example 2, and using a Y-shaped channel chip made of PMMA (FIG. 23) made by injection molding as in case of Example 2, except that an Ar laser having an emission at 488 nm was used for the detection light. The groove width and depth of the Y-shaped channel of such a chip are 200 μm and 50 μm, respectively. Cholesterol E-Test Wako manufactured by Waco Chemical Co., Ltd. was used as a reagent. Microsyringes (manufactured by Hamilton Co. Ltd.) in which a coloring reagent and dilute standard serum respectively were coupled with the both edges of the top of the Y-shaped channel using a Teflon tube. Preparation was made so that the reagent concentration equaled a concentration defined for the reagent kit when the coloring reagent was mixed with the dilute standard serum at the flow ratio of 1:1. That is, the coloring reagent was dissolved using a half of the defined quantity of buffer, and a standard serum prepared using a method in accordance with Example 1 was diluted with the buffer by a factor of 75 times. A syringe pump (manufactured by Harvard Co., Ltd.) was used for liquid delivery, flow rates of each coloring reagent and dilute standard serum were equated, the flow velocity was adjusted so that reaction time after mixing was three minutes, and the solution was pumped towards the waste reservoir at the lower side of the Y-shaped channel. A copper plate and a sheet heater were placed under the chip and adjustments were made with a thermostat and a temperature controller so that the temperature was kept at 30° C.

Figure 26:
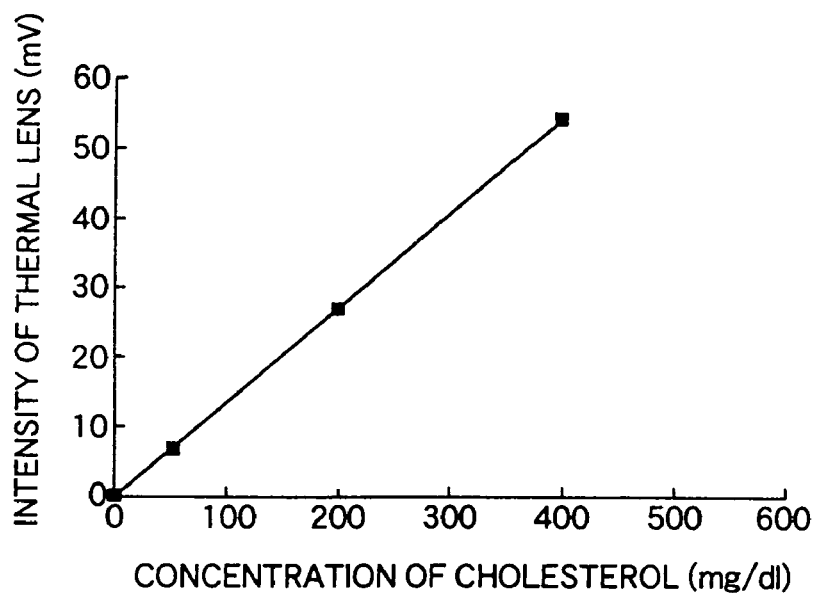
FIG. 26 is a diagram showing relationship between the concentration of cholesterol and the output in the thermal lens detection method in Example 3.

The result of the measurement of output by the thermal lens detection is shown in FIG. 26.

EXAMPLE 4

Reaction for detection of total cholesterol was carried out using equipment and a chip similar to those in Example 3, except that the electroosmotic flow was used as a method of liquid delivery and Cholesterol E-HA Test Wako of Waco Co., Ltd. was used as a detecting reagent. At each edge of the Y-shaped channel (FIG. 23), a cylindrical reservoir whose height and diameter was about 6 mm and 4 mm, respectively, was placed on the chip surface at the side opposite to grooves via a through-hole. Then, for the purpose of augmentation of the electroosomotic flow and cleaning, etc. of the inner surface of the capillary of the chip, the inside of the capillary is filled with 1N—NaOH solution (Wako Chemical Co., Ltd.), and is heated at 60° C. for twenty four hours. After that, the inside of the capillary washed with purified water (Kyoei Pharmaceutical Co., Ltd.) using pH as an indicator until neutralization achieved, and is dried.

Then, the plane plate member is laminated with a covering plate (plane plate member) having same size as the aforesaid plane plate member and thickness of 200 μm using adhesive to form a capillary. Then, in order that it can also be used to supply electric potential for liquid delivery, wiring, electrodes for liquid reservoirs and an electrode for connection of power source terminals are printed with a conductive ink (MSP-600F, manufactured by Mitsui Chemical Co., Ltd.) containing silver particles on the opposite side (side with through-holes) of the plane plate member to complete a chip (FIG. 24). Furthermore, the reservoir is formed into a shape of taper so that printing can be made on the inner wall without tilting the chip.

FIG. 25 is a sectional view of the c–c' in FIG. 19.

The enzyme solution A and the dilute standard serum prepared with a method in accordance with Example 1 were mixed in advance and made to react at 37° C. for five minutes, and were then put in the reservoir 319 at the upper side of the Y-shaped channel. Then, the enzyme solution B is put in the reservoir 320 at another end of the upper edge. Preparation was made so that the concentration of the reagent equaled a concentration defined for the reagent kit when the solution in the reservoir 319 was mixed with the solution in the reservoir 320 at the ratio of 1:1. The lower end of the Y-shaped was used as a waste reservoir, the channel and the waste reservoir were filled with a buffer for dissolution of the enzyme solution A attached with the reagent kit, and the height of the liquid level was adjusted so that difference in the liquid level for each reservoir was eliminated. A platinum wire electrode was put in each reservoir, voltage was applied to the electrodes of the reservoir 319 for the sample and enzyme solution A and those of the reservoir 320 for the enzyme solution B while keeping the waste reservoir at 0 V, with the condition of forming 25 V/cm of potential gradient as basics, and the voltage was adjusted so that the ratio of the flow rate from the reservoir 319 to the reservoir 321 to the flow rate from the reservoir 320 to the reservoir 321 was 1:1.

As for temperature, the room temperature (26° C.) was adopted for the convenience of experiments.

Figure 27:
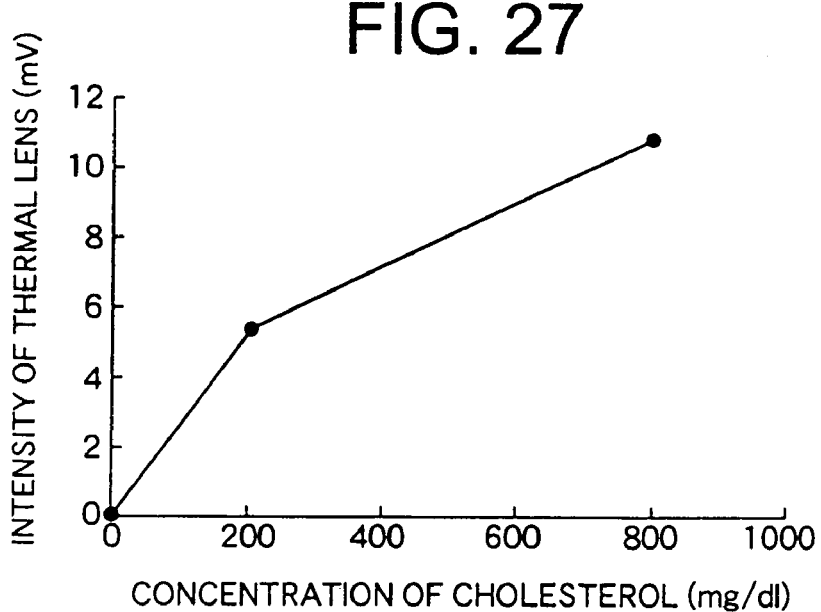
FIG. 27 is a diagram showing relationship between the concentration of cholesterol and the output in the thermal lens detection method in Example 4.

The result of the measurement of output by the thermal lens detection is shown in FIG. 27.

INDUSTRIAL APPLICABILITY

The analyzer of the present invention is an analyzer composed of a chip made of organic polymer having fine capillaries through which fluid flows, with good mass-producibility and handling property and a photothermal detector that has high sensitivity and is easily downsized, thus making it possible to provide an analyzer that is excellent in disposability of chips, is capable of analyzing inexpensively, simply and in a short time, and is suitable for POC analyses, etc.

The invention claimed is:

1. A method of analyzing a fluid sample or a fluid sample and a fluid reagent and for analyzing a predetermined component in the sample or a mixed fluid of the sample and the reagent, the method comprising:
   forming a chip at least partially made of an organic polymer and provided with a capillary to allow the fluid sample or the fluid sample and the fluid reagent to flow through the capillary,
      wherein the forming includes providing a pair of laminated plane plate members, each plate having at least an inner and an outer side, at least one of the plate members comprising a groove on a plate surface and at least one of the plate members being made of an organic polymer, the plate surface comprising the groove formed on the inner side of the at least one of the plate members, wherein the respective inner sides of the laminated plane plate members are fused together to form the chip including the capillary; further providing a photothermal conversion detector including an excitation light and detection light;

emitting the excitation light and the detection light from the photothermal conversion detector, such that the detector irradiates the component with the excitation light along a direction perpendicular to a flow direction of the fluid sample or the fluid sample and the fluid reagent through the capillary, and measures a change in a thermal lens effect in the component due to a measured change of temperature associated with the fluid sample or the fluid sample and the fluid reagent inside the capillary; and measuring an enlarged thermal lens effect exhibited from the groove that is equivalent to approximately the cross-sectional area of the groove, such that the chip does not substantially cause a photothermal conversion effect by absorbing the excitation light.

2. The method according to claim 1, wherein absorptance of the excitation light by the plate members is measured at 5% or less.

3. The method according to claim 1, wherein the measured change of temperature inside the capillary occurs in a range such that a concentration sensitivity sufficient for analyzing the predetermined component is obtained from a condensed degree of the excitation light.

4. The method according to claim 3, further comprising providing a numerical aperture of an objective lens located on a light-irradiating side of the capillary for irradiating the capillary with the excitation light.

5. The method according to claim 1, further comprising connecting the capillary to a sample channel through which the sample flows and to a measurement channel where the measurement is carried out, and further connecting the capillary to at least one reagent mixing means between the sample channel and the measurement channel;

wherein the reagent mixing means is formed by at least one reagent channel through which a reagent flows, a merging point where a fluid coming from the sample channel and the reagent coming from the reagent channel are merged, and a mixing channel provided downstream of the merging point, in which the fluid coming from the sample channel and the reagent coming from the reagent channel are mixed at a predetermined ratio and are made to react for a predetermined time; and adjusting a flow rate in the sample channel and the reagent channel in accordance with the mixing ratio.

6. The method according to claim 5, further comprising flowing the sample and the reagent continuously in the capillary, and providing a mixing channel that is long enough for the fluid merged at the merging point just before the mixing channel to flow at a predetermined flow rate for a time required for completing a predetermined mixing and reaction.

7. The method according to claim 1, further comprising applying a voltage to the fluid sample, or to the fluid sample and the fluid reagent separately, thereby making the fluid sample or the fluid sample and the fluid reagent flow.

8. The method according to claim 1, further comprising forming at least one pair of plane plate members from a molded organic polymer.

9. The method according to claim 5, further comprising providing a plurality of reagent mixing means placed in series with each other.

* * * * *